United States Patent [19]
Peter, Jr. et al.

[11] Patent Number: 5,863,421
[45] Date of Patent: Jan. 26, 1999

[54] HEMODIALYSIS MACHINE WITH AUTOMATIC PRIMING BY INDUCED PRESSURE PULSES

[75] Inventors: Frederick H. Peter, Jr., Barrington; Eric Bell, Wheeling; Thomas M. Feldsein, Palatine, all of Ill.

[73] Assignee: Aksys, Ltd., Lincolnshire, Ill.

[21] Appl. No.: 929,943

[22] Filed: Sep. 15, 1997

Related U.S. Application Data

[62] Division of Ser. No. 560,439, Nov. 17, 1995, Pat. No. 5,702,606, which is a division of Ser. No. 388,275, Feb. 13, 1995, Pat. No. 5,591,344.

[51] Int. Cl.$^6$ .......................... B01D 61/30; B01D 61/32
[52] U.S. Cl. .................... 210/134; 210/108; 210/143; 210/321.69; 210/645; 210/646; 210/793
[58] Field of Search .................. 210/134, 143, 210/252, 258, 321.69, 645, 646, 793, 798, 108

[56] References Cited

U.S. PATENT DOCUMENTS

| | | | |
|---|---|---|---|
| 3,756,234 | 9/1973 | Kopp | 210/90 |
| 3,830,234 | 8/1974 | Kopp | 210/110 |
| 4,332,264 | 6/1982 | Gortz | 210/321.69 |
| 4,464,172 | 8/1984 | Lichtenstein | 604/65 |
| 4,923,612 | 5/1990 | Trivett et al. | 210/646 |
| 5,336,165 | 8/1994 | Twardowski | 604/5 |

FOREIGN PATENT DOCUMENTS

3442744 A1  6/1986  Germany.

OTHER PUBLICATIONS

Gentles et al., *Programmable Machine for Dialyzer Reuse*, Med. & Biol. Eng. & Comput., Nov. 1980 pp. 765–771.

*Primary Examiner*—John Kim
*Attorney, Agent, or Firm*—McDonnell Boehnen Hulbert & Berghoff

[57] ABSTRACT

A hemodialysis machine is described that has an extracorporeal circuit that is primed automatically prior to connection of the patient to the machine. The priming is accomplished by filling the extracorporeal circuit with a priming fluid, such as a saline or dialysate solution or blood. The blood pump and clamps in the arterial and venous lines are operated by a control system in a fashion to create multiple brief pressure pulses in the priming fluid. The pressure pulses shear air bubbles present on the blood side of the dialyzer membrane off the membrane. The blood pump is then operated to clear the bubbles from the dialyzer compartment where they are removed from the priming fluid by conventional bubble trap apparatus.

3 Claims, 60 Drawing Sheets

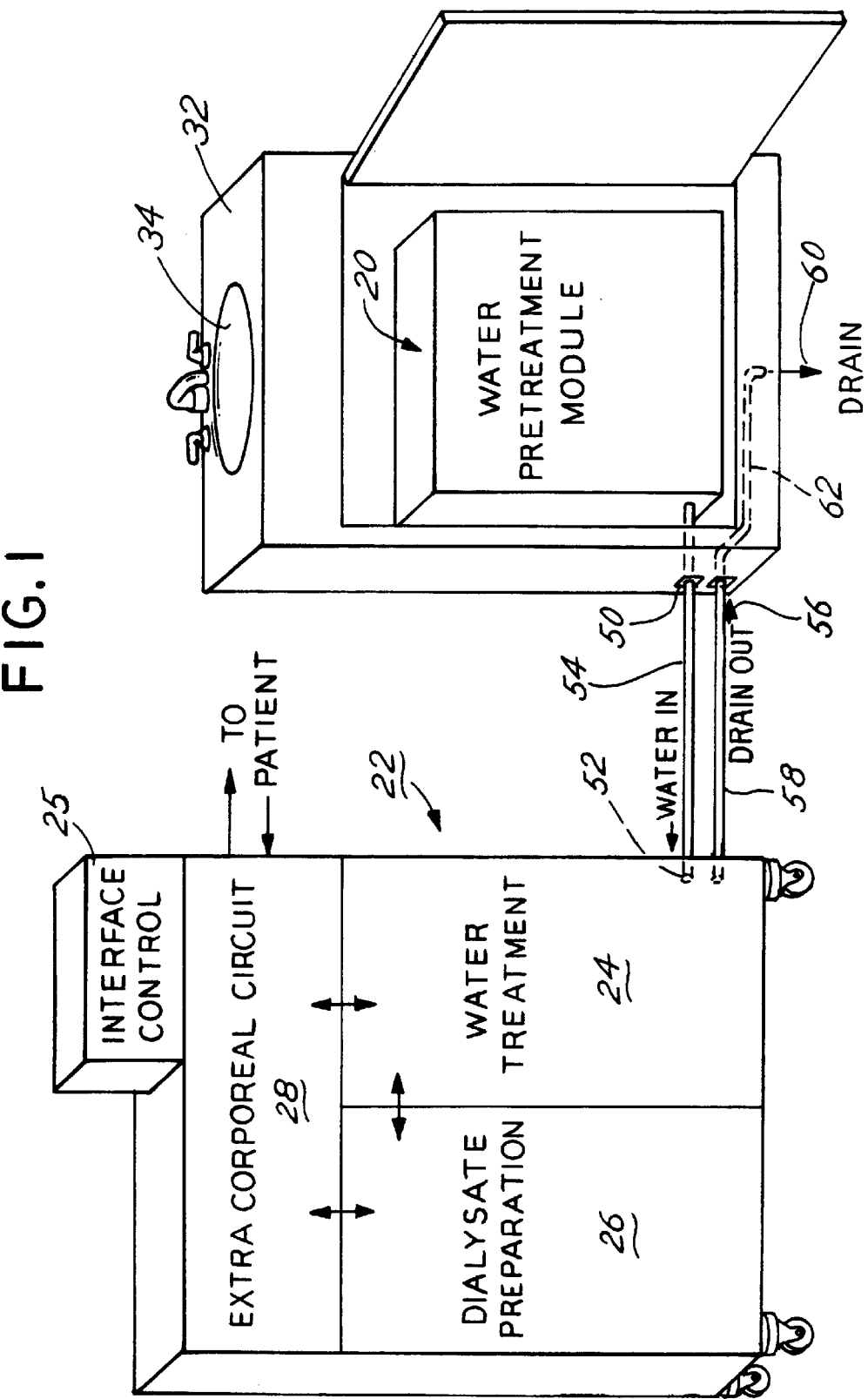

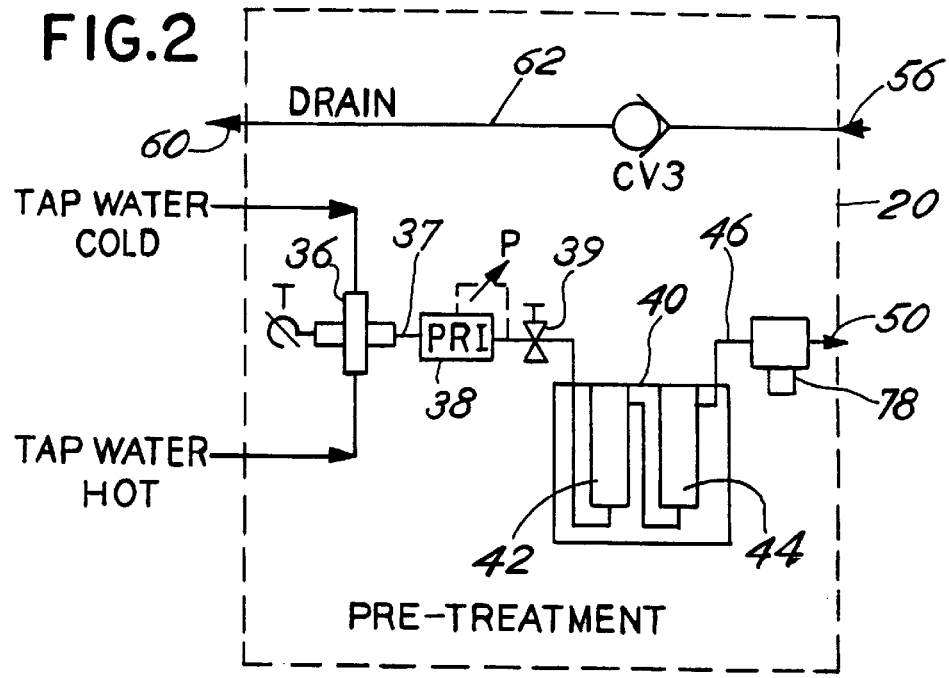
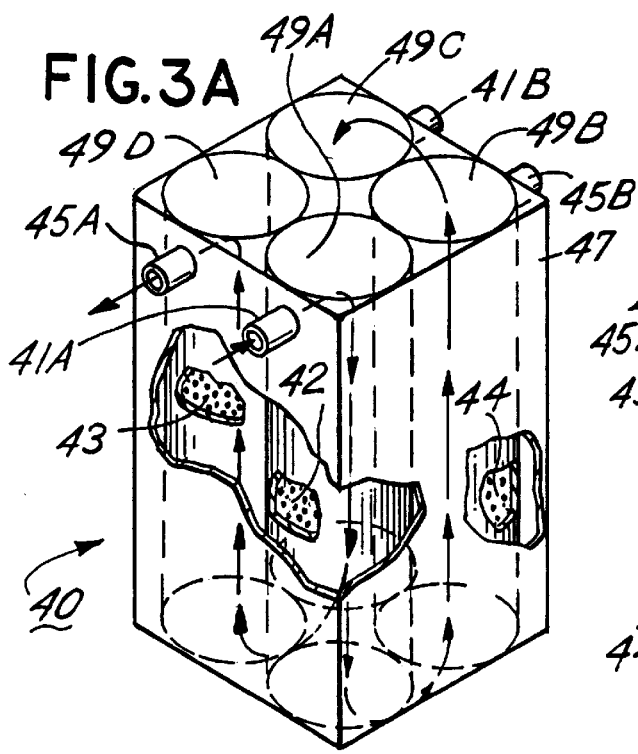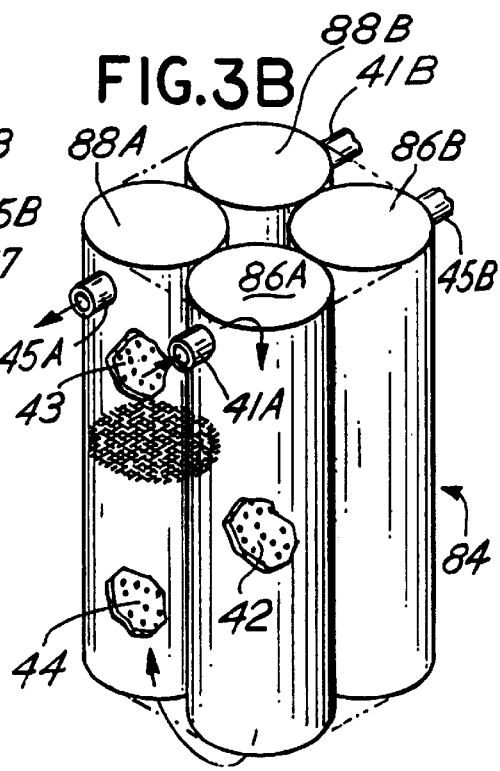

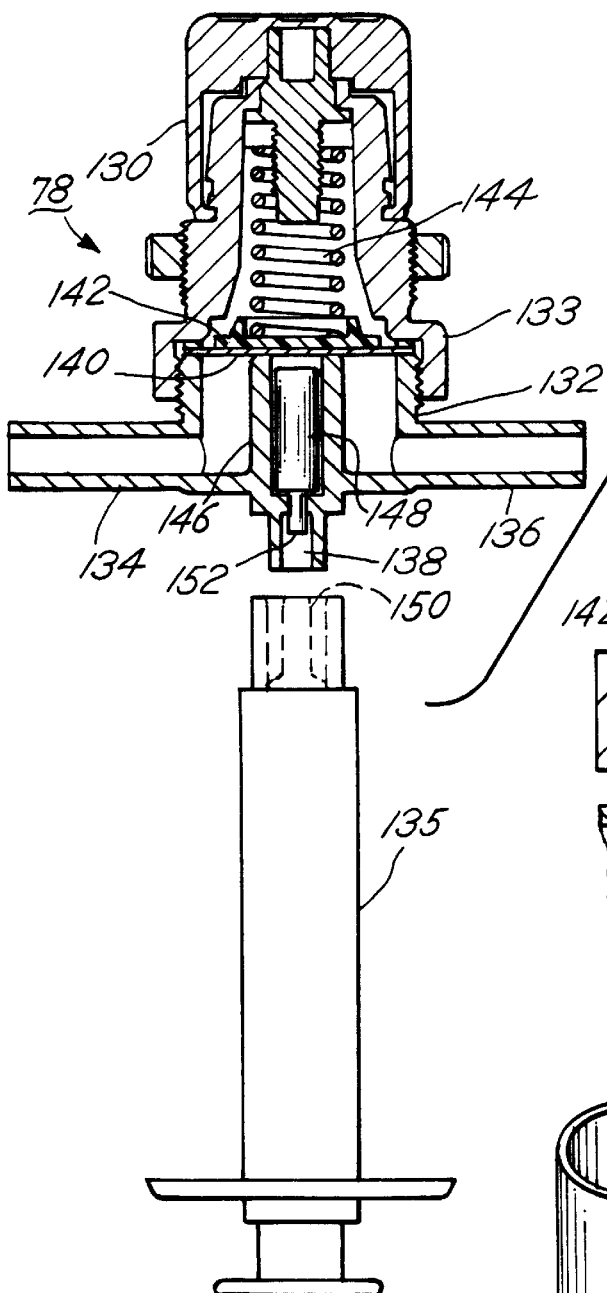
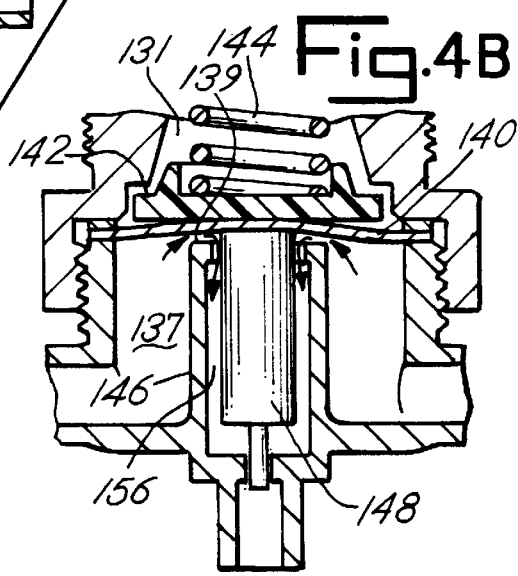
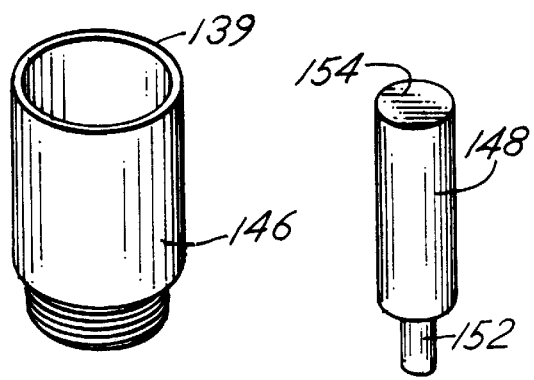

FIG. 5

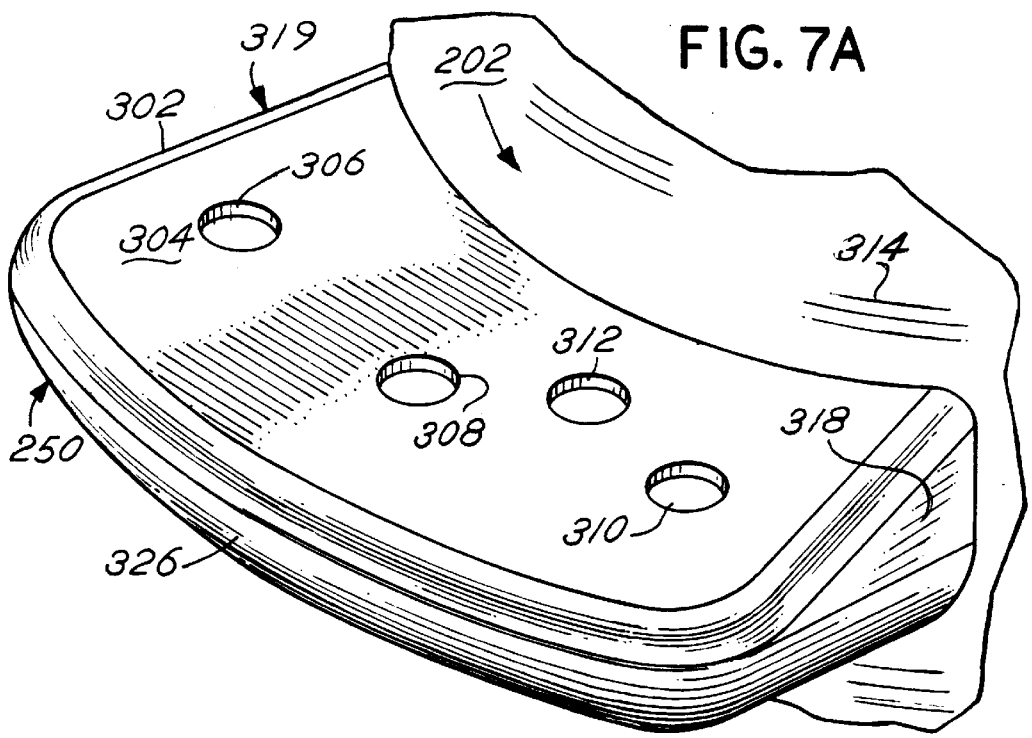
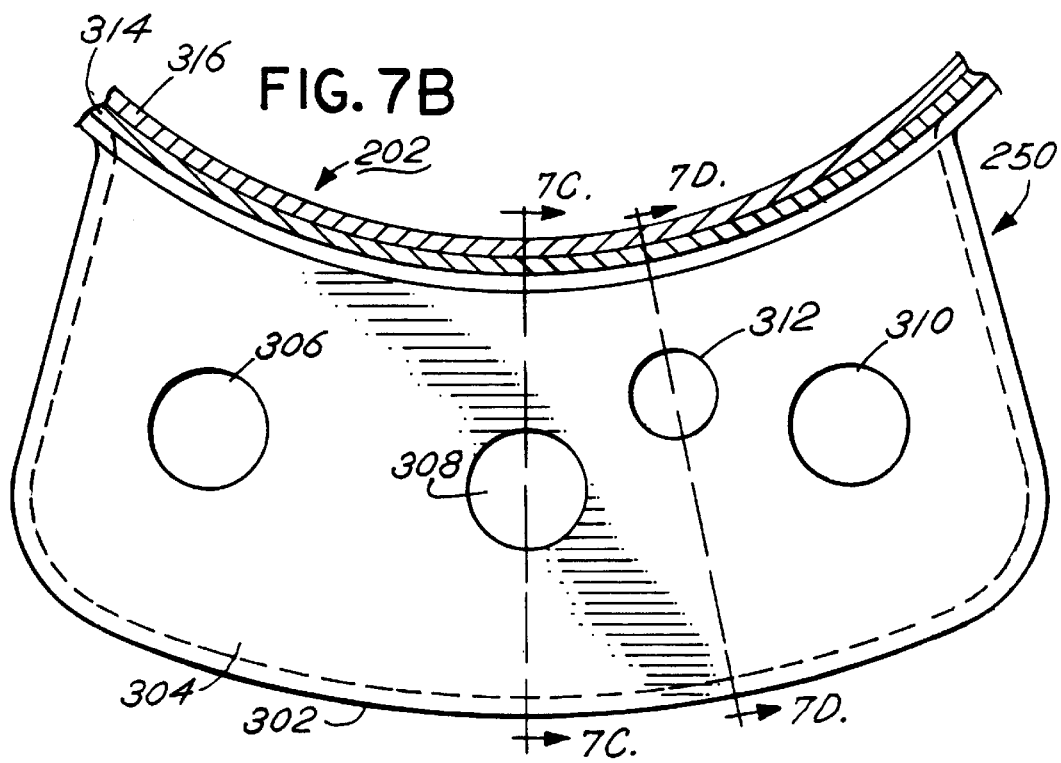

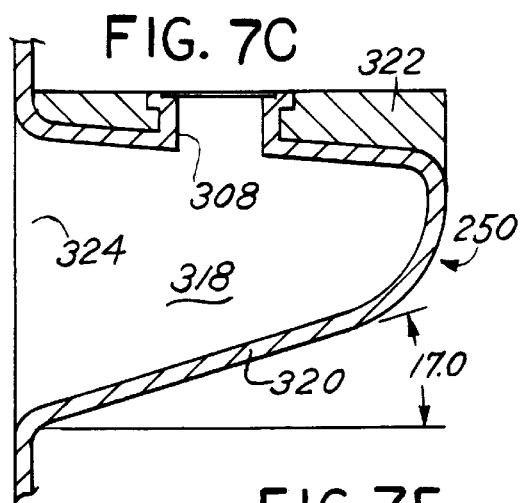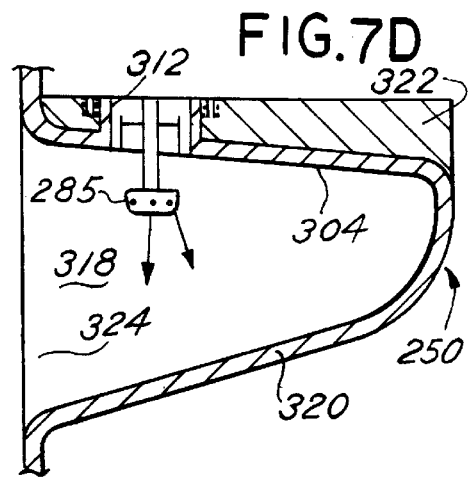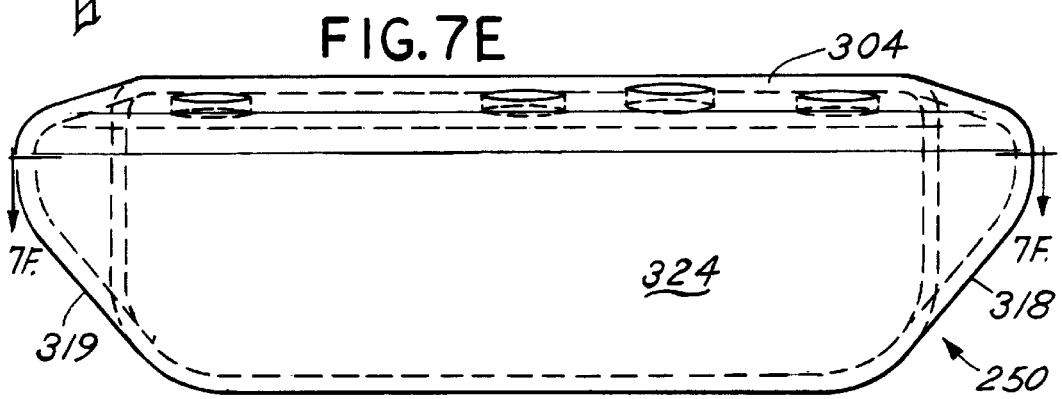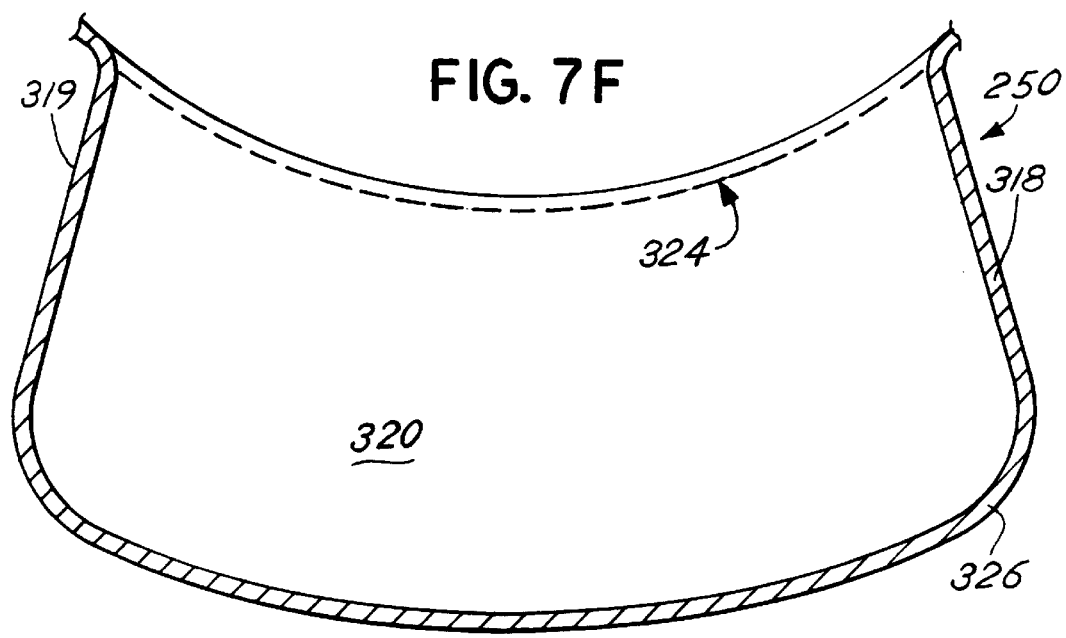

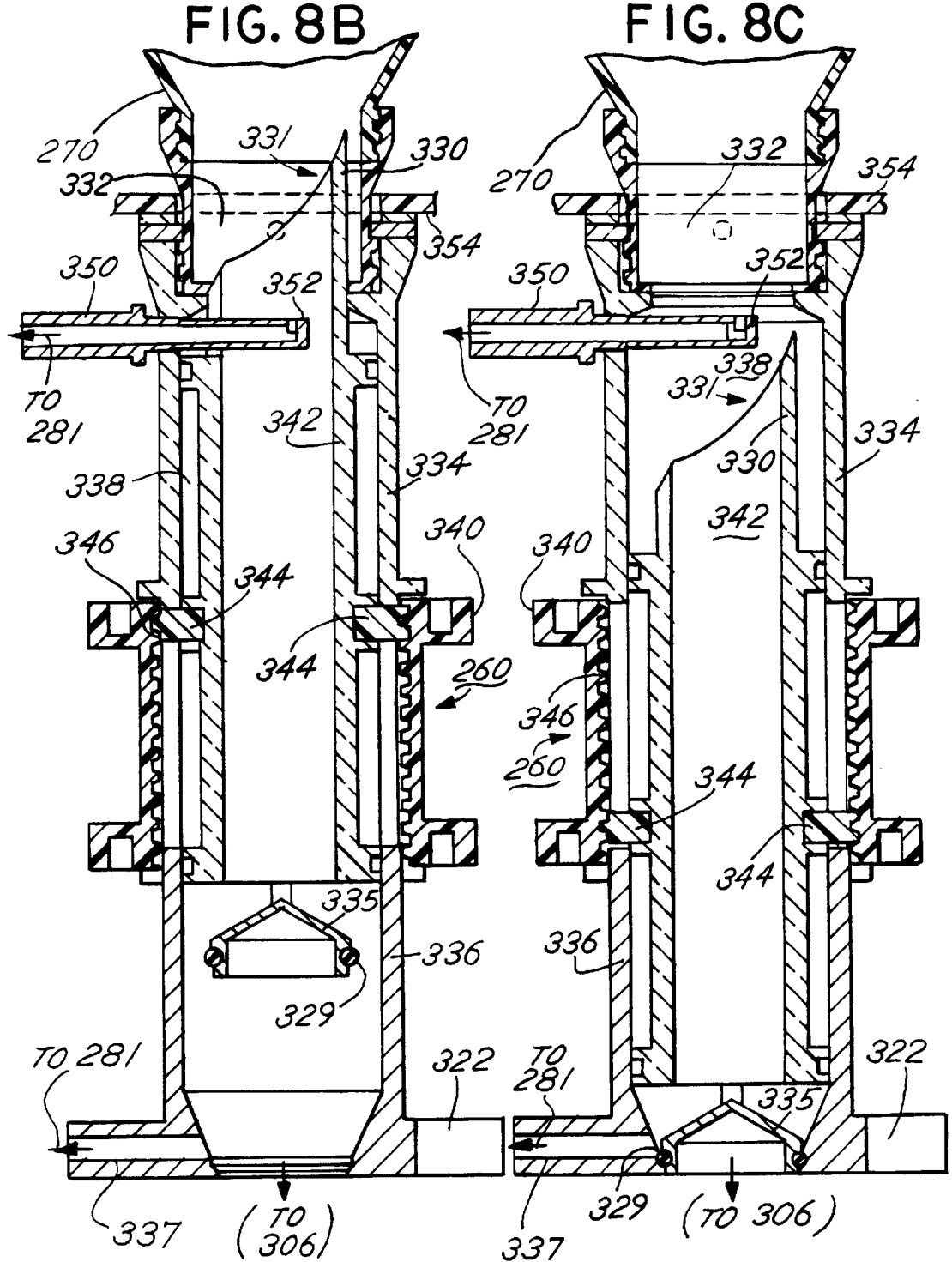

FIG. 9B
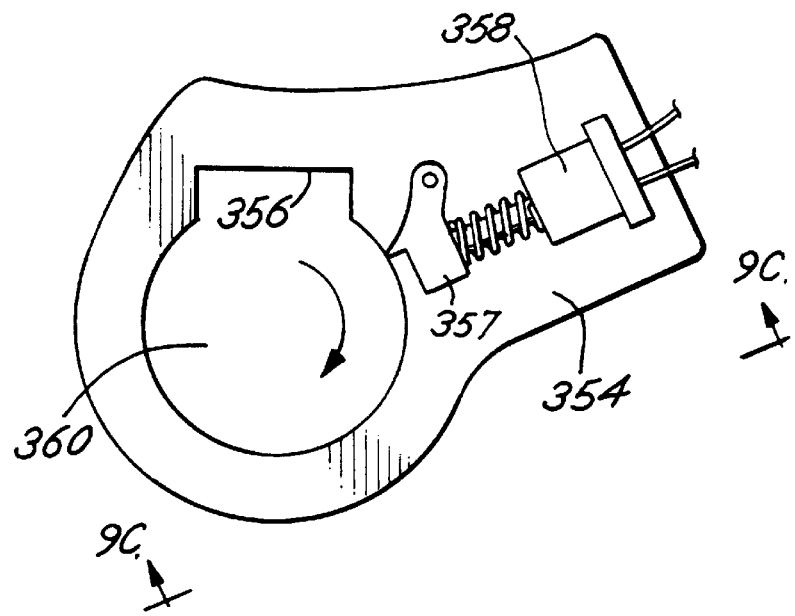
FIG. 9A
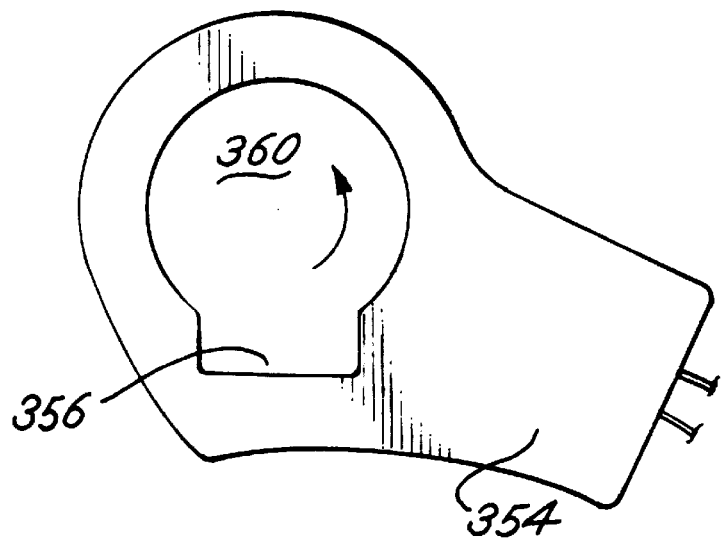
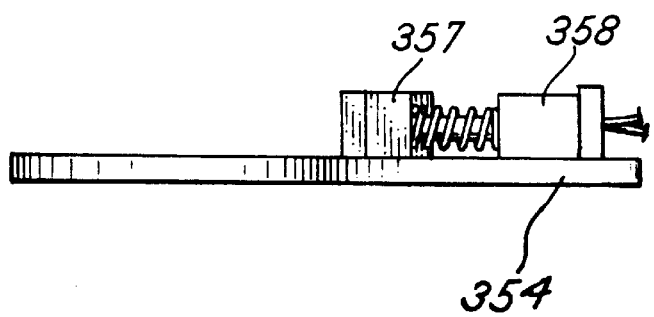
FIG. 9C

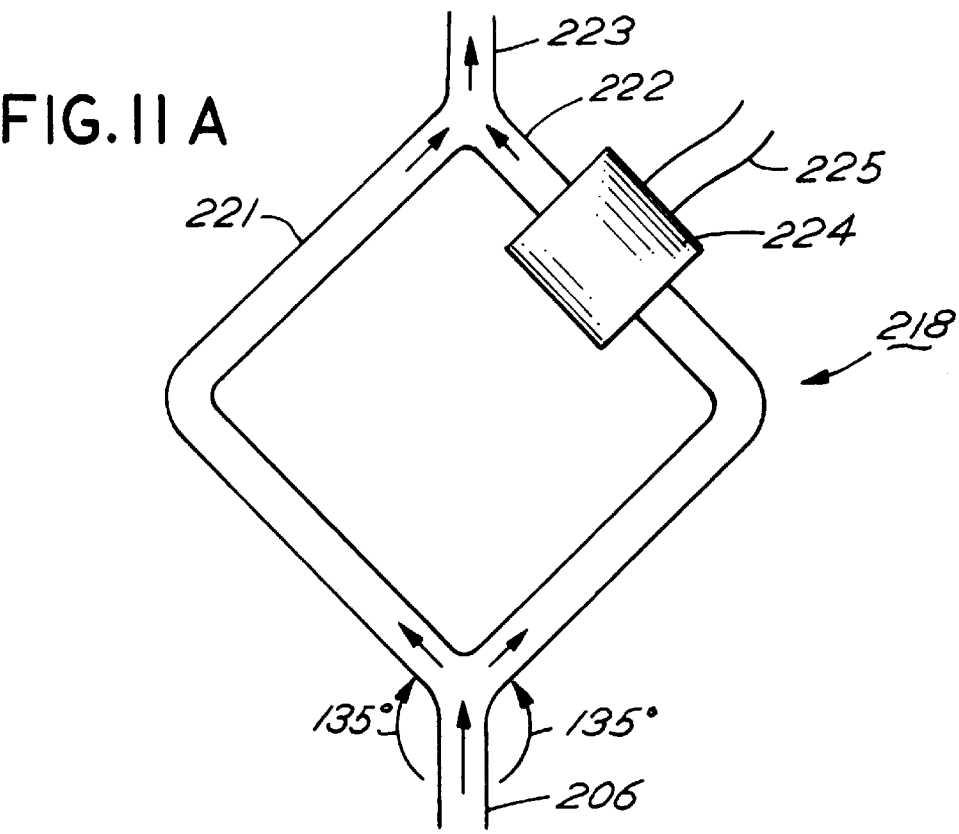
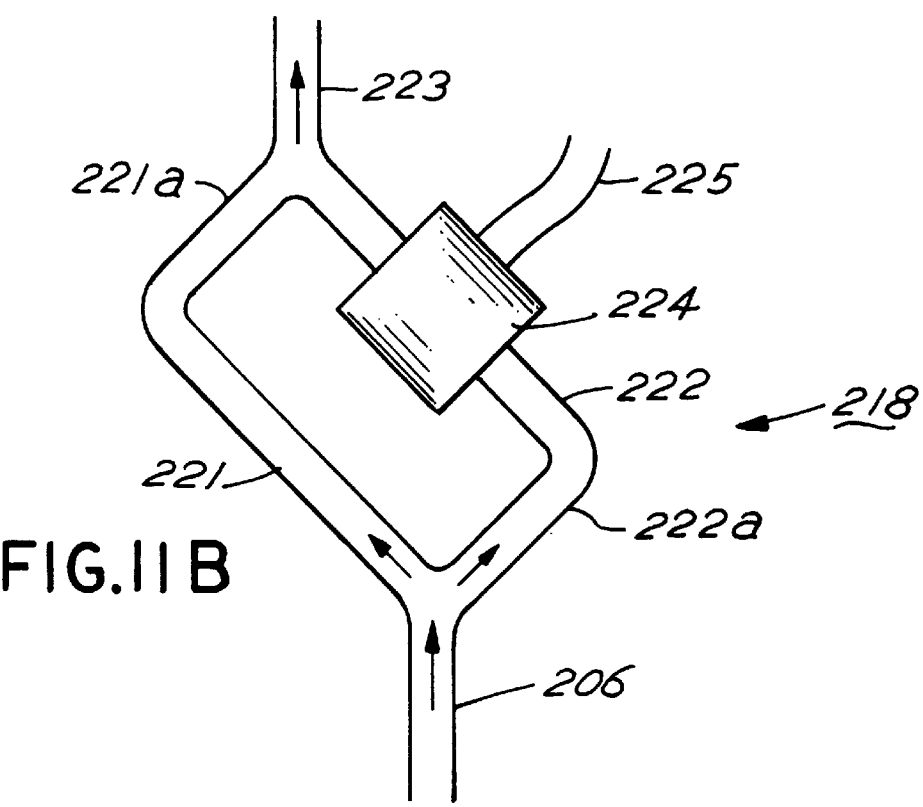

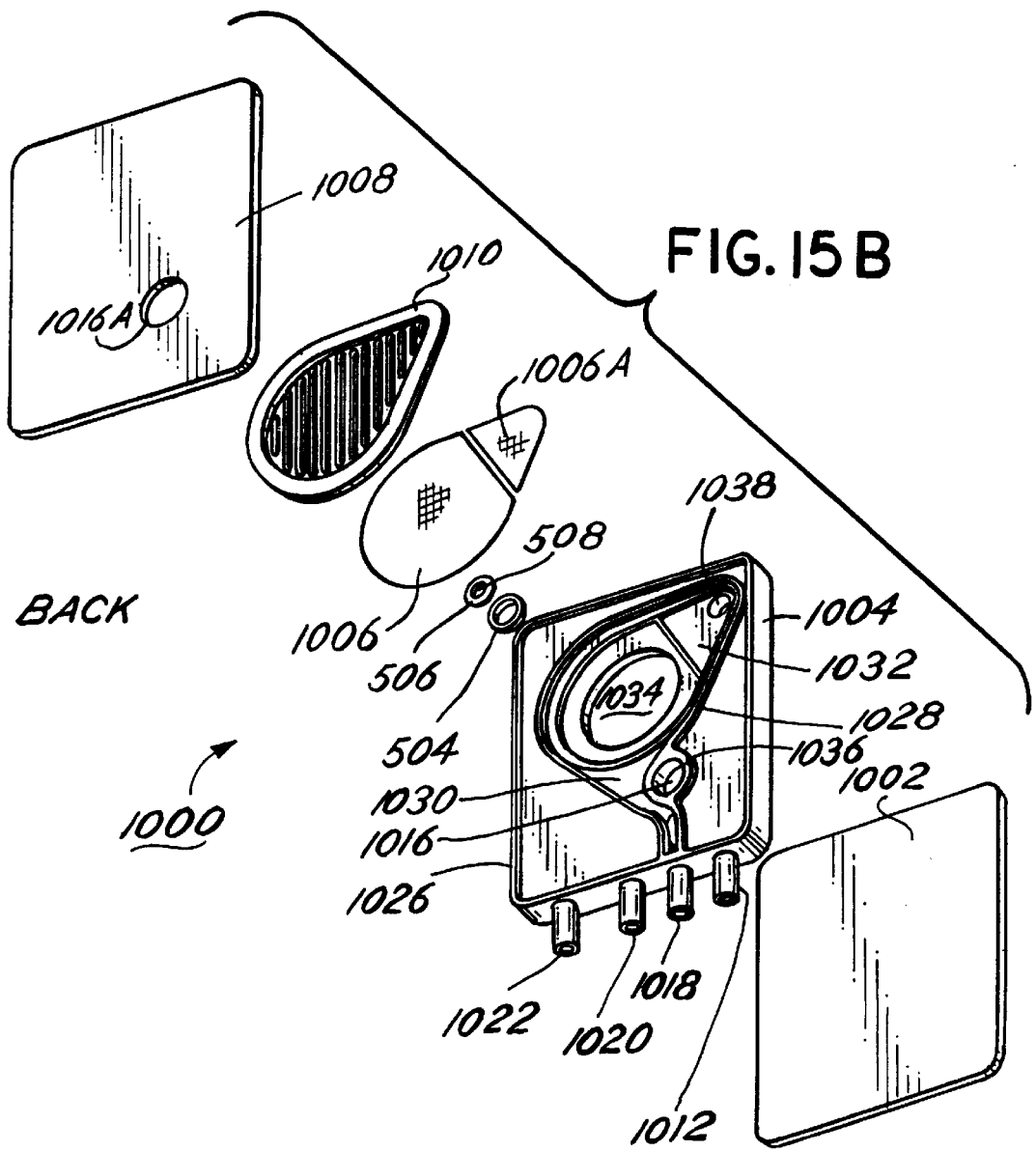

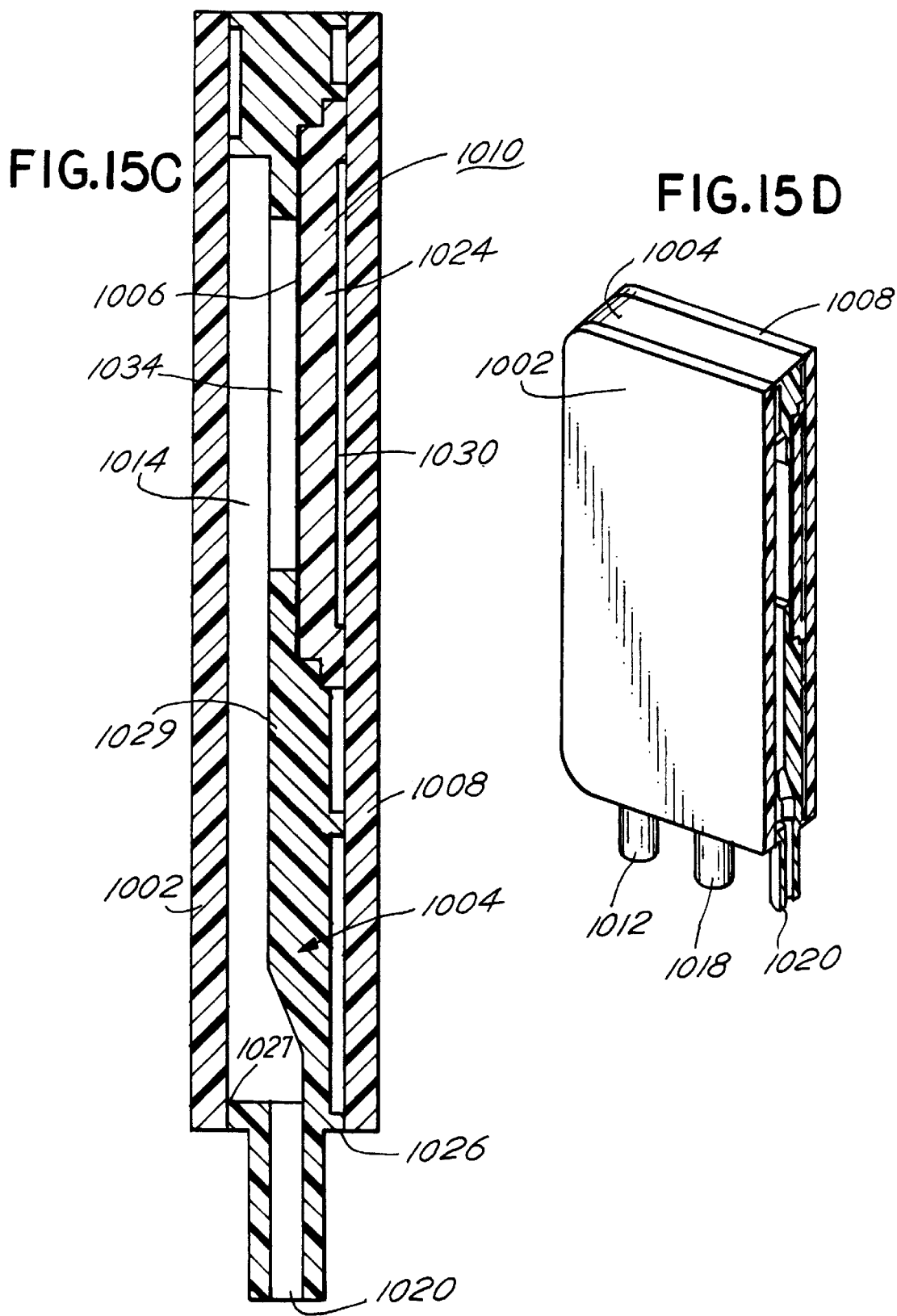

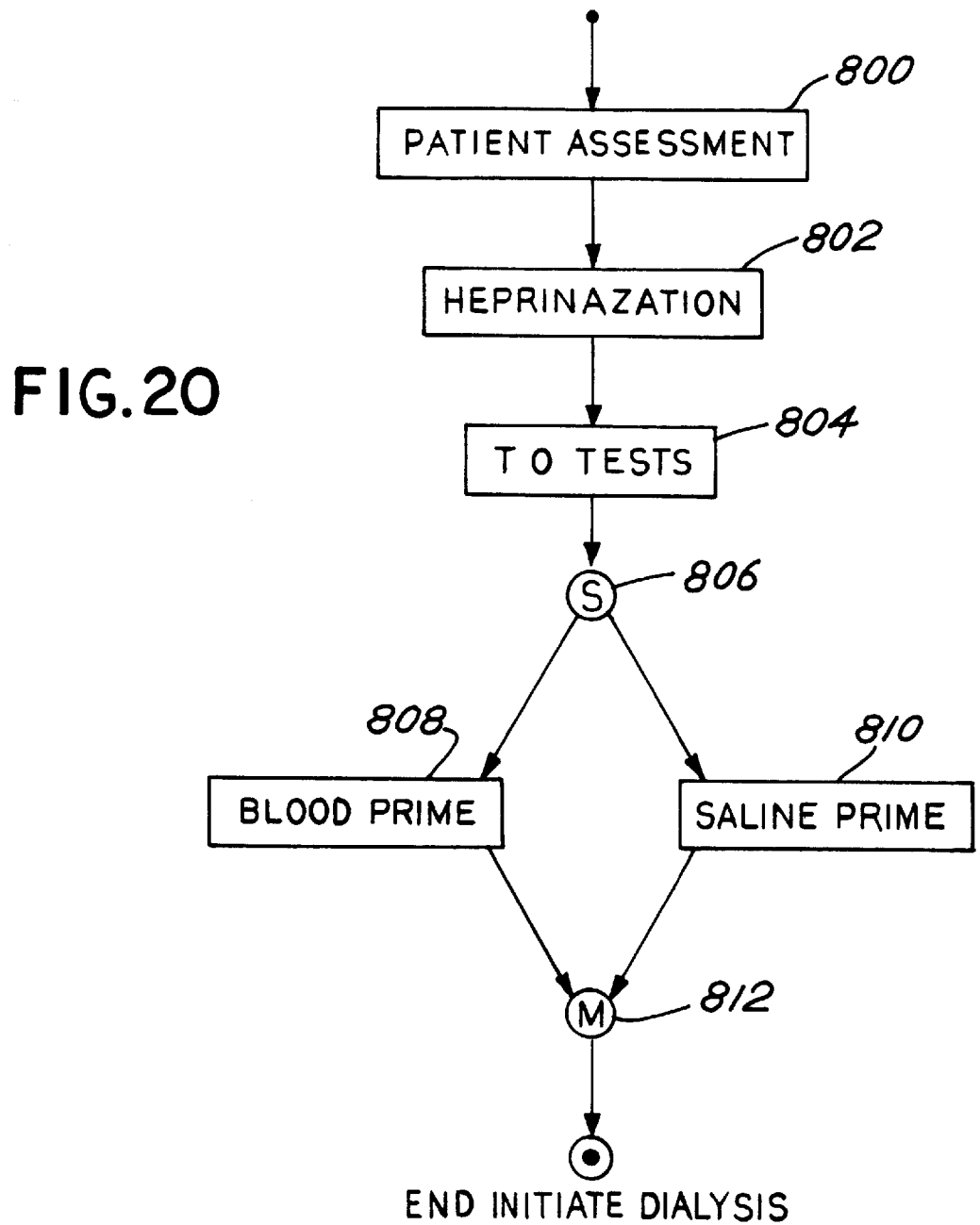

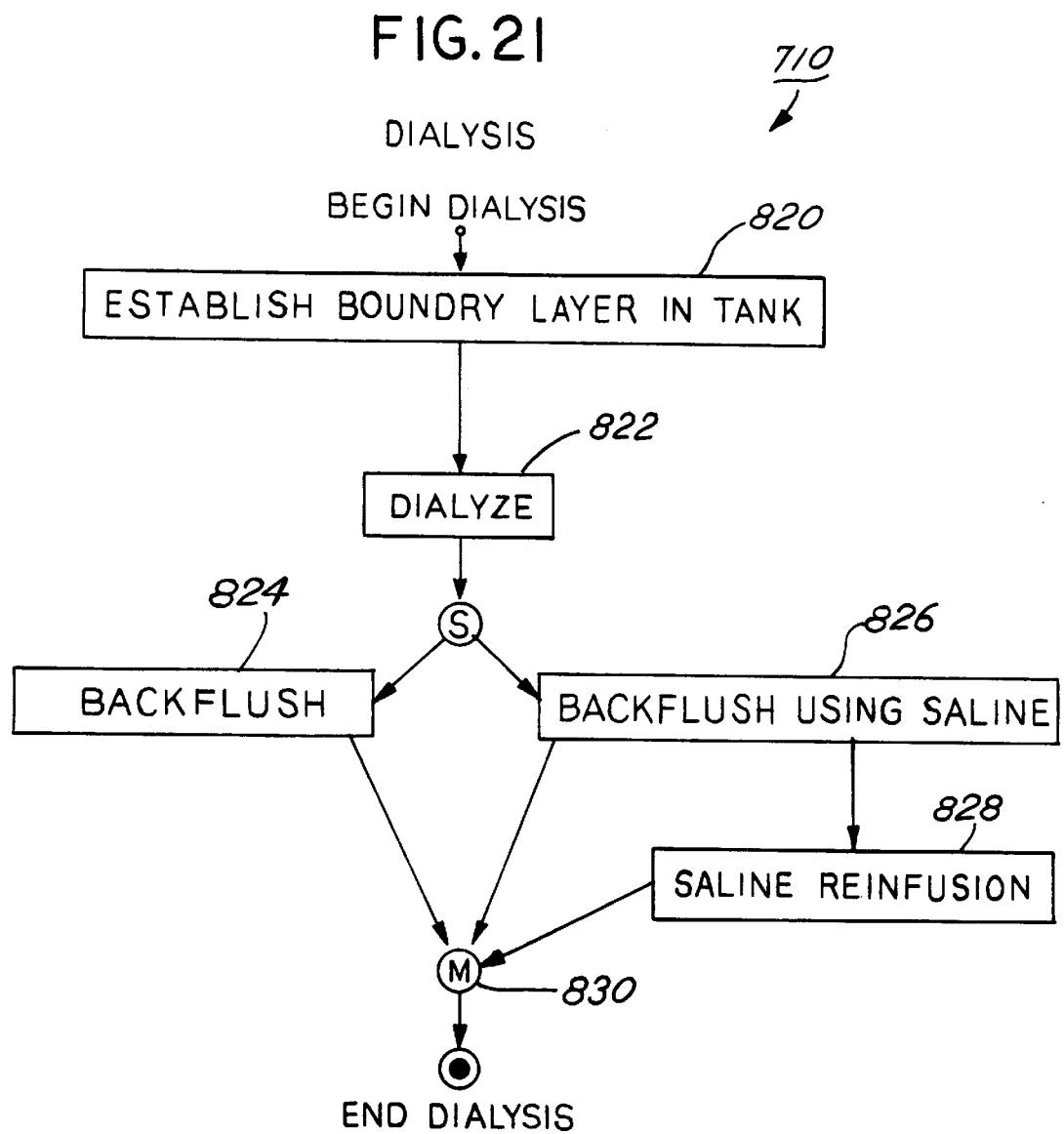

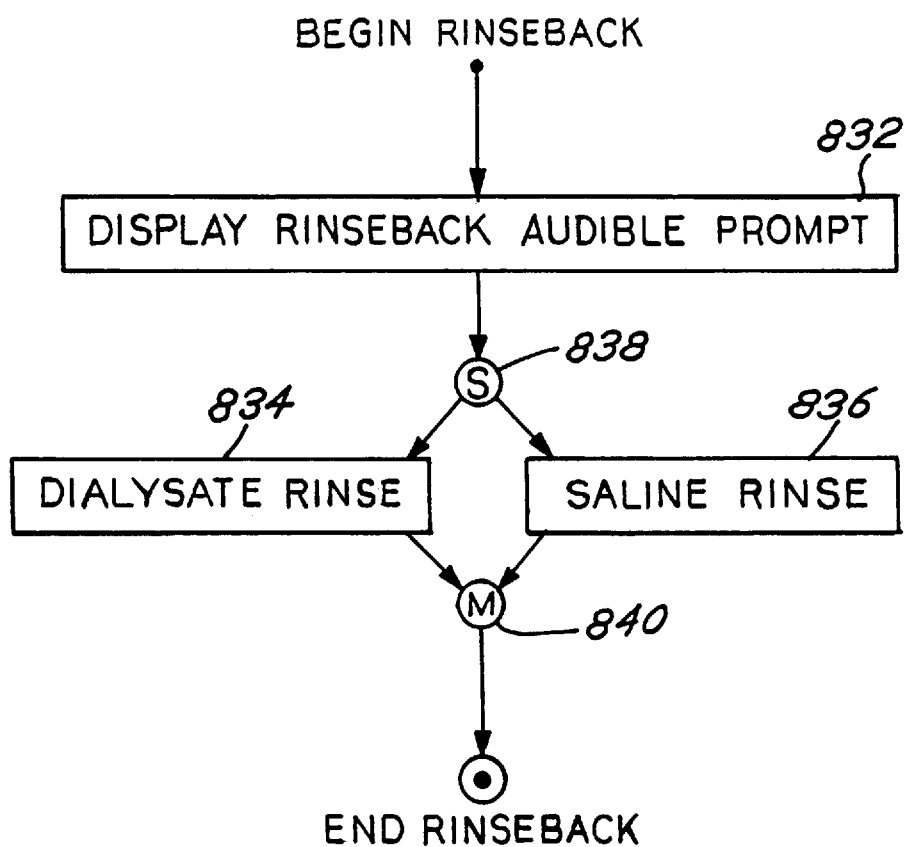

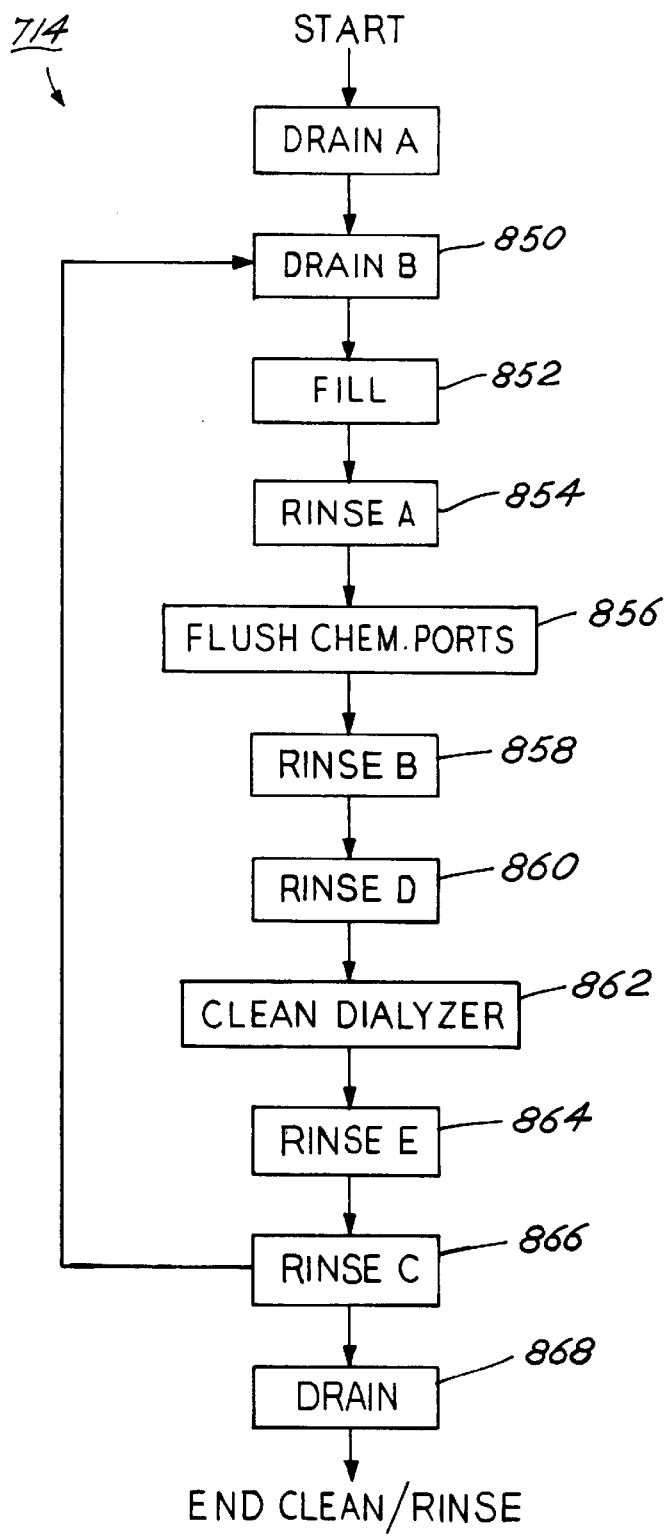

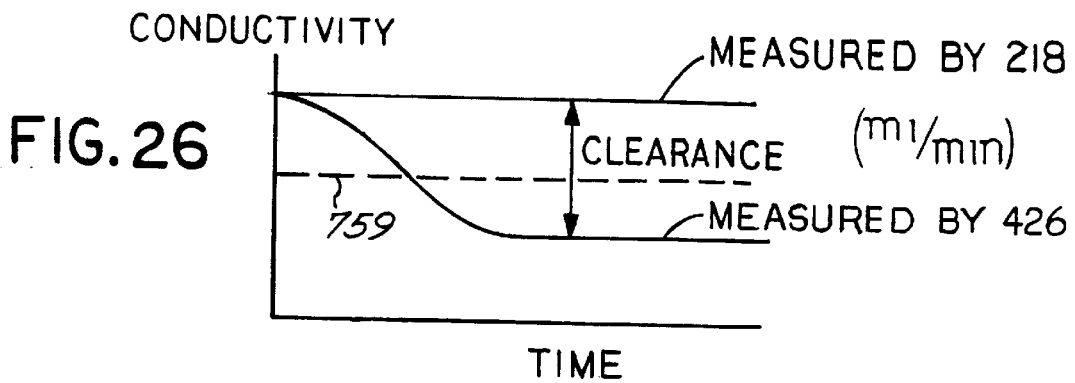
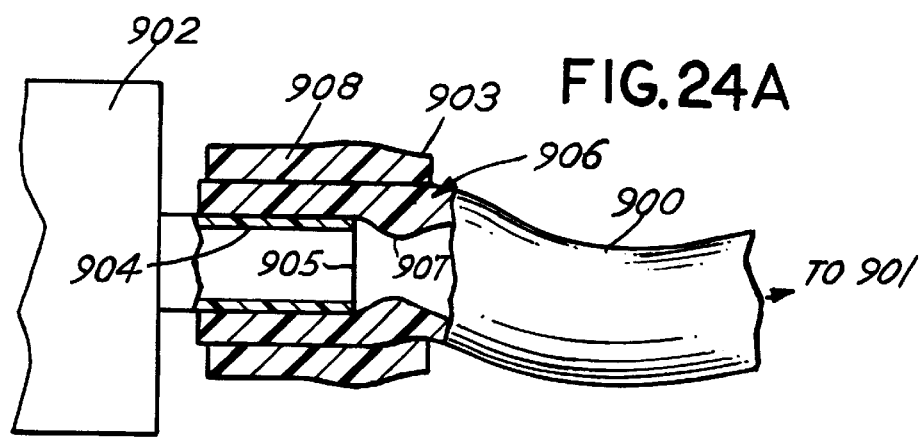
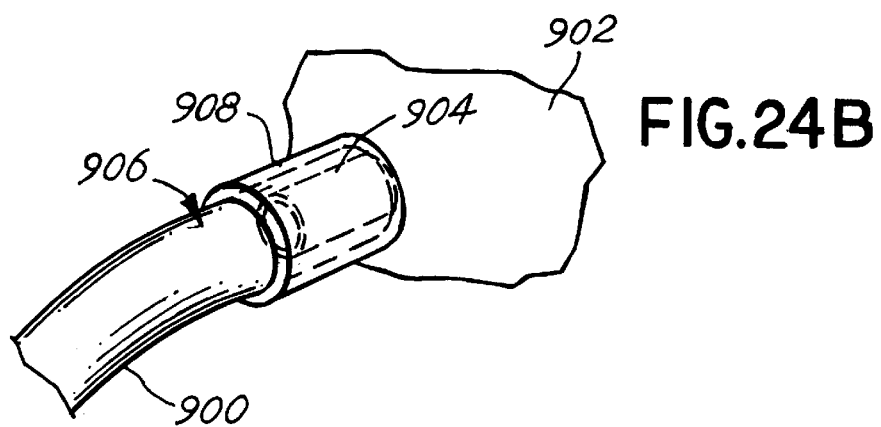

FIG. 28

| FIG. 28A |
|---|
| 28A |
| 28B |

FIG. 28A

0 = OFF
1 = ON
A = ACTIVE

| # | COMPONENT | PWR REQ'D AMP | V | INIT RO 716 | RO BYPA 718 | T-FILL 720 | EC FILL 731 | P/DFILL 733 | TST B 724 | UFPCAL 725 | UF BKF 746 | DF TST 727 | UF TST 729 | FILL UF 737 |
|---|---|---|---|---|---|---|---|---|---|---|---|---|---|---|
| 1 | 74 | | 5 | A | A | A | A | O | A | O | O | O | O | A |
| 2 | 104 | | 5 | A | A | A | A | O | A | O | O | O | O | A |
| 3 | 94 | | | A | A | A | A | O | A | O | O | O | O | A |
| 4 | 106 | | | A | A | A | A | O | A | O | O | O | O | A |
| 5 | 72 | 0.25 | 24 | − | − | − | − | O | − | O | O | O | O | − |
| 6 | 83 | 0.25 | 24 | O | O | O | O | O | O | O | O | O | O | O |
| 7 | 108 | 0.25 | 24 | − | O | − | − | O | − | O | O | O | O | T |
| 8 | 112 | 0.4 | 24 | O | O | O | O | O | O | O | O | O | O | O |
| 9 | 80 | 0.25 | 24 | O | − | O | O | − | O | O | O | O | O | O |
| 10 | 96 | 2.8 | 115 | − | − | − | − | O | − | O | O | O | O | − |
| 11 | 76 | 0.0009 | 5 | A | A | A | A | O | A | O | O | O | O | A |
| 12 | 92 | 0.0009 | 5 | A | A | A | A | O | A | O | O | O | O | A |
| 13 | 98 | 0.0009 | 5 | A | A | A | A | O | A | O | O | O | O | A |

FIG. 28B

O = OFF
I = ON
A — ACTIVE

| # | EC PRIM | DE SER | MIX A | MIX C | MIX D | DP TEST | EP CAL | C TEST | DCLR TST | T-RECIRC | DIALYZE |
|---|---------|--------|-------|-------|-------|---------|--------|--------|----------|----------|---------|
| 1 | O | A | A | O | O | O | O | O | O | O | O |
| 2 | O | A | A | O | O | O | O | O | O | O | O |
| 3 | O | A | A | O | O | O | O | O | O | O | O |
| 4 | O | A | A | O | O | O | O | O | O | O | O |
| 5 | O | — | — | O | O | O | O | O | O | O | O |
| 6 | O | O | O | O | O | O | O | O | O | O | O |
| 7 | O | — | — | O | O | O | O | O | O | O | O |
| 8 | O | O | O | O | O | O | O | O | O | O | O |
| 9 | — | O | O | O | O | O | — | O | O | O | O |
| 10 | O | A | A | O | O | O | O | O | O | O | O |
| 11 | O | A | A | O | O | O | O | O | O | O | O |
| 12 | O | A | A | O | O | O | O | O | O | O | O |
| 13 | O | A | A | O | O | O | O | O | O | O | O |

FIG. 29

| 29 A | 29 B |
|------|------|

FIG. 29A

| # | COMPON | PWR REQ'D | | BCKFLSH 824 | R BACK 834 | DRAIN A 850 | DRAIN B 850 | DRAIN C 738 | RINSE A 854, 760 | RINSE B 858, 756 | RINSE C 866, 750 | RINSE D 744, 860 | RINSE E 748, 864 |
|---|--------|-----|-----|--------|-------|---------|---------|---------|---------|---------|---------|---------|---------|
|   |        | AMP | V   |        |       |         |         |         |         |         |         |         |         |
| 1 | 74     |     | 5   | 0      | 0     | 0       | 0       | 0       | 0       | 0       | 0       | A       | 0       |
| 2 | 104    |     | 5   | 0      | 0     | 0       | 0       | 0       | 0       | 0       | 0       | A       | 0       |
| 3 | 94     |     |     | 0      | 0     | 0       | 0       | 0       | 0       | 0       | 0       | A       | 0       |
| 4 | 106    |     |     | 0      | 0     | 0       | 0       | 0       | 0       | 0       | 0       | A       | 0       |
| 5 | 72     | 0.25| 24  | 0      | 0     | 0       | 0       | 0       | 0       | 0       | 0       | —       | 0       |
| 6 | 83     | 0.25| 24  | 0      | 0     | 0       | 0       | 0       | 0       | 0       | 0       | 0       | 0       |
| 7 | 108    | 0.25| 24  | 0      | 0     | 0       | 0       | 0       | 0       | 0       | 0       | F       | 0       |
| 8 | 112    | 0.4 | 24  | 0      | 0     | 0       | 0       | 0       | 0       | 0       | 0       | 0       | —       |
| 9 | 80     | 0.25| 24  | 0      | 0     | 0       | 0       | 0       | 0       | 0       | 0       | 0       | 0       |
| 10| 96     | .28 | 115 | 0      | 0     | 0       | 0       | 0       | 0       | —       | 0       | —       | 0       |
| 11| 76     |0.009| 5   | 0      | 0     | 0       | 0       | 0       | 0       | 0       | 0       | A       | 0       |
| 12| 92     |0.009| 5   | 0      | 0     | 0       | 0       | 0       | 0       | 0       | 0       | A       | 0       |
| 13| 98     |0.009| 5   | 0      | 0     | 0       | 0       | 0       | 0       | 0       | 0       | A       | 0       |

FIG. 29 B

| # | 726 FILL HOT | 732 H-R CRC A | 734 H-R CRC B | 728 H-R CRC C | 730 H-R CRC D | 810 SAL PRIME | 826 BAG BKF | 836 EGR NSB | 808 BID PRIME |
|---|---|---|---|---|---|---|---|---|---|
| 1 | A | A | A | A | A | O | O | O | O |
| 2 | A | A | A | A | A | O | O | O | O |
| 3 | A | O | O | O | O | O | O | O | O |
| 4 | A | O | O | O | O | O | O | O | O |
| 5 | — | O | O | O | O | O | O | O | O |
| 6 | O | — | — | — | — | O | O | O | O |
| 7 | F | — | — | — | — | O | O | O | O |
| 8 | O | — | — | — | O | O | O | O | O |
| 9 | O | — | D | D | D | O | O | O | O |
| 10 | — | A | — | — | O | O | O | O | O |
| 11 | A | A | A | A | A | O | O | O | O |
| 12 | A | A | A | A | A | O | O | O | O |
| 13 | A | A | A | A | A | O | O | O | O |

FIG. 30

| 30A | 30B | 30C |
|-----|-----|-----|

R200F ← ml/min FLOW RATE
↙ REVERSE DIRECTION
P = PRIMING
D = DRAIN

FIG. 30A

PwR REQ'D

| # | ID | AMP | V | INIT RO | RO BYPA | T-FILL | EC FILL | P/D FILL | T TST B | UFP CAL |
|---|----|-----|---|---------|---------|--------|---------|----------|---------|---------|
| 1 | 214 | 0.0009 | 5 | O | O | O | A | A | A | A |
| 2 | 242L | | 24 | O | O | P | O | O | O | R200F |
| 3 | 242H | | 24 | O | O | O | 300F | O | O | R400F |
| 4 | 212L | 0.6 | 24 | O | O | O | O | 600F | 500F | O |
| 5 | 212H | 1.5 | 24 | O | O | P | 3000F | O | O | 3000F |
| 6 | 216 | | 5 | O | O | O | O | A | A | O |
| 7 | LT | 0.0009 | 5 | A | A | A | A | A | A | A |
| 8 | LUF | 0.0009 | 5 | A | A | A | TA | A | A | A |
| 9 | 218 | | | O | O | O | O | A | A | O |
| 10 | 241 | | 24 | O | O | P | O | A | A | A |
| 11 | V6 | 0.25 | 24 | O | O | I | I | I | I | I |
| 12 | 220 | 0.25 | 24 | O | O | O | O | O | O | O |
| 13 | 232 | 0.25 | 24 | O | O | P | I | O | O | P |
| 14 | V9 | 0.25 | 24 | O | O | O | O | O | O | I |
| 15 | V13 | 0.25 | 24 | O | O | O | I | O | O | O |
| 16 | V15 | 0.25 | 24 | O | O | P | I | P | O | O |
| 17 | 236 | 0.25 | 24 | O | O | P | O | O | O | I |
| 18 | V17 | 0.25 | 24 | O | O | O | O | O | O | O |
| 19 | V18 | 0.25 | 24 | O | O | O | O | O | I | I |
| 20 | V19 | 0.25 | 24 | O | O | O | O | O | O | O |
| 21 | V21 | 0.25 | 24 | O | O | O | I | I | O | O |
| 22 | V22 777 | 0.25 | 24 | O | O | O | O | O | O | O |
| 23 | 287 | 0.25 | 24 | O | O | O | O | O | O | O |
| 24 | 228 | 10 | 115 | O | O | O | O | O | O | O |
| 25 | 228 | 10 | 115 | O | O | O | O | O | O | O |
| 26 | TH 230 | | 5 | O | O | O | O | A | A | O |
| 27 | FSB 286 | | | A | A | A | A | A | A | A |
| 28 | CLMA | | | CLOSED | CLOSED | CLOSED | CLOSED | CLOSED | CLOSED | CLOSED |
| 29 | CLMB | | | CLOSED | CLOSED | CLOSED | CLOSED | CLOSED | CLOSED | CLOSED |
| 30 | 60 A | | | CLOSED | CLOSED | CLOSED | CLOSED | CLOSED | CLOSED | CLOSED |
| 31 | 288 | | 5 | AO | AO | AO | AO | AO | AO | AO |

FIG. 30 B

TH 30T → THERMISTOR TEMP(°C)

T = TRIGGER

| | UF BKF | DFI TST | UFI TEST | FILL UF | EC PRIME | DESER |
|---|---|---|---|---|---|---|
| 1 | A | A | A | A | A | A |
| 2 | R200F | O | 200F | T500F | O | O |
| 3 | O | R300F | O | O | O | O |
| 4 | O | O | P | 500F | O | O |
| 5 | O | O | P | O | 2500F | 3000F |
| 6 | O | O | O | A | A | A |
| 7 | A | A | A | A | A | A |
| 8 | A | A | A | A | A | TA |
| 9 | O | O | O | A | O | A |
| 10 | O | O | O | A | O | O |
| 11 | I | I | I | I | I | I |
| 12 | O | D | D | D | O | O |
| 13 | O | O | P | O | I | I |
| 14 | O | O | O | O | O | O |
| 15 | O | I | O | O | O | O |
| 16 | O | O | R | P | I | O |
| 17 | O | D | D/P | O | O | O |
| 18 | O | O | O | I | O | I |
| 19 | O | O | O | O | O | I |
| 20 | O | O | O | O | O | O |
| 21 | O | O | O | O | O | O |
| 22 | O | O | O | O | O | O |
| 23 | O | O | O | O | O | O |
| 24 | O | O | O | TH/37T | TH/30T | TH/30T |
| 25 | O | O | O | O | O | O |
| 26 | O | O | O | A | A | A |
| 27 | A | A | A | A | A | A |
| 28 | CLOSED | CLOSED | CLOSED | CLOSED | CLOSED | CLOSED |
| 29 | CLOSED | CLOSED | CLOSED | CLOSED | CLOSED | CLOSED |
| 30 | CLOSED | CLOSED | CLOSED | CLOSED | CLOSED | CLOSED |
| 31 | AO | AO | AO | AO | AO | AO |

FIG. 30C

A = ACTIVE
AC = ACTIVE SENSE CLOSED
AO = ACTIVE SENSE OPEN

|    | MIX A   | MIX C   | MIX D   | DPTEST  | EPCAL  | C TEST  | DCLRTST | T-RECIRC | DIALYZE |
|----|---------|---------|---------|---------|--------|---------|---------|----------|---------|
| 1  | A       | A       | A       | A       | O      | A       | A       | A        | A       |
| 2  | O       | O       | O       | R200P5  | CAL P  | O       | O       | O        | SEL F   |
| 3  | O       | O       | R500F   | O       | O      | O       | O       | O        | O       |
| 4  | O       | O       | 1000F   | O       | O      | 500F    | 200F    | SEL F    | SEL F   |
| 5  | 3000F   | 3000F   | O       | O       | O      | O       | R3000F  | O        | O       |
| 6  | A       | A       | A       | O       | O      | A       | A       | A        | A       |
| 7  | A       | A       | A       | A       | A      | A       | A       | A        | A       |
| 8  | A       | A       | A       | A       | A      | A       | A       | A        | A       |
| 9  | A       | A       | A       | O       | O      | A       | A       | A        | A       |
| 10 | O       | O       | A       | O       | O      | A       | A       | A        | A       |
| 11 | 1       | O       | 1       | R       | CAL P  | O       | O       | O        | O       |
| 12 | O       | O       | O       | O       | CAL P  | O       | O       | O        | O       |
| 13 | 1       | 1       | O       | O       | O      | O       | R       | O        | O       |
| 14 | O       | O       | O       | O       | O      | O       | O       | O        | O       |
| 15 | O       | O       | O       | O       | O      | O       | 1       | O        | O       |
| 16 | R       | O       | 1       | R       | O      | O       | 1       | O        | O       |
| 17 | O       | O       | O       | O       | O      | O       | O       | O        | O       |
| 18 | O       | O       | O       | 1       | O      | O       | O       | O        | O       |
| 19 | O       | O       | O       | O       | CALP   | 1       | O       | 1        | 1       |
| 20 | R       | 1       | O       | O       | O      | O       | O       | O        | O       |
| 21 | O       | O       | 1       | O       | O      | O       | O       | O        | O       |
| 22 | O       | O       | O       | O       | O      | O       | O       | O        | O       |
| 23 | R       | 1       | O       | O       | O      | O       | O       | O        | O       |
| 24 | TH/30T  | TH/30T  | TH/30T  | O       | O      | O       | TH/37T  | TH/37T   | TH/37T  |
| 25 | O       | O       | O       | O       | O      | O       | O       | O        | O       |
| 26 | A       | A       | A       | O       | O      | O       | A       | A        | A       |
| 27 | A       | A       | A       | A       | A      | A       | A       | A        | A       |
| 28 | DEPENDS | CLOSED  | CLOSED  | CLOSED  | CLOSED | CLOSED  | CLOSED  | CLOSED   | CLOSED  |
| 29 | DEPENDS | CLOSED  | CLOSED  | CLOSED  | CLOSED | CLOSED  | CLOSED  | CLOSED   | CLOSED  |
| 30 | DEPENDS | CLOSED  | CLOSED  | CLOSED  | CLOSED | CLOSED  | CLOSED  | CLOSED   | CLOSED  |
| 31 | AO      | AO      | AO      | AO      | AO     | AO      | AO      | AO       | AO      |

FIG.31 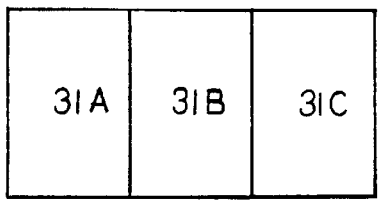

FIG.31A

| COMPONENT | PWR REQ'D. | | | | | | | | |
|---|---|---|---|---|---|---|---|---|---|
| | ID | AMP | V | BCKFLSH | R BACK | DRAIN A | DRAIN B | DRAIN C | RINSE A | RINSE B |
| 1 | 214 | 0.0009 | 5 | A | A | A | A | A | A | A |
| 2 | 242(h) | | 24 | R100F | R100F | O | O | O | O | O |
| 3 | 242(h) | | 24 | O | O | R500F | O | R500F | O | O |
| 4 | 212(L) | 0.6 | 24 | SELF | O | O | O | 300F | 500F | 1000F |
| 5 | 212(L) | 1.5 | 24 | O | M3000F | O | 3000F | O | O | O |
| 6 | 216 | | 5 | A | A | O | A | A | O | O |
| 7 | LT | 0.0009 | 5 | A | TRIGGER | A | A | A | A | A |
| 8 | LUF | 0.0009 | 5 | A | A | A | O | A | O | A |
| 9 | 218 | | | A | A | O | O | O | O | O |
| 10 | 241 | | 24 | A | A | O | O | O | A | A |
| 11 | V6 | 0.25 | 24 | O | T | O | I | I | I | I |
| 12 | 220 | 0.25 | 24 | O | O | O | I | I | O | O |
| 13 | 232 | 0.25 | 24 | O | M | O | O | O | O | R |
| 14 | V9 | 0.25 | 24 | O | I | O | O | O | O | O |
| 15 | V13 | 0.25 | 24 | O | O | O | O | O | O | O |
| 16 | V15 | 0.25 | 24 | O | M | O | O | O | O | O |
| 17 | 236 | 0.25 | 24 | O | I | O | O | I | O | O |
| 18 | V17 | 0.25 | 24 | O | O | O | D | O | O | O |
| 19 | V18 | 0.25 | 24 | O | O | O | O | O | O | O |
| 20 | V19 | 0.25 | 24 | O | O | O | O | O | O | I |
| 21 | V21 | 0.25 | 24 | O | O | O | O | O | O | I |
| 22 | 777 | 0.25 | 24 | O | O | O | O | O | O | O |
| 23 | 287 | 0.25 | 24 | O | O | O | O | O | O | I |
| 24 | 228(L) | 10 | 115 | O | O | O | O | O | O | O |
| 25 | 228(h) | 10 | 115 | O | O | O | O | O | O | O |
| 26 | 230 | | 5 | A | A | O | O | O | O | O |
| 27 | FSB 286 | | | A | A | A | A | A | A | A |
| 28 | 260A | | | CLOSED | CLOSED | CLOSED | CLOSED | CLOSED | CLOSED | CLOSED |
| 29 | 260B | | | CLOSED | CLOSED | CLOSED | CLOSED | CLOSED | CLOSED | CLOSED |
| 30 | 260C | | | CLOSED | CLOSED | CLOSED | CLOSED | CLOSED | CLOSED | CLOSED |
| 31 | FS 288 | | 5 | AO | AO | AO | AO | AO | AC | AC |

FIG. 31B

|    | RINSE C | RINSE D | RINSE E | FILL HOT | H-RCRCA | H-RCRCB |
|----|---------|---------|---------|----------|---------|---------|
| 1  | A       | A       | A       | A        | A       | A       |
| 2  | O       | O       | O       | O        | O       | O       |
| 3  | 500F    | 500FD   | O       | D500F    | R500F   | R500F   |
| 4  | O       | 1000F   | O       | O        | 100F    | O       |
| 5  | 3000F   | O       | 3000F   | O        | O       | 3000F   |
| 6  | O       | A       | O       | A        | A       | A       |
| 7  | A       | A       | A       | A        | A       | A       |
| 8  | A       | A       | A       | A        | A       | A       |
| 9  | O       | O       | O       | C        | O       | O       |
| 10 | O       | A       | O       | A        | O       | A       |
| 11 | 1       | 1       | 1       | 1        | 1       | 1       |
| 12 | O       | O       | O       | O        | 1       | D       |
| 13 | 1       | O       | 1       | 1        | O       | B       |
| 14 | O       | O       | O       | P        | O       | 1       |
| 15 | O       | O       | 1       | O        | O       | O       |
| 16 | 1       | O       | O       | O        | O       | O       |
| 17 | O       | 1       | O       | P        | O       | 1       |
| 18 | O       | R       | O       | O        | 1       | O       |
| 19 | O       | 1       | O       | O        | O       | 1       |
| 20 | O       | O       | 1       | 1        | 1       | O       |
| 21 | O       | O       | 1       | 1        | O       | O       |
| 22 | O       | O       | O       | O        | O       | O       |
| 23 | O       | O       | R       | 1        | 1       | O       |
| 24 | O       | O       | O       | O        | O       | O       |
| 25 | O       | O       | O       | TH/85T   | O       | TH/85T  |
| 26 | O       | O       | O       | A        | A       | A       |
| 27 | A       | A       | A       | A        | A       | A       |
| 28 | CLOSED  | CLOSED  | DEPEND  | DEPEND   | DISFECT | CLOSED  |
| 29 | CLOSED  | CLOSED  | DEPEND  | DEPEND   | DISFECT | CLOSED  |
| 30 | CLOSED  | CLOSED  | DEPEND  | DEPEND   | DISFECT | CLOSED  |
| 31 | AC      | AC      | AC      | AC       | AC      | AC      |

FIG. 3IC

| | H-RCRCC | H-RCRCD | SAL PRIME | BAG BKFS | EG RNSB | BID PRIME |
|---|---|---|---|---|---|---|
| 1 | A | A | O | A | A | O |
| 2 | O | 100 F | O | O | O | 200 F |
| 3 | O | O | O | O | O | O |
| 4 | O | O | O | 50F | O | O |
| 5 | 3000F | 1000 F | O | O | 3000F | O |
| 6 | A | A | A | A | O | O |
| 7 | A | A | A | A | A | A |
| 8 | A | A | O | A | A | A |
| 9 | O | O | O | A | O | O |
| 10 | O | A | O | A | O | O |
| 11 | I | I | O | O | O | O |
| 12 | D | D | O | O | O | O |
| 13 | I | O | O | O | M | O |
| 14 | O | O | O | O | O | O |
| 15 | I | O | O | O | O | O |
| 16 | I | O | O | O | M | O |
| 17 | O | I | O | O | O | O |
| 18 | O | I | O | O | O | O |
| 19 | O | O | O | I | O | O |
| 20 | I | I | O | O | O | O |
| 21 | I | O | O | O | O | O |
| 22 | O | O | O | O | O | O |
| 23 | O | I | O | O | O | O |
| 24 | O | O | O | TH37T | O | O |
| 25 | TH/85T | TH/85T | O | O | O | O |
| 26 | A | A | O | A | O | O |
| 27 | A | A | A | A | A | A |
| 28 | CLOSED | CLOSED | CLOSED | CLOSED | CLOSED | CLOSED |
| 29 | CLOSED | CLOSED | CLOSED | CLOSED | CLOSED | CLOSED |
| 30 | CLOSED | CLOSED | CLOSED | CLOSED | CLOSED | CLOSED |
| 31 | AC | AC | AC | AC | AC | AC |

FIG. 32A

| # | ID | PWR REQ'D AMP | V | INIT RO | RO BYPA | T-FILL | EC FILL | P/D FILL | T TST B | UFP CAL |
|---|---|---|---|---|---|---|---|---|---|---|
| 1 | HOST | 3 | 5 | A | A | A | A | A | A | A |
| 2 | DISPLAY | 0.8 | 24 | A | A | A | A | A | A | A |
| 3 | | | | | | | | | | |
| 4 | | | | | | | | | | |
| 5 | 500 B | 0.0009 | 5 | O | O | O | A | A | O | O |
| 6 | 500 A | 0.0009 | 5 | O | O | O | A | A | O | O |
| 7 | 500 C | 0.0009 | 5 | O | O | O | A | A | O | O |
| 8 | 775 | 0.0009 | 5 | O | O | O | A | A | O | O |
| 9 | 488 | | | O | O | O | O | O | O | O |
| 10 | 446 | | | O | O | O | O | O | O | O |
| 11 | 486 | 0.05 | 5 | O | O | O | O | O | O | O |
| 12 | 450 | 0.05 | 5 | O | O | O | O | O | O | O |
| 13 | 428 | | 5 | O | O | O | O | O | O | O |
| 14 | 490 | 0.4 | 24 | O | O | O | P | I | O | O |
| 15 | 444 | 0.4 | 24 | O | O | O | I | I | O | O |
| 16 | 479 | 0.4 | 24 | O | O | O | O | O | O | O |
| 17 | 458(L) | | 24 | O | O | O | O | PRIME | O | O |
| 18 | 458(H) | | 24 | O | O | O | 300F | O | O | O |
| 19 | 293 | | 5 | O | O | O | O | A | O | O |
| 20 | V14 | 0.25 | 24 | O | O | O | F | I | O | O |
| 21 | V20 | 0.25 | 24 | O | O | O | O | I | O | O |
| 22 | SW | | | O | O | O | AC | AC | AC | AC |
| 23 | 412 | 0.25 | 24 | O | O | P | B | I | I | I |
| 24 | 414 | 0.25 | 24 | O | O | P | O | O | O | O |
| 25 | 416 | 0.25 | 24 | O | O | P | F | I | O | O |
| 26 | 408 | | 5 | O | O | O | O | A | A | O |
| 27 | 424 | | 5 | O | O | O | O | O | A | O |
| 28 | 426 | | | O | O | O | O | O | A | O |
| 29 | 410 | 0.0009 | 5 | O | O | O | A | A | A | O |
| 31 | BSD | | | O | O | O | O | O | O | O |
| 32 | CO | | | O | O | O | PRIME | OPEN | O | O |

FIG. 32B

| # | UF BID | DFI TST | UFI TST | FILL UF | EC PRIME | DESER |
|---|---|---|---|---|---|---|
| 1 | A | A | A | A | A | A |
| 2 | A | A | A | A | A | A |
| 3 | | | | | | |
| 4 | | | | | | |
| 5 | O | A | O | A | A | O |
| 6 | O | A | O | A | A | O |
| 7 | O | A | O | A | A | O |
| 8 | O | A | O | A | A | O |
| 9 | O | O | O | O | O | O |
| 10 | O | O | O | O | O | O |
| 11 | O | O | O | O | A | O |
| 12 | O | A | O | O | A | O |
| 13 | O | O | O | O | O | O |
| 14 | O | O | O | 1 | P | O |
| 15 | O | 1 | O | 1 | 1 | O |
| 16 | O | O | O | O | P | O |
| 17 | O | 200F | O | 200F | O | O |
| 18 | O | O | O | O | P | O |
| 19 | O | O | O | O | O | O |
| 20 | O | PR | O | O | P | O |
| 21 | O | O | O | 1 | 1 | O |
| 22 | AC | AC | AC | AC | AC | AC |
| 23 | 1 | O | P/T | 1 | O | O |
| 24 | O | 1 | O | O | O | O |
| 25 | O | O | O | O | 1 | O |
| 26 | O | O | O | A | O | O |
| 27 | O | O | O | A | O | O |
| 28 | O | O | O | O | O | O |
| 29 | A | A | A | A | A | O |
| 30 | O | O | O | O | O | O |
| 31 | O | CLOSED | O | O | PRIME | O |

FIG. 32C

| # | MIX A | MIX C | MIX D | DPTEST | EPCAL | C TEST | DCLRTST | RECIRC | DIALYZE |
|---|---|---|---|---|---|---|---|---|---|
| 1 | A | A | A | A | A | A | A | A | A |
| 2 | A | A | A | A | A | A | A | A | A |
| 3 | | | | | | | | | |
| 4 | | | | | | | | | |
| 5 | A | A | A | A | A | A | A | A | A |
| 6 | A | A | A | A | A | A | A | A | A |
| 7 | A | A | A | A | A | A | A | A | A |
| 8 | A | A | A | A | A | A | A | A | A |
| 9 | O | O | O | O | O | O | O | A | A |
| 10 | O | O | O | O | O | O | O | A | A |
| 11 | O | O | O | O | O | O | O | N SEN | N SEN |
| 12 | O | O | O | O | O | O | O | L SEN | L SEN |
| 13 | O | O | O | O | O | O | O | A | A |
| 14 | I | I | I | I | I | I | I | I | I |
| 15 | I | I | I | I | I | I | I | I | I |
| 16 | O | O | O | O | O | O | O | O | O |
| 17 | 200F | 200F | 200F | O | O | 200F | O | SELF | O |
| 18 | O | O | O | O | O | O | 500F | O | SEL P |
| 19 | O | O | A | O | O | O | O | O | O |
| 20 | O | O | I | O | O | O | I | O | O |
| 21 | I | I | I | I | I | I | O | O | O |
| 22 | AC | AC | AC | AC | AC | AC | AC | AO | AO |
| 23 | O | O | O | I | O | I | R | I | B |
| 24 | O | O | I | O | I | O | I | O | I |
| 25 | O | O | B | O | I | O | I | O | I |
| 26 | O | O | A | O | O | A | A | A | A |
| 27 | O | O | A | O | O | A | A | A | A |
| 28 | O | O | A | O | O | A | A | A | A |
| 29 | O | O | A | A | A | A | A | A | A |
| 30 | O | O | A | O | O | A | O | A | A |
| 31 | O | O | I | CLOSED | CLOSED | O | PRIME | OPEN | OPEN |

FIG.33

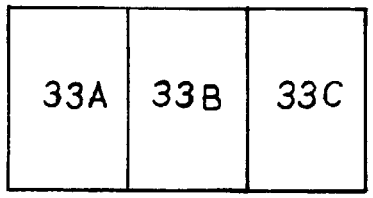

FIG.33A

| # | ID | AMP | V | BCKFLSH | R BACK | DRAIN A | DRAIN B | DRAIN C | RINSE A | RINSE B |
|---|---|---|---|---|---|---|---|---|---|---|
| 1 | HOST | 3 | 5 | A | A | A | A | A | A | A |
| 2 | DISPLAY | 0.8 | 24 | A | A | A | A | A | A | A |
| 3 | | | | | | | | | | |
| 4 | | | | | | | | | | |
| 5 | 500B | 0.0009 | 5 | A | A | A | O | O | A | A |
| 6 | 500A | 0.0009 | 5 | A | A | A | O | O | A | A |
| 7 | 500C | 0.0009 | 5 | A | A | A | O | O | A | A |
| 8 | 775 | 0.0009 | 5 | A | A | A | O | O | A | A |
| 9 | 488 | | | A | A | O | O | O | O | O |
| 10 | 446 | | | A | A | O | O | O | O | O |
| 11 | 486 | 0.05 | 5 | NSEN | NSEN | O | O | O | O | O |
| 12 | 450 | 0.05 | 5 | NSEN | NSEN | O | O | O | O | O |
| 13 | 428 | | 5 | A | A | O | O | O | O | O |
| 14 | 490 | 0.4 | 24 | I | I | I | O | O | I | I |
| 15 | 444 | 0.4 | 24 | I | I | I | O | O | I | I |
| 16 | 779 | 0.4 | 24 | O | O | O | O | O | O | O |
| 17 | 458(L) | | 24 | R50F | R50F | O | O | O | O | 200 F |
| 18 | 458(H) | | 24 | O | O | R250F | O | O | R250F | O |
| 19 | 293 | | 5 | O | O | A | O | O | O | O |
| 20 | V14 | 0.25 | 24 | O | T | I | O | O | I | I |
| 21 | V20 | 0.25 | 24 | O | T | I | O | O | I | I |
| 22 | SW | | | AO | AO | AC | AC | AC | AC | AC |
| 23 | 412 | 0.25 | 24 | I | O | O | O | O | O | O |
| 24 | 414 | 0.25 | 24 | I | D | O | O | O | I | I |
| 25 | 416 | 0.25 | 24 | O | O | I | O | O | O | I |
| 26 | 408 | | 5 | A | A | O | O | O | O | O |
| 27 | 424 | | 5 | A | O | O | O | O | O | O |
| 28 | 426 | | | O | O | O | O | O | O | O |
| 29 | 410 | 0.0009 | 5 | A | TRIGGER | O | O | O | A | A |
| 30 | BSD | | | A | A | A | O | O | O | O |
| 31 | CO | | | OPEN | OPEN | O | O | O | O | O |

FIG. 33 B

| # | RINSE C | RINSE D | RINSE E | FILL HOT | H-R CRCA | H-RCRCB |
|---|---------|---------|---------|----------|----------|---------|
| 1 | A | A | A | A | A | A |
| 2 | A | A | A | A | A | A |
| 3 |   |   |   |   |   |   |
| 4 |   |   |   |   |   |   |
| 5 | O | O | A | A | A | A |
| 6 | O | O | A | A | A | A |
| 7 | O | O | A | A | A | A |
| 8 | O | O | A | A | A | A |
| 9 | O | O | O | O | O | O |
| 10 | O | O | O | O | O | O |
| 11 | O | O | O | O | O | O |
| 12 | O | O | O | O | O | O |
| 13 | O | O | O | O | O | O |
| 14 | O | O | I | I | I | I |
| 15 | O | O | I | I | I | I |
| 16 | O | O | O | O | O | O |
| 17 | O | O | O | 200F | 200F | 200F |
| 18 | O | O | T500F | O | O | O |
| 19 | O | O | O | A | A | A |
| 20 | O | O | I | I | O | O |
| 21 | O | O | O | I | I | I |
| 22 | AC | AC | AC | AC | AC | AC |
| 23 | O | I | O | O | O | I |
| 24 | O | O | O | B | O | O |
| 25 | O | O | O | I | O | O |
| 26 | O | O | O | A | A | A |
| 27 | O | O | O | A | A | A |
| 28 | O | O | O | C | O | O |
| 29 | O | A | O | A | O | A |
| 30 | O | O | O | O | O | O |
| 31 | O | O | O | O | O | O |

FIG.33 C

| # | H-RCRC C | H-RCRC D | SAL PRIME | BAG BKF | EGR NAB | BID PRIME |
|---|---|---|---|---|---|---|
| 1 | A | A | A | A | A | A |
| 2 | A | A | A | A | A | A |
| 3 | | | | | | |
| 4 | | | | | | |
| 5 | A | A | A | A | A | A |
| 6 | A | A | A | A | A | A |
| 7 | A | A | A | A | A | TRIGGER |
| 8 | A | A | A | A | A | TRIGGER |
| 9 | O | O | O | A | TRIGGER | TRIGGER |
| 10 | O | O | O | TRIGGER | A | TRIGGER |
| 11 | O | O | O | A | A | A |
| 12 | O | O | O | A | A | A |
| 13 | O | O | O | A | O | A |
| 14 | 1 | 1 | 1 | 1 | 1 | P |
| 15 | 1 | 1 | 1 | 1 | 1 | P |
| 16 | O | O | 1 | 1 | 1 | O |
| 17 | O | 200F | 100F | 100F | 100F | 100F |
| 18 | 500F | O | O | O | O | O |
| 19 | A | A | O | O | O | O |
| 20 | 1 | O | P | O | T | O |
| 21 | O | 1 | O | O | T | O |
| 22 | AC | AC | AO | AO | AO | AO |
| 23 | O | O | O | B | O | O |
| 24 | O | 1 | O | O | O | O |
| 25 | O | 1 | O | O | O | 1 |
| 26 | A | A | O | A | O | O |
| 27 | A | A | O | A | O | A |
| 28 | O | O | O | A | O | A |
| 29 | O | A | O | A | O | O |
| 30 | O | O | O | O | A | O |
| 31 | O | O | O | OPEN | OPEN | O |

FIG. 34

| FIG.34 |
|---|
| 34A | 34B |

FIG. 34A

| ALARMS | # | INIT RO | RO BYPA | T-FILL | EC FILL | P/D FILL | T TST B | UF PCAL | UF BID | DFI TST | UFI TST |
|---|---|---|---|---|---|---|---|---|---|---|---|
| LOW WATER PRESS | 1 | A | A | A | A | A | A | O | O | O | O |
| PRI PRE TREAT SERV | 2 | A | A | A | A | A | A | O | O | O | O |
| RO REJECT LOW | 3 | A | A | A | A | A | A | O | O | O | O |
| RO HIGH PRESS | 4 | A | A | A | A | A | A | O | O | O | O |
| P/D FILL ERROR | 5 | O | O | O | O | A | O | O | O | ? | O |
| CHEM LOAD-TANK | 6 | O | O | O | O | O | O | O | A? | O | A? |
| CHEM LOAD CONDO | 7 | O | O | O | O | O | O | O | O | O | O |
| PFILTEST FAIL | 8 | O | O | O | O | O | O | O | O | A | A |
| TEMP TEST A FAIL | 9 | O | O | O | O | O | O | O | O | O | O |
| TEMP TEST A-TF FAIL | 10 | O | O | O | O | O | O | O | O | O | O |
| T/C TEST B FAIL | 11 | O | O | O | O | O | O | O | O | O | O |
| DIALYZER TEST FAIL | 12 | O | O | O | O | O | O | O | O | D | O |
| DIALYZER CHG CAUTION | 13 | O | O | O | O | O | O | O | O | D | O |
| BYPASS VALVE FAIL | 14 | O | O | O | O | O | O | O | O | O | O |
| UF PRESS TEST FAIL | 15 | O | O | O | O | O | O | O | O | O | A |
| A/V LINE CONNECT E | 16 | O | O | O | O | O | O | A | A | A | O |
| A/V LINE SW ERROR | 17 | O | O | O | A | A | A | O | O | A | A |
| DRAIN LINE DISCONNECT | 18 | A | A | A | A | O | A | O | O | A | A |
| DRAIN ERROR | 19 | A | A | A | A | O | A | O | O | A | A |

FIG. 34B

| # | FILL UF | EC PRIM | DESER | MIX A | MIX C | MIX D | DP TEST | EPCAL | CTEST | DCLRTST | T-RECIRC | DIALYZE |
|---|---------|---------|-------|-------|-------|-------|---------|-------|-------|---------|----------|---------|
| 1 | A | O | A | A | O | O | O | O | O | O | O | O |
| 2 | A | O | A | A | O | O | O | O | O | O | O | O |
| 3 | A | O | A | A | O | O | O | O | O | O | O | O |
| 4 | A | O | A | A | O | O | O | O | O | O | O | O |
| 5 | O | ? | O | O | O | O | O | O | O | O | O | O |
| 6 | A | O | O | A | O | O | O | O | O | O | O | O |
| 7 | O | O | O | A | A | A | O | O | O | A | O | O |
| 8 | O | O | O | O | O | O | O | O | O | O | O | O |
| 9 | O | O | O | O | O | A | O | O | O | O | O | O |
| 10 | O | O | O | O | O | O | O | O | O | O | O | O |
| 11 | O | O | O | O | O | O | O | O | ? | O | O | O |
| 12 | O | ? | O | O | O | O | O | O | O | D | O | O |
| 13 | O | O | O | O | O | O | D | D | O | D | O | O |
| 14 | O | O | O | O | O | O | D | D | O | O | O | O |
| 15 | O | O | O | O | O | O | A | O | O | O | O | O |
| 16 | O | O | A | A | A | A | A | A | A | A | A | A |
| 17 | A | O | A | A | O | O | O | O | O | A | O | A |
| 18 | A | O | A | A | O | O | O | O | O | O | O | O |
| 19 | A | A | A | A | O | O | O | O | O | A | O | O |

FIG.35

| | 35A | 35B |
|---|---|---|

FIG.35A

| ALARMS | # | HOLD FLSH | R BACK | DRAIN A | DRAIN B | DRAIN C | RINSE A | RINSE B | RINSE C | RINSE D | RINSE E | FILL HOT |
|---|---|---|---|---|---|---|---|---|---|---|---|---|
| LOW WATER PRESS | 1 | O | O | O | O | O | O | O | O | A | O | A |
| PRI PRE TREAT SERV | 2 | O | O | O | O | O | O | O | O | A | O | A |
| RO REJECT LOW | 3 | O | O | O | O | O | O | O | O | A | O | A |
| RO HIGH PRESS | 4 | O | O | O | O | O | O | O | O | A | O | A |
| P/D FILL ERROR | 5 | O | O | O | O | O | O | O | O | O | O | O |
| CHEM LOAD-TANK | 6 | O | A | O | O | O | O | O | O | O | O | O |
| CHEM LOAD CONDO | 7 | O | O | O | O | O | O | O | O | O | O | O |
| PFILTEST FAIL | 8 | O | O | O | O | O | O | O | O | O | O | O |
| TEMP TEST A FAIL | 9 | O | O | O | O | O | O | O | O | O | O | O |
| TEMP TEST A-TF FAIL | 10 | O | O | O | O | O | O | O | O | O | O | O |
| T/C TEST B FAIL | 11 | O | O | O | O | O | O | O | O | O | O | O |
| DIALYZER TEST FAIL | 12 | O | O | O | O | O | O | O | O | O | O | O |
| DIALYZER CHG CAUTION | 13 | O | O | O | O | O | O | O | O | O | O | O |
| BYPASS VALVE FAIL | 14 | O | O | O | O | O | O | O | O | O | O | O |
| UF PRESS TEST FAIL | 15 | O | O | O | O | O | O | O | O | O | O | O |
| A/V LINE CONNECT E | 16 | O | O | A | A | A | A | A | A | O | O | A |
| A/V LINE SW ERROR | 17 | A | A | A | A | A | A | A | A | A | A | A |
| DRAIN LINE DISCONNECT | 18 | O | A | A | A | A | A | O | O | A | O | A |
| DRAIN ERROR | 19 | O | A | A | A | A | A | O | O | A | O | A |

FIG. 35B

| # | H-R CRC A | H-R CRC B | H-R CRC C | H-R CRC D | SEL PRIME | BAG BKF | EGR NAB | BID PRIME |
|---|---|---|---|---|---|---|---|---|
| 1 | O | O | O | O | O | O | O | O |
| 2 | O | O | O | O | O | O | O | O |
| 3 | O | O | O | O | O | O | O | O |
| 4 | O | O | O | O | O | O | O | O |
| 5 | O | O | O | O | O | O | O | O |
| 6 | O | O | O | O | O | A | O | O |
| 7 | O | O | O | O | O | O | O | O |
| 8 | D | O | O | O | O | O | O | O |
| 9 | D | O | O | O | O | O | O | O |
| 10 | D | O | O | O | O | O | O | O |
| 11 | O | O | O | O | O | O | O | O |
| 12 | O | O | O | O | O | O | O | O |
| 13 | O | O | O | O | O | O | O | O |
| 14 | O | O | O | O | O | O | O | O |
| 15 | O | O | O | O | A | O | O | O |
| 16 | A | A | A | A | A | A | A | A |
| 17 | A | D | D | D | D | D | A | O |
| 18 | O | D | D | D | D | O | A | O |
| 19 | O | D | D | D | D | O | A | O |

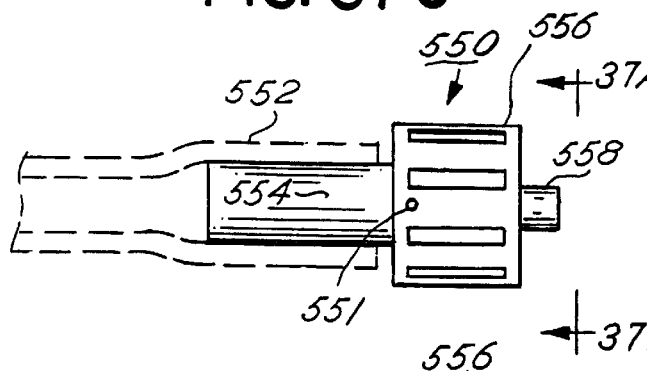
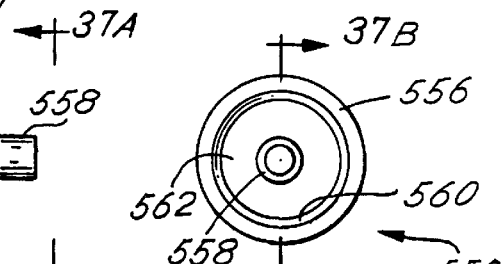
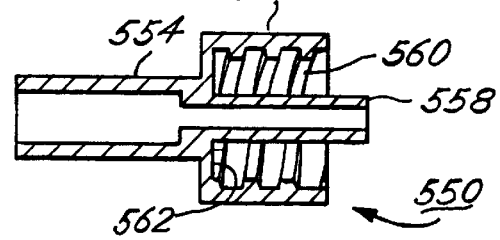
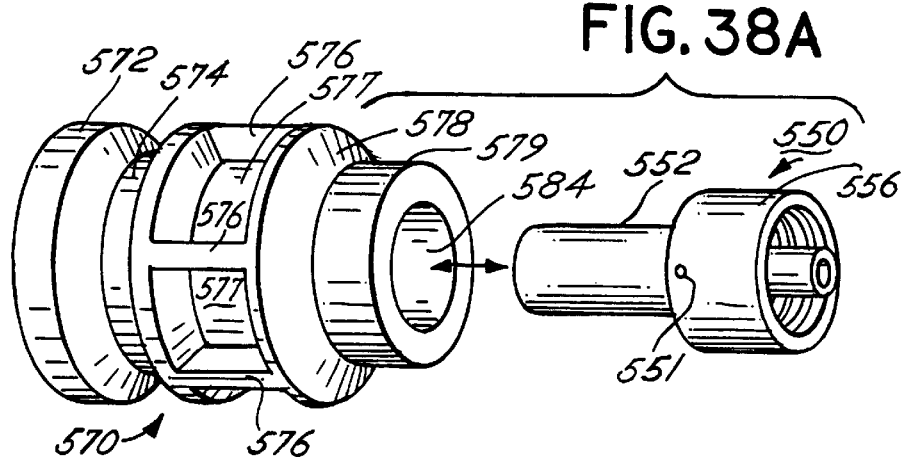
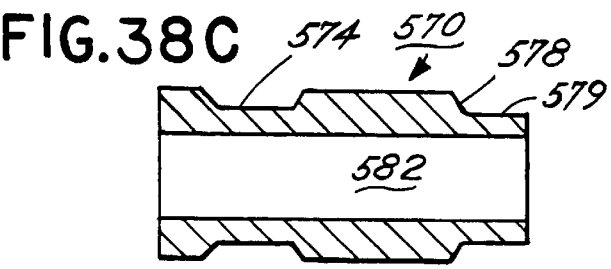
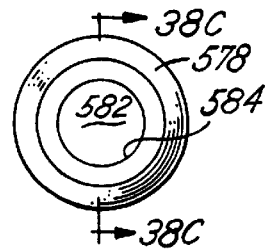

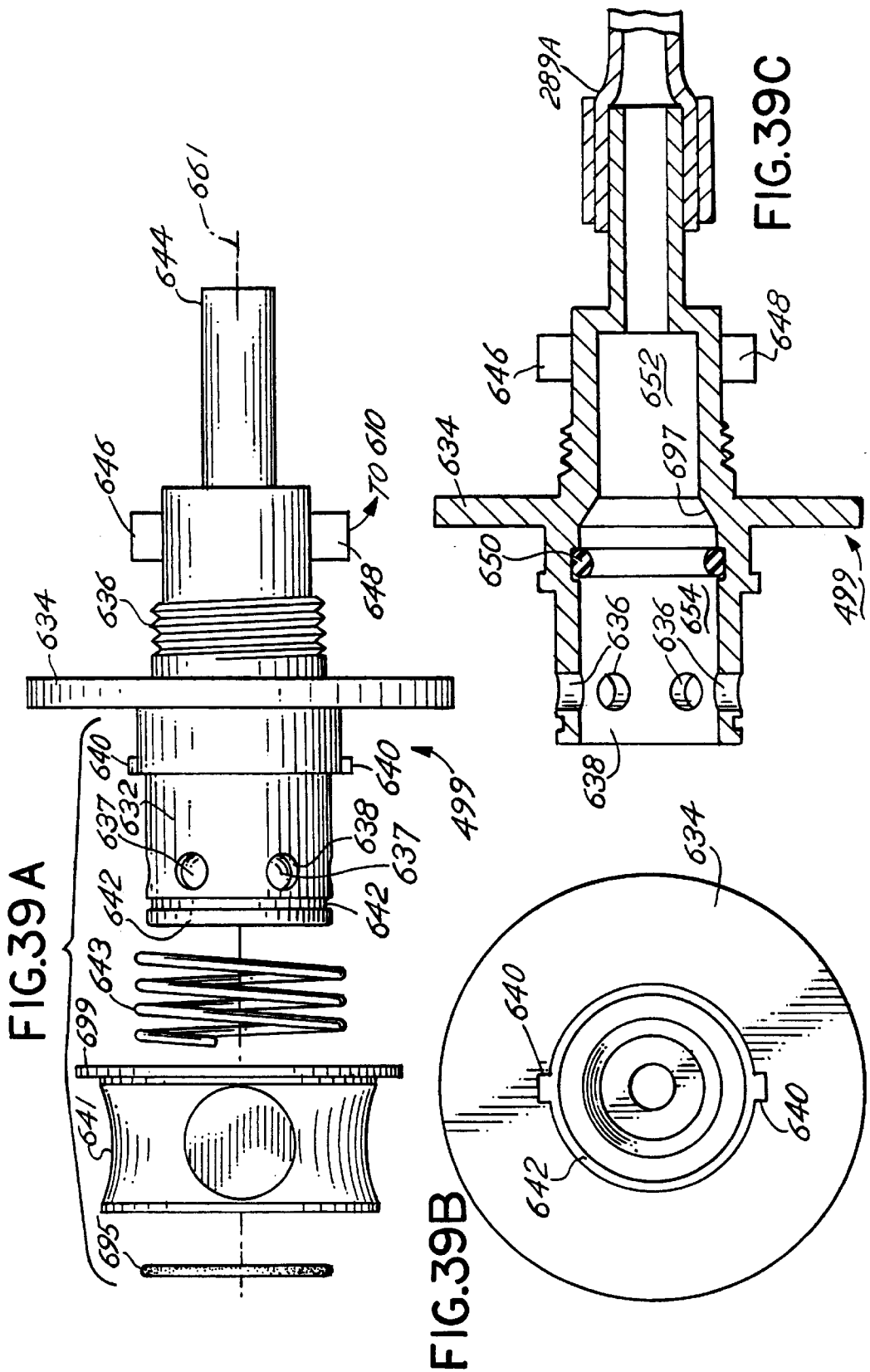

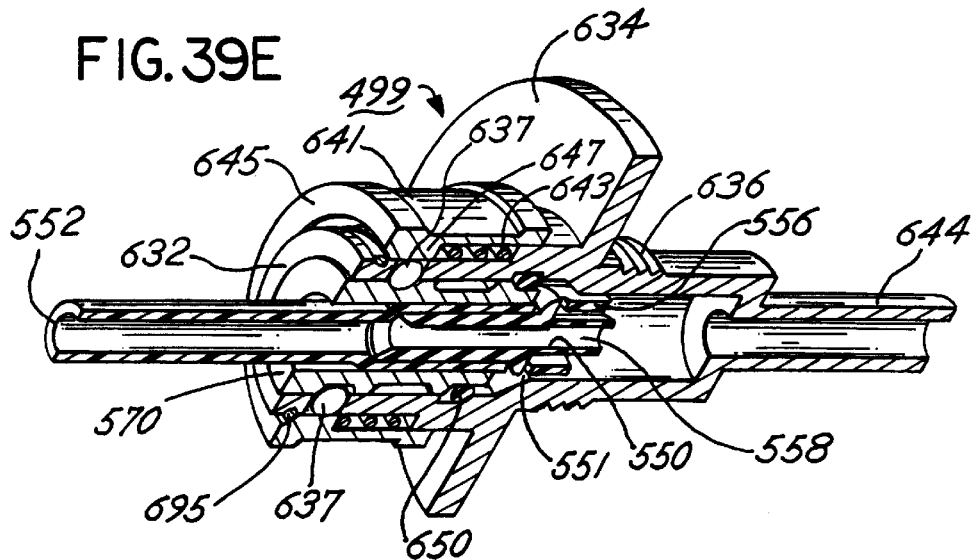
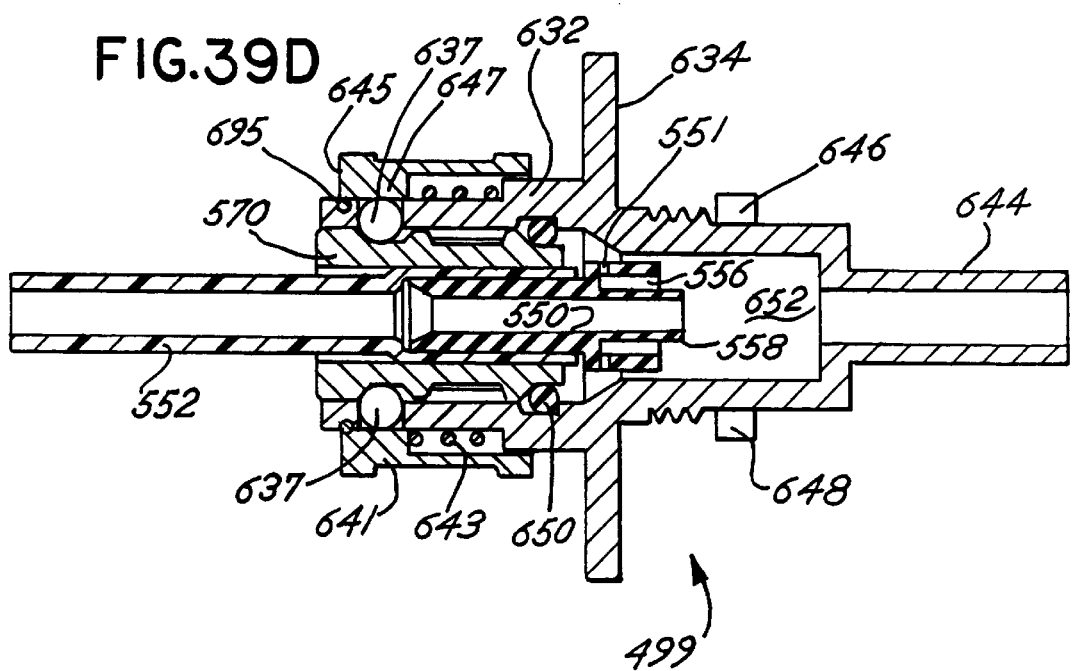

HEMODIALYSIS MACHINE WITH AUTOMATIC PRIMING BY INDUCED PRESSURE PULSES

This is a divisional of application Ser. No. 08/560,439 filed Nov. 17, 1995, now U.S. Pat. No. 5,702,606, which is a division of application Ser. No. 08/388,275 filed Feb. 13, 1993, now U.S. Pat. No. 5,591,344.

NOTICE RE: COPYRIGHT

A portion of the disclosure of this patent document contains matter subject to copyright protection. The copyright owner has no objection to the facsimile reproduction by anyone of the patent disclosure, as it appears in the Patent and Trademark Office files and records, but otherwise retains all copyright rights whatsoever.

FIELD OF THE INVENTION

The invention relates to dialysis machines, their constituent components and subsystems, and their methods of operation. The dialysis machine of the present invention is particularly suitable for use outside of a conventional dialysis clinic, e.g., in a home, self-care clinic, or nursing home environment.

BACKGROUND OF THE INVENTION

Dialysis, including hemodialysis and peritoneal dialysis, is a treatment mode for patients that suffer from inadequate kidney function. In hemodialysis, blood is pumped from the patient's body through an extracorporeal artificial kidney (dialyzer) circuit, where blood-borne toxins and excess water are filtered out of the blood through a semipermeable membrane into an electrolyte (dialysate) medium. A commonly used form of dialyzer comprises a large number of semipermeable hollow fiber membranes, which greatly increase the surface area available for dialysis to facilitate diffusion and convection across the membranes.

Existing dialysis systems typically consist of two parts; one comprising an extracorporeal blood flow circuit and the other comprising a dialysate circuit or flow path. Typically, the entire blood flow circuit is disposable and comprises: 1) an arterial and venous fistula needle, 2) an arterial (inflow) and venous (outflow) tubing set, 3) a dialyzer, 4) physiologic priming solution (saline) with infusion set, and 5) an anticoagulant, such as heparin or sodium citrate with infusion set. The arterial needle accesses blood from the patient's blood access site and is connected to the arterial blood tubing set, which conveys blood to the dialyzer.

The arterial line typically comprises: a pumping segment with interfaces to a rotary or peristaltic blood pump on the hemodialysis machine, pressure monitoring chambers including tubing which interfaces to pressure transducers on the machine to monitor the pressure pre-pump and/or post pump, inlet ports for saline and anticoagulant, and one or more injection sites for drawing blood or injecting drugs.

The dialyzer itself typically comprises a case which encloses a bundle of hollow fibers having a semi-permeable membrane. The blood is circulated on the inside of the hollow fibers while dialysis solution is circulated on the outside, so that the two never come into direct contact. Toxins diffuse out of the blood and into the dialysis solution owing to the concentration gradient. Excess water in the patient's blood enters the dialysate as a result of a pressure gradient. The membrane is made from cellulosic derivatives or synthetic polymers.

The venous line and needle carry the newly dialyzed blood away from the dialyzer and back into the patient's circulatory system. The venous set is comprised of a pressure monitoring chamber with tubing leading to another pressure transducer in the machine, injection sites, and a segment of tubing which interfaces to an air detection assembly in the machine in order to prevent air emboli from passing to the patient.

Dialysis solution is typically prepared continuously on-line in present-day machines by combining water which has first been purified by a separate water treatment system and liquid concentrates of electrolytes. Over the past decade the dialysate concentrates have evolved from a single formulation which contained acetate as the physiologic buffering agent for the correction of circulatory acidosis, to two containers where bicarbonate replaces acetate as the buffering agent. Two proportioning pumps are required, the first to mix the bicarbonate concentrate with water and the second to proportion this mixture with the concentrated electrolytes to achieve the final, physiologically compatible solution.

Most contemporary hemodialysis machines continuously monitor the pressure at the blood outlet side of the dialyzer by way of the pressure transducers connected to the blood sets and also in the dialysate circuit. Microprocessors calculate an estimated transmembrane pressure (TMP) which correlates to the amount of water transmission through the membrane. These machines may also have means of measuring the amount of dialysis solution entering and leaving the dialyzer, which allows the calculation of net water removal by ultrafiltration from the patient. By electronically comparing the amount of water entering or leaving the blood with the transmembrane pressure, the system is able to control actively the water removed from the patient to a desired target previously programmed into the system. When low-water-transmission cellulosic membranes are employed, negative pressure must be generated on the dialysate side of the membrane by the machine in order to accomplish sufficient water removal. Because suction may be applied to the dialysate as it transits the dialyzer, it must first be placed under a greater vacuum in a degassing chamber so that air bubbles are not generated within the dialyzer that would cause errors in the calculation of ultrafiltration by the sensors and also reduce the efficiency of the dialyzer. On the other hand, when high-water-transmission, synthetic membranes are used, it is frequently necessary to apply positive pressure on the dialysate side to control the otherwise excessive rate of ultrafiltration.

The majority of dialyzers are reused in the United States. The trend worldwide is towards reusing dialyzers. There are numerous procedures for reusing dialyzers both manually and automatically. In centers, special machines for simultaneous multiple dialyzer reprocessing are used.

These procedures must be conducted in a biohazard environment since there is always the potential for exposure to human blood, and hepatitis and AIDS are relatively prevalent in the dialysis population. Also, the OSHA and EPA stipulate various working environment regulations owing to the hazardous sterilizants and cleaning agents used.

Reprocessing of dialyzers and lines may be performed on the dialysis machine. The Boag patent, U.S. Pat. No. 4,695,385, discloses a cleaning apparatus for dialyzer and lines. The device is permanently or semipermanently connected into the dialysis machine system.

Finally, the dialysis machine fluid circuits must be periodically cleaned and disinfected. There are two reasons for this. The first relates to the fact that the dialysate has historically not been sterile. From the very beginning of dialysis as a therapy, the dialyzer membrane has been relied upon to be a sterile barrier between dialysate and blood. This is certainly true for whole bacteria, but concern has been growing over the past several years that with the use of synthetic membranes and their more porous structure, endotoxins, or components thereof, may by permeating these membranes and activating inflammatory processes within the patients. When dialysate containing bicarbonate is used, calcium carbonate inevitably precipitats and accumulates on the plumbing and must be dissolved with an acidic solution.

Historically, many artificial kidneys have utilized a proportioning system for producing dialysis solution and delivering it into a hemodialyzer. In the early years of hemodialysis only a so-called tank or batch system was used. The machine was provided with a large tank where purified water was premixed with dry chemicals to make dialysis solution, which was warmed and recirculated through the dialyzer dialysate path. Bicarbonate was used as a buffer; $CO_2$ was bubbled through the solution, or lactic acid was added to the solution to prevent calcium/magnesium carbonate precipitation. With inefficient dialyzers, a dialysis time of 12 hours or more was used. Warm dialysate was an excellent culture medium for bacterial growth. Long dialysis treatment time magnified the problem. To overcome this problem a proportioning system was designed whereby the solution was being prepared ex tempore from purified water and concentrate. The concentrate contained acetate as the physiologic buffering agent because bicarbonate tended to precipitate with calcium and magnesium if present in the same concentrate.

As of the mid-1990's there are approximately 180,000 patients on dialysis in the United States, almost 500,000 worldwide. Most of them dialyze in hemodialysis centers and approximately 17% are on home peritoneal dialysis with less than 3% on home hemodialysis. Typically, in-center hemodialysis is performed three times per week for between two and four hours. The more physiologically desirable four times per week dialysis sessions are used only with patients with severe intolerance to three times weekly dialysis, generally due to cardiovascular instability. Home hemodialysis is also typically performed three times weekly.

Three dialysis sessions per week is considered a standard schedule in the majority of dialysis centers, yet there is considerable scientific evidence that more frequent dialysis for shorter periods of time is more beneficial. Whereas the normal human kidneys function continuously to produce gradual changes in total body fluid volume and metabolic waste levels, three times weekly dialysis schedules produce abnormal physiological fluctuations which yield considerable stress on the patient's systems.

The amount of time consumed travelling to and from the center, and the dialysis procedure itself, is mostly tolerable for the patients who perform three sessions per week. Consequently, only those patients who experience unbearable intolerance of body fluid volume fluctuations, and the associated symptoms, agree to more frequent (four times weekly) dialysis sessions. For home dialysis patients, more frequent dialysis than three times per week would mean more stress on the relatives who help with set-up and who monitor the patient and on the patient who does most of the work for set-up, tear-down, and cleaning. Accordingly, the use of home hemodialysis on a frequent basis (four or more times per week) has, at least heretofore, not been widely practiced.

Many patients have enormous difficulties achieving a "dry" body weight if they accumulate three, four, or more kilograms of fluid between dialysis treatments. Some patients, especially those with heart disease, poorly tolerate even a two kilogram fluid weight gain; they are short of breath before dialysis, have muscle cramps and hypotension during dialysis, and feel "washed out" and are extremely weak, needing several hours to "equilibrate" and become functional. Serum concentration of highly toxic potassium frequently reaches dangerous levels (more than seven mEq/L), particularly preceding the first dialysis after a longer interval (weekend). To mention only a few others, calcium and pH are too low before dialysis or too high after dialysis in many patients. Empirically, in many hemodialysis units, these patients are placed on a four times weekly dialysis schedule.

Historically, artificial kidney systems were developed according to the assumption that the machine should be very sophisticated and automated during dialysis and less so for preparation and cleansing. This assumption was valid for long and infrequent dialysis sessions where compared to the total dialysis time the time for setup and cleansing of the machines was relatively short.

More efficient dialyzers were eventually designed, and time of a single dialysis session gradually decreased to 8, 6, 5, 4, 3, and even 2 hours. With very efficient dialyzers, acetate was delivered to the patient in excess of the body ability to metabolize it, which caused cardiovascular instability. An answer to this problem was to return to bicarbonate as a buffer but within an overall design of proportioning system. Because of chemical incompatibility of bicarbonate with calcium and magnesium, two proportioning pumps are required, the first to mix the bicarbonate concentrate with water and the second to proportion this mixture with the concentrated electrolytes to achieve the final, chemically compatible solution. However, a short daily dialysis session of 1–3 hours offers a possibility of abandoning the proportioning system.

If short daily hemodialysis is done in a dialysis clinic, the travel time, inconvenience and expense incurred by the patient increases dramatically. If such a practice is adopted by a large number of the center's patients, the staff at the treatment center is also burdened. Additionally, the dialysis facility's capacity for performing this number of incremental treatments would have to be increased, requiring capital expansion. Consequently, the patient's home is a desirable location for this treatment modality.

U.S. Pat. No. 5,336,165 to Twardowski describes techniques for overcoming many of the problems associated with conventional dialysis devices. This patent describes a hemodialysis system which has a built-in water treatment system; automatic formulation of batch dialysis solution; automated reuse; automated set-up; automated cleaning and disinfection of blood and dialysate circuits; and reduction in storage space by utilizing dry and concentrated chemical reagents. This system is suitable for home dialysis.

The failure of home hemodialysis to achieve the widespread popularity is due partly to the failure in the art to produce a user-friendly, efficient, and affordable home hemodialysis system that relieves the patient and the patient's family from time-consuming and tedious pretreatment and post-treatment set-up and teardown of the home hemodialysis equipment. The present inventive machine remedies this situation, offering patients a hemodialysis system particularly suitable for short daily hemodialysis in the home environment.

The present invention relates to a modular hemodialysis machine especially suitable for use in the home environment that provides for a cost-effective, transportable, simple and highly reliable home hemodialysis system that automates substantially the entire process and requires a minimum of patient input and labor. By substantially reducing the labor intensity and disposables cost associated with prior art home hemodialysis treatment equipment, the present invention is intended to open up the availability of short daily hemodialysis in the home environment to a larger pool of hemodialysis patients. These patients, by practicing the present invention, can avail themselves of this treatment modality, which has proven to yield outstanding clinical benefits, without having the inconvenience of travel to remote treatment centers.

SUMMARY OF THE INVENTION

A hemodialysis machine is described that features automatic priming of a dialyzer membrane. The hemodialysis machine includes a dialyzer having a blood side thereof and a dialysate side thereof, the dialyzer membrane separating the blood and dialysate sides of the dialyzer. A dialysate circuit is provided for circulating dialysate solution to the dialysate side of the dialyzer. An extracorporeal circuit having arterial and venous blood lines connecting a patient to the dialyzer is also provided. A means is provided for introducing a priming fluid into the arterial and venous lines and for filling the arterial and venous lines and the blood side of said dialyzer with the fluid. The priming fluid could be saline solution from a saline bag, a physiologic dialysate solution from the dialysate circuit, or the patient's blood. A blood pump in the extracorporeal circuit is provided for pumping fluids in the arterial and venous lines. First and second clamps clamping the arterial and venous blood lines, respectively, are also provided.

The hemodialysis machine system includes a control system operative of the first and second clamps and the blood pump to achieve the automatic priming of the dialyzer. The blood pump and clamps are operated to induce multiple brief pressure pulses in the fluid filling the extracorporeal circuit. The pressure pulses have the effect of shearing off air bubbles from the blood side of said membrane. The control system and blood pump are operative to remove the air bubbles from said blood side of the dialyzer membrane and out of said extracorporeal circuit, such as by passing the fluid with the air bubbles entrained therein to a bubble trap downstream of the dialyzer where they are removed from the fluid in conventional fashion.

In a preferred implementation, the hemodialysis machine further comprises a dialysate pump, with the control system further operative of the dialysate pump to force fluid in the dialysate circuit through the membrane from the dialysate side thereof into the blood side thereof in synchrony with the induced multiple brief pressure pulses in the priming fluid filling the extracorporeal circuit. The backflushing of the dialyzer membrane in synchrony with the pressure pulses further assists in removal of the air bubbles from the dialyzer membrane These and other features of the invention will be described below in conjunction with a presently preferred embodiment of the hemodialysis machine.

BRIEF DESCRIPTION OF THE DRAWINGS

In the following detailed description of the presently preferred embodiments of the invention, reference will be made to the accompanying drawings, wherein like numerals in the drawings refer to like elements in the various views, and wherein:

FIG. 1 is a schematic block diagram of the overall system, showing the relationship between a water pretreatment module, a modular home dialysis machine and the patient;

FIG. 2 is a detailed schematic diagram of the water pretreatment module of FIG. 1;

FIG. 3A is a perspective view of the water filtration unit 40 of FIG. 2, showing the path of water through the water filtration unit;

FIG. 3B is a perspective view of the secondary water filtration unit 84 of the water treatment module 24, showing the flow of water through one half of the unit;

FIG. 4A is a cross-sectional view of the pressure relief valve 78 with integral sample removal port of FIG. 2;

FIG. 4B is a detailed view of the upper portion of the pressure relief valve 78 of FIG. 4A during removal of a sample from the valve;

FIG. 4C is a perspective view of an alternative construction for the central member 146 of FIG. 4A;

FIG. 4D is a persecutive view of the insert of FIG. 4A;

FIG. 5 is a detailed schematic diagram of the water treatment module 24 of FIG. 1;

FIGS. 7A–7C are several views of the chemical loading platform 250 of FIG. 6;

FIG. 7D is a sectional view of the loading platform of FIG. 7A along the lines 7D of FIG. 7B, showing the sprayer inserted within the housing; FIG. 7E is an end view of the loading platform of FIG. 7A; FIG. 7F is a horizontal cross sectional view of the loading platform of FIG. 7A taken along the lines 7F of FIG. 7E;

FIGS. 8A–8C are several views of the chemical applicator system 260 of FIG. 6;

FIGS. 9A–9C are several views of the mounting member 354 of the chemical applicator 260 of FIGS. 8A–8C;

FIG. 11A is a plan view of the noninvasive conductivity cell 218 of FIG. 6, FIG. 11B is a plan view of an alternative noninvasive conductivity cell 218;

FIGS. 15A–15D are several views of a cassette-style debubbler for use in the extracorporeal circuit module 28 of FIG. 13;

FIG. 20 is a flow diagram of the sequence of events during the initiate dialysis step of FIG. 17;

FIG. 21 is a flow diagram of the sequence of events during the dialyze step of FIG. 17, showing in particular the periodic backflush of the dialyzer 404 during dialysis;

FIG. 22 is a flow diagram of the sequence of events during the rinseback step of FIG. 17;

FIG. 23 is a flow diagram of the sequence of events during the clean and rinse step of FIG. 17;

FIGS. 24A–24B are two views of a technique for securing silicone tubing such as that used in the present invention to a hardware component, such as, for example, a pump or valve;

FIG. 26 is a diagram of conductivity as a function of time measured by the conductivity sensors 218 and 426 during the clearance test 743 of FIG. 19;

FIGS. 28–33C are tables of the state of the components of the machine 22 of FIG. 1 during the modes of operation of the machine illustrated in FIGS. 18–23;

FIGS. 34–35B are tables of the state of the alarms of the machine 22 of FIG. 1 during the modes of operation of the machine illustrated in FIGS. 18–23;

FIGS. 37A–7C are several views of a male luer 550 of a tubing connection terminal for use with the disinfection manifold of FIG. 36;

FIG. 38A is a perspective view of the male luer 550 of FIG. 37 shown prior to insertion of an outer piece 570 thereover, the male luer and outer pieces forming a unitary tubing connector;

FIGS. 38B–38C are several view of the outer piece 570 of FIG. 38A;

FIGS. 39A–39C are several views of preferred design for the ports of the disinfection manifold 494 of FIGS. 13 and 36;

FIG. 39D is a sectional view of the port of FIG. 39C with the tubing connector of FIG. 38D installed therein;

FIG. 39E is a perspective view of the construction of FIG. 39D partially broken away;

DETAILED DESCRIPTION AND BEST MODE OF PRACTICING THE INVENTION

Figure 6:
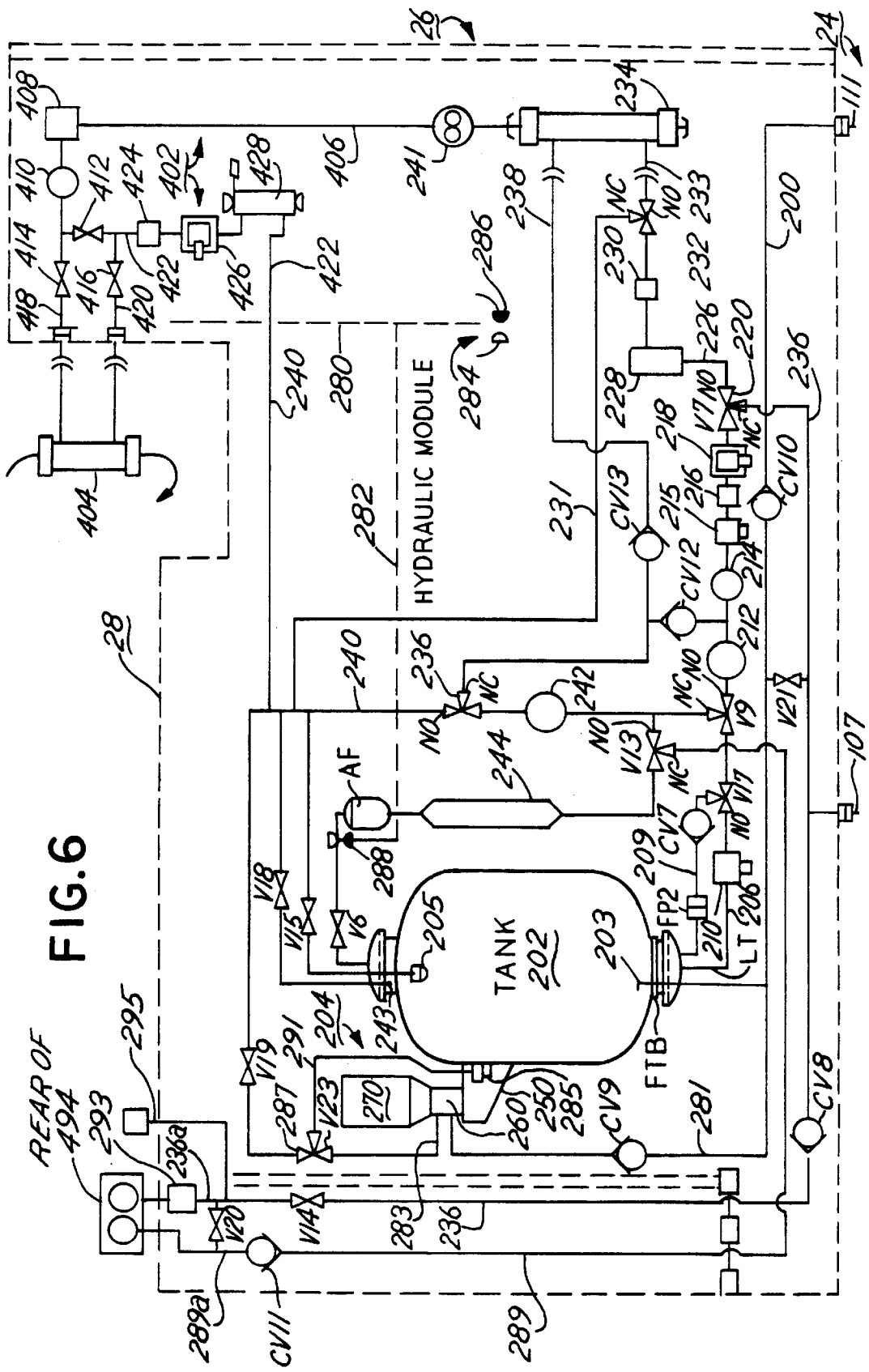
FIG. 6 is a detailed schematic diagram of the hydraulic or dialysate preparation module 26 of FIG. 1.

Referring to FIG. 1, a preferred embodiment of the overall inventive machine and system is shown in block diagram form. The modular dialysis machine 22 receives water from a water pretreatment module 20. The pretreatment module 20 and modular dialysis machine 22 are shown installed, for purposes of example and not limitation, in a patient's home environment. The primary functions of the water pretreatment module 20 are to provide preliminary treatment of water from a household water supply, to provide treated water at a predetermined warmed temperature and pressure to the dialysis machine 22, and to carry system drain and waste water from the dialysis machine 22 to a household drain. The dialysis machine 22 is a preferably a moveable unit, mounted on wheels, that houses three functionally discrete modules: a water treatment module 24, a dialysate preparation or hydraulic module 26 and an extracorporeal circuit module 28. The patient in need of dialysis (not shown) is connected to the extracorporeal circuit module 28 in conventional fashion with two lines designated "arterial" and "venous".

The dialysis machine 22 further includes a patient interface and control module 25 including a display and a touch screen (or other patient input means, such as a keyboard) connected to one or more central processing units. The interface and control module 25 exercises supervisory control over the operation of the system, displays the current status of the machine, prompts the user to input commands and information, receives data from the various sensors and other passive components of the system, records the data in memory, controls the operation of the active components of the machine (such as valves, pumps, heaters, etc.), alerts the patient to abnormal or failure conditions in the machine with alarms or other indicators, calculates parameters relating the hemodialysis, and performs additional tasks as discussed in detail below. Additionally, the interface and control module 25 may be provided with additional hardware components to permit the machine 22 to send patient dialysis informat ion to a central monitoring station electronically, such as by modem.

I. Water Pretreatment Module 20

Referring now to FIGS. 1 and 2, the water pretreatment module 20 is shown installed in a cabinet 32 under a sink 34 (FIG. 1). The water pretreatment module 20 could also be a mobile unit, in which flexible lines connect the module 20 to the household hot and cold water pipes. Referring in particular to FIG. 2, hot and cold water is tapped off a household water system and fed to a temperature-controlled mixing valve 36, where the water is mixed to maintain a constant temperature of 28 to 30 degrees C. in the output line 37. A suitable temperature-controlled mixing valve is available from Grohe, part no. 34 448. The warm water is passed through a water pressure regulator 38 past a manually operated valve 39 to a replaceable integral water filtration and treatment unit 40. A preferred pressure regulator 38 can be obtained from Norgren.

A preferred water treatment unit 40 is the ROPAK unit from Millipore, part no. MSPB00168. Referring to FIG. 3A, the water treatment unit 40 has a unitary housing 47 containing four chambers 49A–49D. The water enters the chamber 49A via water inlet 41A. Chamber 49A is loaded with a particle filtration agent 42 that filters the water for particulate matter. After passing through the particulate agent 42, the water is passed through a second chamber 49B and a third chamber 49C loaded with a carbon filtration agent 44 which removes organic material and dissolved gasses from the water. The water then passes into a fourth chamber 49D containing a polyphosphate water softening agent 43 and passes through the polyphosphate water softening agent and out the outlet 45A.

Water is sent out of the water filtration unit 40 in line 46 and sent to a pressure relief valve 78 with an integral port for manual removal of samples of water to test for the presence of chlorine or chloramines in the water in the line 46. An outlet 50 directs the flow of water from the water pretreatment module 20 to a water inlet 52 in the dialysis machine 22 via a flexible hose 54. The water pretreatment module 20 has a drain inlet 56 that receives waste water from the dialysis machine 22 via flexible hose 58, and sends such waste water through a drain line 62, past check valve CV3 to a household drain 60. It may be advisable to switch input and output hoses 54, 58 periodically to avoid buildup of any organic matter in the input hose 54, which might occur since the water going to the machine normally contains no chlorine.

Figure 5:
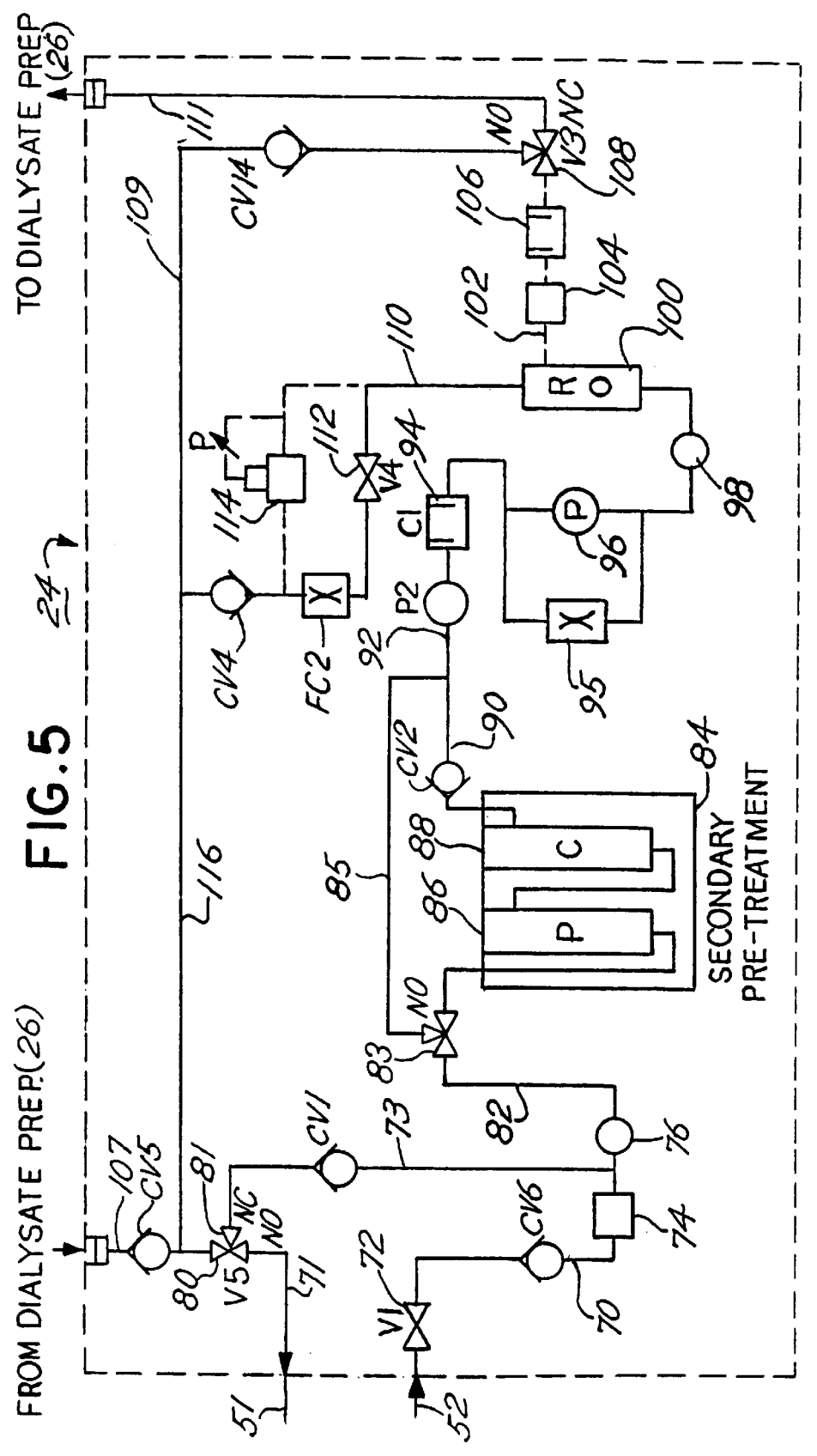

The provision of a temperature-controlled mixing valve 36 to mix household hot and cold water offers numerous advantages. The water temperature that is input into the dialysis machine 22 at inlet port 52 is controlled and maintained at a constant temperature (ideally 28 to 30 degrees C.). This decreases the power consumption of the machine 22, since the machine 22 heating load is minimized, as the machine 22 does not have to heat up cold water. Further, the temperature-controlled mixing valve 36 supplies water into the water treatment module 24 close to the temperature at which the reverse osmosis filter 100 (FIG. 5) membrane is most efficient. This maximizes the throughput of water into the machine 22, thereby reducing water consumption. It should be noted that the temperature-controlled mixing valve 36 could be installed in the inlet circuit of the water treatment module 24 in the event that a water pretreatment module 20 is not used, for whatever reason, with the benefits still obtained.

The pressure regulator 38 further supplies water to the dialysis machine 22 at a substantially constant pressure. A pressure relief valve 78 with integral water sample removal port provides a means for permitting the removal of water from the line 46 downstream of the water treatment unit 40 and to thereby allow for testing of a water sample for the presence of chlorine or chloramines in the water. The sample port allows a fluid sample to be taken from the fluid flow path (i.e., water in line 46) without contaminating the sample. The sample is taken with a syringe or other suitable implement.

The pressure relief valve 78 with integral sample removal port 138 is shown in a cross-section in FIG. 4A. The valve 78 consists of a standard adjustable pressure relief valve housing having an adjustment member 130 which screws clockwise or counterclockwise relative to housing 133, thereby adjusting the force that the pressure relief spring 144 applies to the plastic plunger 142 and elastomeric diaphragm 140. The elastomeric diaphragm 140 provides a lower boundary to an upper chamber 131. The relief valve housing member 132 has a fluid inlet tube 134 and a fluid outlet tube 136. An integral sample removal port 138 is provided at the base of the housing 132.

A cylindrical member 146 is placed within the principal fluid passage chamber 137 with the top rim 139 normally flush against the bottom of the diaphragm 140, thereby preventing entry of fluid over the rim and into the cylindrical member 146 and out the sample removal port 138 under normal pressure conditions in the unit 78. Preferably, the cylindrical member is integrally formed with the housing 132 of the pressure relief valve. In the alternative construction of FIG. 4C, the cylindrical member 146 is shown as a separate piece and is threaded onto the base of the housing 132 just above the sample removal port 138.

A cylindrical plastic insert 148 with a lower tip 152 and an upper surface 154 is placed within the cylindrical member 146. The insert 148 is shown isolated in perspective view in FIG. 4D. The purpose of the insert 148 is to transmit forces from the tip of a syringe 135 inserted into the sample removal port against the base of the diaphragm 140 to lift the diaphragm above the rim 139 of the cylindrical member 146, thereby allowing fluid to escape over the rim 139 down into the sample removal port 138.

FIG. 4B is a detailed view of the upper portion of the chamber 137 when the insert 148 is pushed by the tip of the syringe 135 into an upper position. Referring to FIGS. 4A and 4B, when the user wishes to remove a sample, the user inserts the tip 150 of a syringe 135 into the sample removal port 138. The tip 150 of the syringe 135 pushes against the bottom tip 152 of the cylindrical insert 148, causing the upper portion 154 to push the diaphragm 140 upwards (FIG. 4B). Fluid in the chamber 137 now flows over the rim 139 into the interior region of the cylindrical member 146 (see arrows) and down into the region 156 surrounding the insert 148 and into the sample removal port 138, from where it is pulled into the syringe 135.

Chlorine and chloramines have a high level of toxicity to hemodialysis patients, hence their removal from the water used in the dialysate is imperative. The carbon filter agent 44 of water filtration unit 40 removes such substances from the water line, but in the event that the carbon filter agent 44 has exhausted its capacity to remove chloramines or chlorine, the user will need to replace the water filtration unit 40. After each use of the machine, the user inserts a syringe into the sample removal port, withdraws a sample of the water, and applies the sample to a chloramines or chlorine reagent test strip to see if a color change in test strip occurs, indicating that chlorine substances are in the sample. A preferred source for the test strips is Serim Research Corporation, P.O. Box 4002, Elkhart, Ind. 46514-0002.

The presence of chlorine or chloramines in a household water supply is ordinarily attributable to municipal water treatment efforts. If the carbon filter agent 44 of the water pre-treatment unit 40 is working properly, the chloramine level in line 46 is normally zero. However, if the carbon filter 44 is exhausted, the secondary carbon filter 88 in water treatment module 24 (FIG. 5) removes the chloramines from the water, insuring safety of the system. Ideally, the user checks for chloramines daily after each dialysis treatment, thereby insuring that in the case that the primary chloramine filter agent (e.g., filter 44) is exhausted, the backup secondary carbon filter 88 does not also become exhausted.

Thus, the present invention provides a method for treating water used for the preparation of a dialysate solution in a dialysis machine, comprising the steps of passing water through a first filter (e.g., carbon filter 44) having chlorine removal properties and passing filtered water into a line, removing water from the line and periodically sampling the removed water for the presence of chlorine or chloramines, the presence of chlorine or chloramines indicating that the filtration capacity for chlorine of the first filter is substantially exhausted, filtering the water downstream from the sample location in a second filter (e.g., carbon filter 88) also having chlorine removal properties, and replacing the first filter if chlorine or chloramines detected during the sampling step.

If the user does not use a water pretreatment module 20 and relies on a single filtration and treatment unit in the water treatment module 24, the water filtration unit 40 and water filtration unit 84 are designed to be interchangeable, that is, having four chambers and a housing that adapts to the installation requirements in module 20 and 24. In the event that a single water filtration unit 40 only is used (no pretreatment, as in the case where the patient is traveling with the machine 22 but not the treatment module 20), the unit 40 is placed in the location of the secondary filter 84. The extra carbon filtration capacity allows the filtration unit 40 to be used for a relatively long time between changes. If the cloramine content of the tap water and the filtration capacity of the carbon filtration agent are known, an estimate of the life expectancy of the filtration unit 40 can be arrived at and the replacement of the unit 40 scheduled accordingly. Further, a sample of reverse-osmosis water may be taken at a sample port in the dialysate preparation module 26 of the machine 22, e.g., at the pressure relief and sample unit 210 (FIG. 6).

II. Water Treatment Module 24

Referring now to FIG. 5, the water treatment module 24 of the dialysis machine 22 will be discussed in detail. The water treatment module 24 includes a water line 70 connected to the water inlet 52 that receives water from the water pretreatment module 20. The flow of water into the water treatment module 24 is controlled by a valve 72 (such as Sirai part no. D111 V14 Z723A) and check valve CV6. A thermistor 74 (10 Kohm from Thermometrics) and pressure transducer 76 (Microswitch part no. 26PC X-98752-PC) monitor the temperature and pressure of the incoming water in the line 72. A check valve CV1 is placed on return line 73.

A three-way valve 80 (such as Sirai part no. 311 V14 Z723A) is provided connecting drain line 71 and inlet line 70 via return line 73. With port 81 in its normally closed (NC) condition as shown in FIG. 5, water is shunted into line 82 where it is passe to a pressure transducer 76, through a bypass valve 83, to the secondary water filtration and treatment unit 84. In the preferred embodiment, the water filtration and treatment unit 84 is of the same basic construction and design as the water filtration and treatment unit 40 of the pretreatment module 20. In particular, the housing for the secondary water filtration and treatment unit 84 is given dimensions such that it can be interchangeably installed in either the water pretreatment module 20 or the water treatment module 24. A suitable unit 84 is the ROPAK from Millipore, part no. CPR0P0402. Referring to FIG. 3B and FIG. 5, the water is first passed through a first chamber 86 (86A in FIG. 3B) containing a particle filter agent 42 and then a second chamber 88 (88A in FIG. 3B) containing a carbon filter agent 44 that removes organic matter and dissolved gasses and any residual chlorine or chloramines in the water. The water then flows through a screen in the chamber 88 and through a polyphosphate water sequestering agent 43.

In the embodiment of FIG. 3B, the chambers 86B and 88B of water filtration and treatment unit 84 are filled with the same filtration agents as chambers 86A and 88A, respectively. In the event that any of filtration agents in chambers 86A and 88A are exhausted, the user simply reconnects the inlet and outlet lines from 41A and 45A to the inlet 41B and outlet 45B. This arrangement makes it relatively easy for the user to remedy the situation of an exhausted filter without having to replace an entire filter assembly, and gives the user time to make arrangements for the delivery of a replacement water treatment unit 40.

The treated water is teen fed on output line 90 past a check valve CV2 to water pressure sensor 92 (same as 76) and to an invasive conductivity cell 94 (such as the Pulsa Feeder part no. E-2A). The conductivity cell 94 measures the ion content of water in the line 90.

A three way bypass valve 83 is provided on line 82 such that, during the disinfection cycle of the machine, hot water bypasses the water filtration and treatment unit 84 to prevent hot water from adversely impacting the integrity of the polyphosphate water softening agent in the treatment unit 84. Polyphosphate water sequestering agents are known to degrade when subjected to water at high temperatures for an extended period of time. The normally closed port NC and normally open port NO of valve 83 allows incoming water from the water pretreatment module 20 to pass through the water filtration and treatment unit 84, but when the condition of these ports is reversed, water is shunted through bypass line 85 to output line 90.

Still referring to FIG. 5, a pump 96 (such as Procon part no. CO16505AFV and Leeson motor no. 101389-1) is located in the line 90 to pump the water past a pressure sensor 98 to a reverse osmosis filter 100 (such as Millipore housing part no. SL1P106M4 and Dow FilmTek XUS 50454.00 filter). A flow restrictor 95 is placed across the pump 96 to avoid deadhead failure conditions. A valve 112, flow constrictor FC2 and check valve CV4 are place in return line 110. An adjustable pressure regulator 114 is placed in parallel with the high pressure valve 112 (Honeywell part no. 71215 SN2 KVOONO D5D1C2). The pressure regulator 114 provides back pressure for the reverse osmosis filter 100 to force water to cross the membrane. High pressure valve 112 bypasses flow to regulator 114 minimizing back pressure in certain operating modes and failure conditions. Flow constrictor FC2 provides about 10 psi back pressure to RO filter 100 during the hot water disinfection, described in detail below. Lines 110 and 116 are drain lines which drain water rejected by the reverse osmosis filter 100 through valve 80 to drain line 71.

Water that passes through the reverse osmosis RO filter 100 is passed through a line 102, past a thermistor 104, past a conductivity cell 106 (same as 94), to a three way valve 108 having a normally open port NO connected via check valve CV14 to drain lines 109 and 116. When the normally closed port NC of valve 108 is open, reverse osmosis water is fed via line 111 to the dialysate preparation module 26 (FIG. 1, 6). This occurs when a comparison of conductivity cells 94 and 106 verifies proper function of reverse osmosis filter 100. If the comparison yields improper function of reverse osmosis filter 100, the water is diverted to drain through the normally open port of valve 108, and lines 109, 116 and 71.

Line 107 and check valve CV5 provide a pathway for the flow of drain fluids and heated water from the dialysate preparation module 26 to the water treatment module 24. Depending on the condition of three-way valve 80, fluids from line 107 are directed through line 71, or line 73. It will be further appreciated that the valve network in water treatment module 24 permits the selective flow of water through every fluid pathway in the module 24, including a bypass of the water filtration and treatment unit 84. Check valve CV5 further prevents water from being passing through the line 107 when rejected water from reverse osmosis filter 110 is returned to drain line 71.

III. Dialysate Preparation (or Hydraulic) Module 26

Figure 10A:
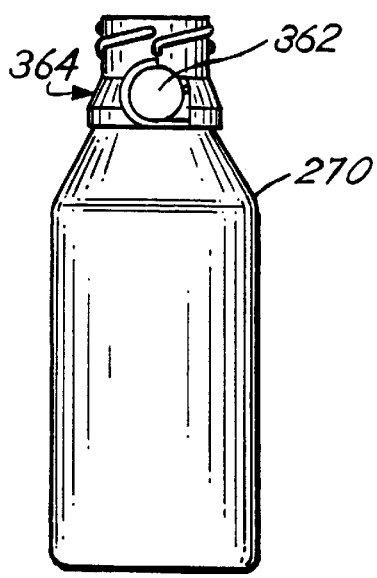
FIGS. 10A–10F are several views of the chemical bottle 270 of FIG. 6.

Referring now to FIG. 6, the dialysate preparation module 26 will be discussed in detail. An overall function of the dialysate preparation module 26 is to automatically mix and prepare the dialysate solutions and deliver the solutions to the dialyzer 404. The dialysate preparation module 26 has an inlet line 200 connected to line 111 (FIG. 5) receiving filtered water from the water treatment module 24 via valve 108 (FIG. 5). The line 200 carries the water past check valve CV10 to a chemical mixing tank 202, preferably constructed from polypropylene. A chemical addition and dispersion subsystem 204 is attached to the side of the tank 202 in fluid communication therewith. The loading platform 250 of chemical addition subsystem 204 is illustrated in FIGS. 7A–7F. The chemical applicator 260 of the chemical addition subsystem 204 is illustrated in FIGS. 8A–8C and 9A–9C. The chemical vessels (ideally bottles) 270 are illustrated in FIGS. 10A–10P.

The addition and dispersion subsystem 204 preferably includes two chemical applicators 260, each for opening a vessel 270 containing an individual batch quantity of dialysis chemicals placed directly above it. One vessel 270 typically contains chemicals in liquid form and the other in powdered form. The batch of chemicals are provided in individual batch vessels, preferably polyethylene and/or polypropylene bottles 270. When the tank 202 is filled with purified water to the proper level, the chemical applicators 260 pierce the bottles 270 from below with a spike, and the chemicals in the bottles fall out of the bottle by gravity into the interior of the loading platform 250. As explained in detail below, a sprayer 285 rinses the chemicals from the loading platform 250 into the tank 202 where the chemicals are dissolved and mixed with water to form the dialysate solution. Additionally, bottle rinsing nozzles are preferably provided within the chemical applicators 260. The nozzles that are disposed below bottles containing dry dialysate chemicals eject water into the bottles in a series of short bursts to gradually flush the chemicals out of the bottles. After the chemicals are dispensed on the loading platform 250, the nozzles flush any remaining chemicals in the bottles 270 from the bottles onto the loading platform 250.

A third chemical applicator 260 and third vessel 270 are also preferably provided above the platform 250. The chemicals in the third vessel will typically either be a salt which can be added to the dialysate solution on demand to adjust the chemistry of the dialysate solution, or else a chemical cleaning or disinfecting agent that is added to the tank during the disinfection cycle. Other possible chemicals for the third bottle 270 are medications, and vitamins and other nutritional supplements. As described below, we prefer to use a hot pure water disinfection process, without chemicals, to clean the fluid circuits of the machine 22. However, if for some reason the hot water disinfection is not sufficient, an alternative mode may be entered whereby the disinfecting chemicals in the third vessel are added to the tank and circulated throughout the machine to achieve cleaning and/or disinfection. Of course, additional chemical applicators and vessels could be added to the top of the loading platform 250, if desired.

The tank inlet tube 203 is placed at the bottom of the tank 202 and oriented tangentially to the walls of the tank 202 in a horizontal plane such that the incoming water is swirled about the side of the tank in the direction of the orientation of the inlet 203 to create a vortex, thereby stirring the water in the tank 202. A spray washer 205 similar to a dishwasher sprayer is provided in the upper region of the tank 202, and is operative during cleaning of the tank 202 and mixing of the dialysate chemicals the tank 202. The force of the water through spray washer 205 causes the spray washer 205 to rotate and spray water into the tank 202 in the same direction as the flow of water in the vortex created by water inlet 203. The cooperation of the spray washer 205 and water inlet 203 create good mixing action in the tank 202, promoting effective dispersion and dissolution of the chemicals that have been introduced into the tank 202 from the loading platform 250, and preventing the settlement of chemicals on the bottom of the tank.

The tank 202 itself is preferably made from a lightweight, biocompatible, chemically compatible, and sterilizable and substantially non-compliant (i.e., rigid and not susceptible to expansion or contraction due to pressure, temperature or other condition) material, that is given the shape shown in FIG. 6. Other shapes are of course possible. We have determined that a tank made from polypropylene with the shell reinforced with fiberglass windings on the outside of the shell meets these requirements for the present dialysis application. The polypropylene is chosen because of its chemical inertness, light weight and ability to be exposed to hot water for long periods without any effect An alternative material for the shell is polyvinylidene fluoride (PVDF). The reinforcing fiberglass threads significantly improve the non-compliance (or stiffness) of the tank 202. As discussed in detail below, non-compliance of the tank is important for improving the accuracy of the ultrafiltration of the patient (i.e., the real-time measurement of fluid removed from the patient during dialysis). The fiberglass threads are wound around the exterior of the walls of the tank 202 in overlapping diagonal layers, with an additional layer wrapping about the mid-section of the tank 202 in a horizontal manner. A suitable tank can be obtained from Structural North America in Ohio. Other possible reinforcing fibers may be suitable, such as composite fibers, carbon fibers and kevlar, which may be integrated into the shell body itself or wound on the outside of the shell.

A pressure transducer LT (Microswitch part no. 26PC X-98493-PC) is provided at the bottom of the tank 202 in line 206 for the purpose of determining the level of water in the tank 202. Line 206 is isolated (static, with no fluid flowing through the line) when the NO port of valve V17 for line 206 is closed and the NC port in line 209 is open, permitting the level transducer to read the level in the tank 202. This would be the case when the tank 202 is being filled. During the filling and mixing of the tank, water is circulated from the line 209 to V17 to V9 through pump 212, valves 220 and 232, line 231 to valve V15, and sprayer 205 in the tank 202, which assists in the mixing of the tank 202.

The tank 202 has a polypropylene mesh filter FTB (130 micron) molded into a flat plate with a polypropylene frame at the bottom of the tank 202. A pump filter FP2 (preferably 50 to 200 microns) is placed on the degassing line 209. Any air or gas which may have been introduced into the dialysate is removed by pumping the dialysate through the filter FP2. The filter FP2 creates a negative pressure which causes entrapped air to come out of the water.

The tank outlet line 206 carries dialysate solution past a pressure relief/sample port 210 to a pump 212. The pressure relief/sample port 210 is a combination pressure relieve valve and integral sample removal port of the same design as pressure relief/sample port 78 (see FIG. 4), and is used to prevent over pressure of the tank 202 and to take fluid sample from the system. When the chemicals are released from the chemical addition subsystem 204 to the tank and are being mixed in the tank 202, the circulation of fluid is though line 206 (with degassing line 209 static).

A three-way valve V17 is placed at the intersection of lines 206 and 209 and determines which line 206, 209 is static. The pump 212 (such as Micropump EG series, 0–3 L/min.) pumps the solution past a pressure transducer 214 (Microswitch PN 26PC X-98752-PC), an integral pressure relief valve with sample removal port 615, and a thermistor 216 to a noninvasive conductivity cell 218 which detcts the concentration of ions in the line 206.

Figure 16:
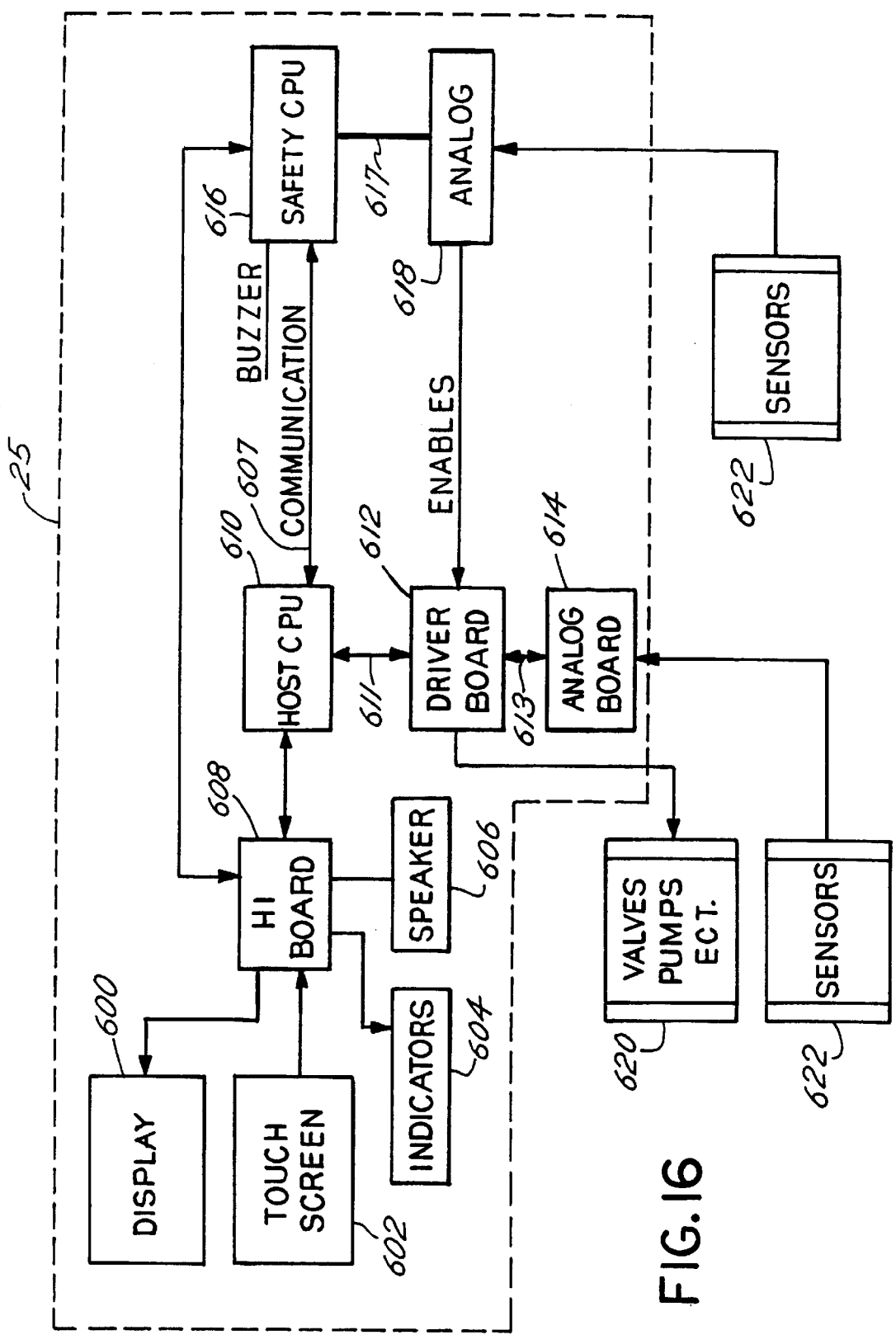
FIG. 16 is a block diagram of the user interface and control module 25 of FIG. 1, showing its relationship to the various sensors and components of the machine.

The noninvasive conductivity cell 218 is illustrated in detail in FIG. 11A. The inlet line 206 is divided into first and second fluid channels 221 and 222 integral with the inlet line 206. The channels 221 and 222 branch in directions 90 degrees from each other. The channels are each oriented at an angle of approximately 135 degrees relative to the inlet line 206. The channels 221, 222 form a rectangular loop with the inlet line 206 and the outlet line 223 at opposite corners. A conductivity measurement sensor (e.g., Great Lakes no. 697 E sensor) 224 with leads 225 is circumferentially disposed about one of the fluid channels 222. The leads 225 from the sensor 224 are fed to the central processing unit 610 or 616 of the user interface and control module 25 (FIG. 16). An alternative construction is shown in FIG. 11B, where channels 221A and 222A are shorter than channels 221 and 222. With either construction, the conductivity cell 218 is preferably installed in a vertical or vertically inclined orientation such that fluid flows upwards through the channels 221 and 222 which prevents the entrapment of air bubbles in the fluid line 222.

The construction of FIG. 11B provides a minimum pathlength to cross-sectional area ratio for the fluid channels 221 and 222. This construction generally maximizes the sensitivity of the sensor 218 and reduce response time.

Referring again to FIG. 6, a three-way valve 220 controls the flow of fluid through output line 226 and return line 236. Water or solution in line 226 is fed to a heater assembly 228. Heater assembly 228 is a temperature controlled, 1300 watt, flow-through heater, such as the Heatron no. 23925 heater. The heater assembly 228 is used for heating dialysate up to body temperature as it is passed to the extracorporeal circuit module 28 (FIG. 1). The heater is also used for heating water up to a disinfection temperature of at least 80 degrees C., and preferably at least 85 degrees C., and maintaining the water at that temperature for more than an hour during the water disinfection of the fluid paths of the machine 22, as discussed in detail below. A thermistor 230 monitors the temperature of the fluids in the line 226. A three-way valve 232 controls the flow of fluid through the tank return line 231 and the output line 233. A dialysate filter such as ultrafilter/pyrogen removal filter 234 is provided for removal of any pyrogenic materials and particulate matter from the dialysate. Suitable filters 234 are the Minntech pyrogen filter and the Fresenius F-80 filter. No dialysate solution goes to the dialysate circuit 402 during dialysis treatment without first passing through the filter 234. The condition of three-way valve 236 controls whether fluid exits from the ultrafilter/pyrogen filter through line 238 or out dialysate circuit input line 406. A flow meter 241 (Xolox part no. 2831F6FF) measures the flow rate of the solutions in line 406.

A check valve CV12 is placed between line 238 and 206. Line 238 and check valve CV 13 allow air to come out of the dialysate side of the ultrafilter 234 (i.e., the outside of the fibers in the filter 234) during the priming of the ultrafilter 234 and pumping of dialysate through the ultrafilter 234 to the dialysate circuit 402.

We have devised a pre-treatment fiber bundle integrity test for the pyrogen/ultrafilter 234. The integrity of the ultrafilter 234 is important to insure that there are no leaks. The pyrogen/ultrafilter is pressurized on the "blood" or dialyzer side (that is, the interior of the fiber bundles in direct fluid communication with the dialyzer 404) of the ultrafilter 234 prior to dialysis, and the rate of pressure decay is measured. A rapid pressure decay, or inability to pressurize the pyrogen/ultrafilter, will cause an alarm to sound, warning the patient of the need to replace the pyrogen/ultrafilter 234. To accomplish this, we first evacuate fluids from the blood side of the pyrogen/ultrafilter 234 by operating the UF pump 242 in the reverse direction to pump air back through the valve 236, through bypass valve 412 in the dialysate circuit 402, through line 406 into the lumen or blood side of the pyrogen/ultrafilter 234. Once water has been evacuated from the blood side of the pyrogen/ultrafilter 234, the blood side starts to pressurize (assuming there are no leaks in the pyrogen/ultrafilter 234). The UF pump 242 pumps until the pyrogen/ultrafilter 234 is pressurized to 500 mm Hg. If there are any leaks, air will leak into the dialysate side of the filter 234. The air pressure is measured with the pressure sensor 410 in the dialysate circuit 402. If pressure sensor 410 never pressurizes, then a severe leak is present. A slow decay in pressure indicates there is no leak. The rate of decay indicative of a leak requiring replacement of the pyrogen/ultrafilter is a function of the physical properties of the filter's membrane, and will accordingly vary depending upon which filter is used. For most filters 234, we expect the threshold decay rate indicative of a failure to be greater than 10–25 mm Hg/30 seconds, depending on the type of filter.

The pressurization of the pyrogen/ultrafilter 234 can also be correlated to the maximum pore size of the filter. As the pyrogen/ultrafilter 234 is pressurized to higher and higher pressures, a maximum pressure will be reached above which the pressure drops suddenly indicating that the surface energy of water in the pores of the filter is less than the force due to the pressure. By knowing the pore size from the maximum pressure, the filtration capacity for certain pyrogens and other materials may be determined.

Referring to FIG. 16, it will be appreciated that the analog board 614 and central processing unit 610 of the central control module receive the pressure data from the pressure sensor 410. Pressure readings indicative of a leak, such as where the ate of decay is greater than a predetermined threshold limit, will cause the CPU 610 (or safety CPU 616) to issue an alarm, such as by issuing a message on the patient interface, or activating the audio or visual indicators 604 or a buzzer.

During the filling of the tank 202, after the chemicals are added, the machine 22 determines when to stop adding water to the tank by monitoring the fluid sensor 288 in the line coming out of the top of the tank 202. When fluid sensor 288 sees fluid, the flow of water is stopped by closing off valve 108 (FIG. 5).

The return flow of old solution (i.e., solution that has passed through the dialyzer) from the dialyzer 404 is though return line 240, valve V18 and dialysate inlet 243. Valves V19, V15 and V6 are closed, directing dialysate through to the dialysate inlet 243.

Figure 13:
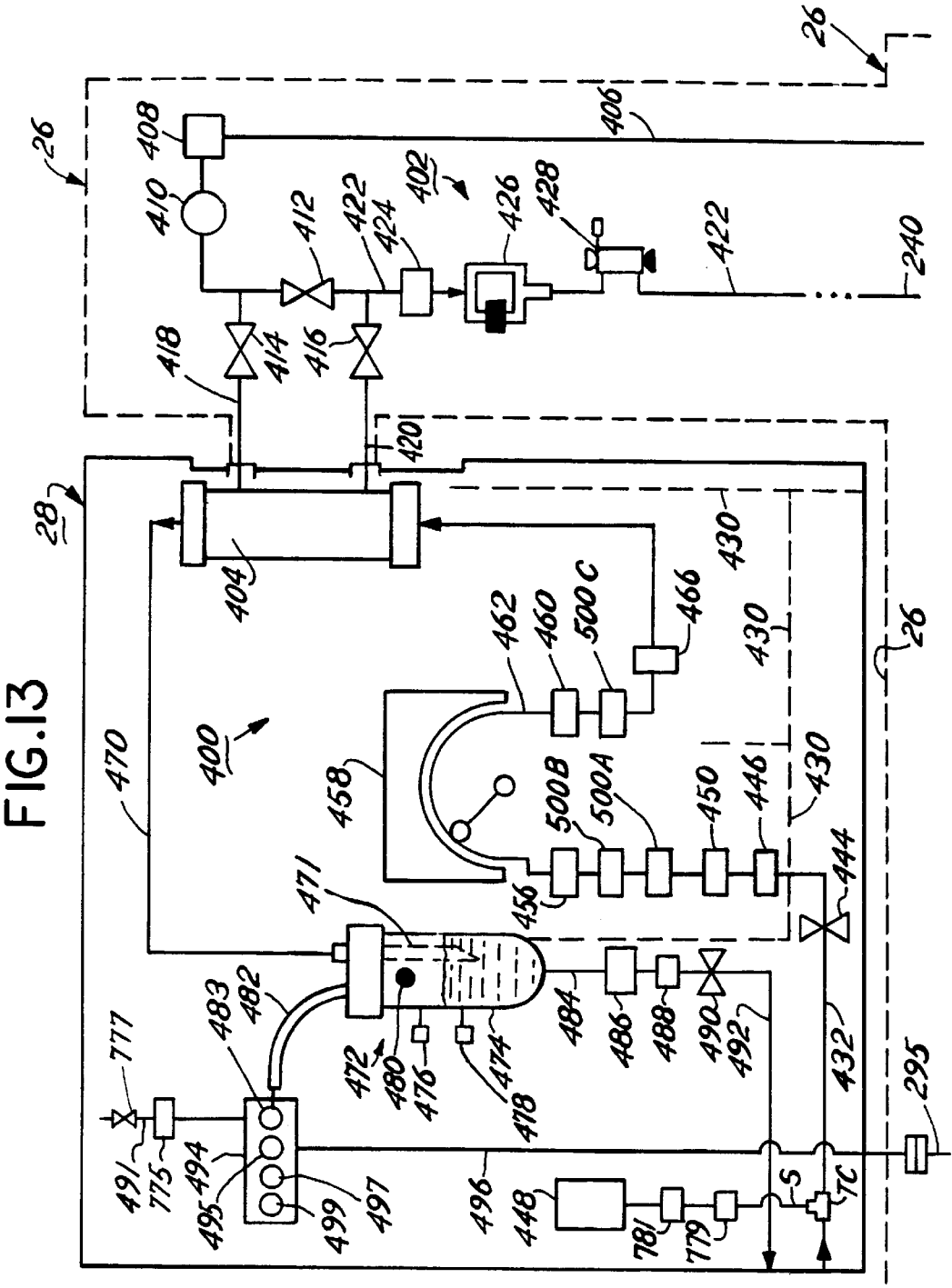
FIG. 13 is a schematic diagram of the extracorporeal circuit module 28 of FIG. 1.

We have invented a technique of maintaining the separation of new and old dialysate in the tank 202 by taking advantage of the differences in density in dialysate when the dialysate is at different temperatures. Our technique is an improvement over the technique described in the Terstegen Patent, U.S. No. Pat. 4,610,782. The preparation and mixing of dialysate in the tank 202 takes place with the dialysate at a temperature of 28 to 30 degrees C. This temperature is controlled, in the preferred embodiment, by the temperature-controlled mixing valve 38 in the water pretreatment module 20. During dialysis, dialysate is heated in the heater 228 to body temperature, generally 37 degrees C., and sent to the dialyzer 404 in the extracorporeal circuit module 28 (FIG. 13). New (i.e., fresh) dialysate is withdrawn from the bottom of the tank 202 and old dialysate is returned at the top of the tank 202 in inlet 243 at a temple of about 37 degrees C., or perhaps a degree or two cooler due to radiative and conductive heat loss in the tubing and hardware in the dialysate circuit 402. The old dialysate is returned to the top of the tank 202 in a manner so as to substantially prevent turbulence of the old dialysate, that is, in a manner to gently introduce the old dialysate into the top of the tank to prevent mixing of the old and new dialysate. We accomplish this by orienting the inlet 243 slightly upward and towards the side walls of the tank 202. The old dialysate forms a zone above the new dialysate with a thermocline boundary layer separating the old and new dialysate due to the temperature differential (and resulting density differential) between the dialysate in the two zone. As the dialysis process continues, the boundary zone migrates down the tank 202 as the volume of fluid in the upper zone of old dialysate increases and the volume of fresh or new dialysate diminishes.

This method works best when the temperature differential between the upper zone and lower zone is at least 5–7 degrees C., or greater, but will work acceptably down to 3 degrees C. Ordinarily, this differential will be present when the dialysate is heated as described.

An improvement to this technique is to heat one to two liters of new dialysate above the temperature of the dialysate in the tank 202 (by preferably at least 5 degrees C.) prior to the initiation of dialysis, and introducing the heated dialysate into the top of the tank in a substantially non-turbulent manner. This sets up the temperature differential zones such that when the old (used) dialysate in introduced into the tank, it enters the upper zone, further minimizing the likelihood of substantial mixing of the old and new dialysate. The heating can be performed by heater 228, and the return of the heated dialysate is through valve 232, return line 231 and valve V18. Valves V6, V15 and the NO ports of valves 236 and 232 should be closed to direct the heated dialysate into the tank 202.

The separation of old and new dialysate in the tank 202 offers a number of advantages. First, it allows a closed loop ultrafiltration control methodology to be used. Second, the fluids being dialyzed from the patents are collected in the tank 202 separate from other solutions, permitting the old dialysate to be sampled, measured, and visually observed in a tank with a window or a sample-removal port. Thirdly, the closed loop ultrafiltration permits the machine to operate, during dialysis, without the machine being connected to a water source and a drain. This gives more mobility to both the machine 22 and the patient, a feature particularly advantageous in the hospital, home and nursing home environments. Fourthly, separation of old and new dialysate improves the efficiency of clearance of uremic toxins for a batch system.

A UF (ultrafiltration) pump 242, connected to the return line 240 through valve 236, pumps dialysate solution to and from the UF tank 244, the direction of flow being a function of whether the UF pump 242 is operated in a forward or reverse direction. NC port of valve V9 is closed and NO port of valve Vie is open providing the pathway for the solution to enter the bottom of the tank 244. The UF pump 242 is also used to pump prime solution from the extracorporeal circuit 400 back to the UF tank 244.

The UF tank level sensor LUF precisely measures the fluid volume in the UF tank 244. The UF tank 244 is used to store fluid removed from the dialysate circuit commensurate with the fluid removed from the patient. The fluid removed from the patient is the difference in the volume of fluid in the UF tank before and after the dialysis of the patient's blood in the dialyzer The rate of fluid removal into the UF tank 244 (and hence total volume when multiplied by time) is controlled by the pump rate of UF pump 242. A sterile barrier air filter AF (such as Pall EMFLON II) open to the atmosphere is installed at the top of the tank 244. Background information on ultrafiltration control in hemodialysis is described in U.S. Pat. Nos. 3,979,284 and 3,939,069 assigned to Rhone-Poulenc (both now expired), which are incorporated by reference herein.

A pressure transducer LUF is mounted at the bottom of the UP tank 244. The transducer LUF measures the pressure and hence level of fluid in the tank 244. The level sensor LUF acts as a safety backup and watchdog for the UF pump 242 to verify the amount of ultrafiltration during dialysis. Specifically, the sensor LUF measures the hydrodynamic pressure of dialysate in the ultrafiltration tank 244 and responsively generates a measurement signal (sent to the control module 25) indicative of the volume of fluid within the UF tank 244. The rate of transport of fluid by UF pump into the UF tank 244 is continuously monitored, such as by knowing the output volume per revolution of the UP pump, and the time elapsed during dialysis. This information allows the central control module 25 (FIG. 16) to determine the expected volume of dialysate in the UF tank 244. By comparing the measurement signal from the sensor LUF with the expected volume of dialysate in the UP tank, the pump rate of pump 242 is verified.

In one possible implementation of this technique, a decision as to the adjustment of the dialysate transport rate into the UF tank (i.e., the pump 242's pump rate) can be made. For example, if sensor LUF indicates that there is 350 ml of fluid in the tank 244 but a calculation of the expected volume of fluid in the UF tank based on pump rate and elapsed time is 385 ml, the pump 242 is pumping about 10% too slow and the pump speed should be increased to meet the ultrafiltration target in the expected dialysis time.

We calibrate the UF pump 242 each time before dialysis commences using the flow meter 241 to insure ultrafiltration control. After the tank 202 and fluid circuits of the dialysate preparation module 26 have been filled with dialysate, positive pressure is created with pump 212 in line 209. Dialysate is conducted from tank 202 through valve V9, through UF pump 242, to valve 236, down through CV12, line 206, valve 220, valve V8 and into pyrogen/ultrafilter 234. The dialysate is sent up through flow meter 241 to the dialysate circuit 402, where the solution goes through bypass valve 412, through return line 422, line 240, valve V18 and back to the tank 202. The pump rate of UF pump 242 can now be calibrated by the control module 25 in the reading of the flowmeter 241. During dialysis, dialysate is pumped from the dialysate circuit into the ultrafiltration tank 244 via line 240, valve 236 and valve Vie in accordance with the target ultrafiltration volume for the patient.

Air and drain paths 282 and 280 are provided in the module 26 for collecting any fluid or overflow from the tank 202. An optical fluid sensor 288 is used to detect when the tank 202 is full during the tank fill mode, to detect failure of valve V6 during dialysis, and to detect a full tank during the disinfection cycle, by detecting water or dialysate in the hose portion (solid line) from valve V6 to air filter AF.

In our design, the housing of the dialysate preparation module 26 includes a floor or base for the entire machine 22, including the other modules 24 and 28. Any fluid such as blood, water or dialysate that leaks from the modules 24, 26 or 28 collects in a catchment basin 284 at the bottom of the entire machine. Leaks will drip on any arbitrary path, shown schematically as broken lines 280 and 282. The floor of the housing for the machine 22 is horioontally non-planar to facilitate the catchment of fluid, in a fashion similar to an oil pan for an engine. The floor of the machine may be bowl shaped or given any other suitable contour to provide a lower catchment basin 284. A fluid sensor 286 is placed in the vicinity of the catchment basin 284 to detect the presence of fluid in the catchment basin 284. If fluid is detected, the user is alerted by an audio or visual indicator, and the machine is checked for leaks.

Referring now to the left-hand side of FIG. 6, a line 283 is provided for conducting water to the chemical application system 260 for rinsing the dialysate chemical bottles 270 after they have been opened, and for disinfection of the bottle's seal. Line 281 is a return line from the chemical application system 260 to valve V13. Line 291 also provides water from three-way valve 287 to a fountain or sprayer 285 in the chemical loading platform 250. Drain lines 236 and 236A provide a pathway for dialysate or disinfection water to exit from the extracorporeal circuit module 28 via the disinfection manifold 494 (see FIG. 36 also) through valve V14, and thermistor 293. Lines 289 and 289A provide a fluid pathway into the extracoporeal circuit module 28 via valve CV11. Line 295 connects the disinfection port 495 of the disinfection manifold 494 (FIG. 36) via line 496. Thermistor 293 monitors the temperature of the fluid returning from the extracorporeal circuit 400 during the hot water disinfection cycle.

A. The Chemical Loading Platform 250

The chemical loading platform 250 of FIG. 6 is illustrated in detail in FIGS. 7A—7F. FIG. 7A is a perspective view of the platform 250 shown positioned against the side of the tank 202. FIG. 7B is a top plan view of the platform 250. FIG. 7C is a sectional view of the platform 250 along the lines 7C of FIG. 7B. FIG. 7D is a sectional view of the platform 250 along lines 7D of FIG. 7B. FIG. 7E is an elevational view of the platform 250. FIG. 7F is a sectional view of the platform 250 along the line 7F of FIG. 7E. In the figures, the platform 250 is an integrally molded housing mounted to the side of the tank 202 and having a top 304 with four apes. Apes 306, 308 and 310 provide passageways for chemicals from the chemical application assemblies 260 which are installed above the top 304 of the platform 350. Aperture 312 is for a line 291 (FIG. 6) to provide water to a sprayer 285 suspended within the platform 250 for rinsing chemicals from the shelf 320 into the tank 202. (See FIG. 6). Shelf 320 is inclined at an angle of between 10 and 30 degrees (preferably 17 degrees) relative to the horizontal to promote dispersion of chemicals delivered onto shelf 320 into the tank 202. Note that the tank 202 has fiberglass windings 314 wrapped around a polypropylene shell 316.

The platform further has a rim 302, 326 and sidewalls 318 and 319. The chemicals are placed in fluid communication with the interior of the tank by virtue of the open side 324 of the platform 250, which is aligned with an opening (not shown) in the tank 202.

Referring to FIG. 6. and 7D, the sprayer 285 sprays fluid (e.g. dialysate or purified water) in the direction of the lower shelf 320 to assist in washing dialysate chemicals off the shelf 320 and into the tank 202, thereby promoting effective dissolution of the chemicals within the tank 202 and the avoidance of buildup of chemicals on the shelf 320.

Referring in particular to FIGS. 7C and 7D, an aluminum plate 322 is mounted to the top of the platform 250 to provide a mounting base for the chemical application assemblies 260 (FIGS. 6, 8A–8C).

B. The Chemical Applicator 260

Figure 8A:
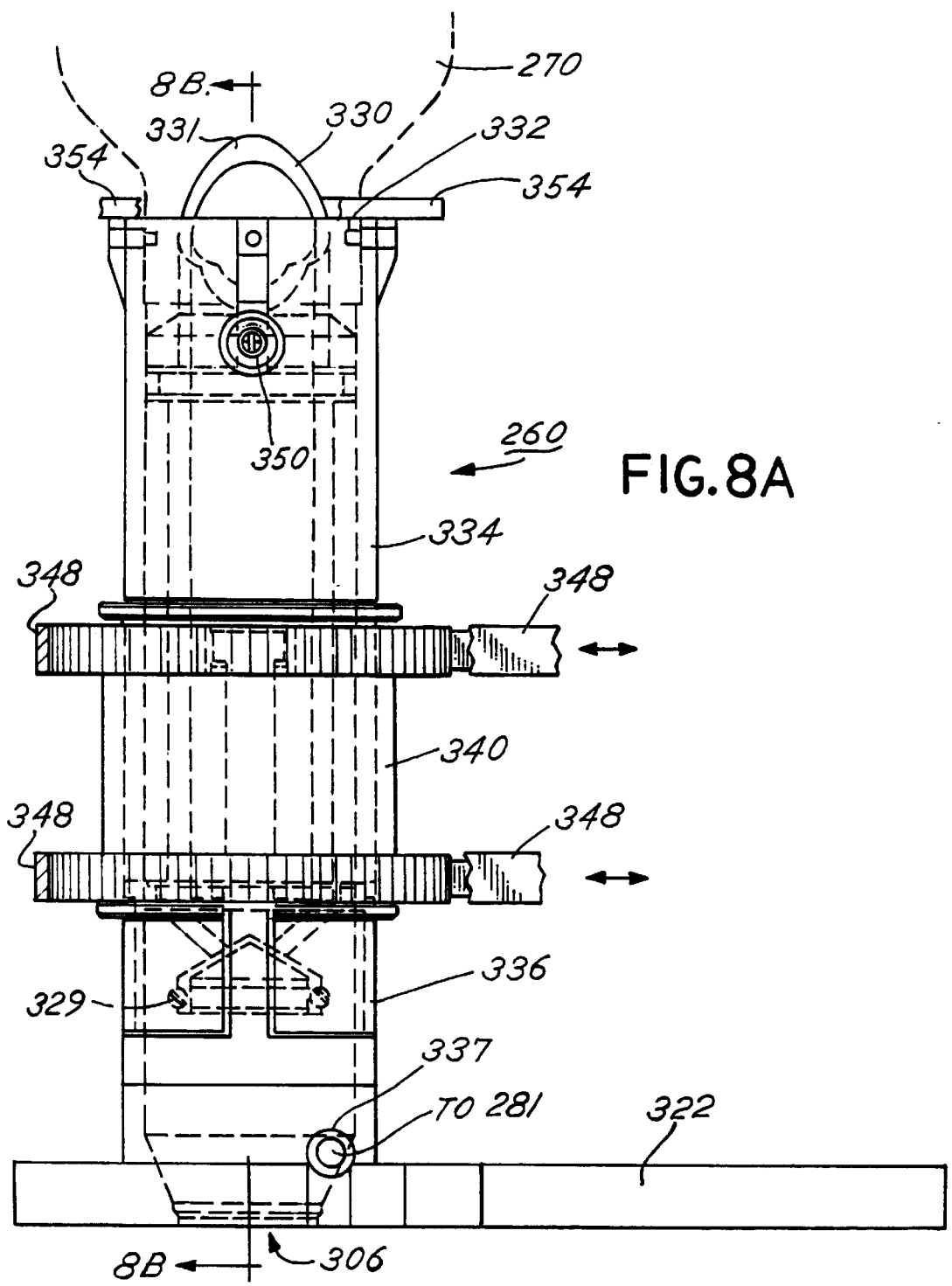

Referring now to FIGS. 8A–8C, the chemical applicator 260 will be explained in detail. The chemical applicators 260 (three in all in the preferred embodiment) arm installed on the aluminum plate 322 directly above the apertures 306, 308, 310 (FIG. 7A). FIG. 8A is an elevational view of the applicator 260, and FIGS. 8B and 8C are sectional views of the applicator 260 with the spike 330 in upper and lower positions, respectively. When the spike 330 is in the upper position (FIGS. 8A and 8B), the tip 331 of the spike pierces the bottle 270 which is installed in an upside-down orientation in the upper region 332 of the applicator 260, causing the chemicals in the bottle 270 to pour out through the applicator 260 and apertures 306 (or 308 or 310) and onto the shelf 320 of the loading platform 250 (FIG. 7).

The applicator 260 has a cylindrical housing 334 mounted to a base member 336 affixed to the aluminum plate 322. The housing 334 has an open interior region 338. A threaded drive collar 340 is mounted to the housing 334. The spike 330 is reciprocable within the interior region 338 between upper and lower positions. The spike 330 pierce the seal on the bottle 270 or other vessel containing the dialysate chemicals (or other contents of the bottle 260) when the spike 330 is moved to the upper position (FIG. 8B). The spike 330 has an integral cylindrical body 342 concentric with the housing 334 with an open interior for permitting passage of dialysate chemicals therethrough after the spike 330 has pierced the seal of the bottle 270. A pair of thread blocks 344 are mounted to the side walls of the spike 330 which engage the threads 346 on the drive collar 340. A drive belt 348 (one or two) or other suitable means (such as a cog) engages the threaded drive collar 340 (FIG. 8A). As the belt 348 rotates the collar 340, the thread blocks 344 are rotated, causing the spike 330 to move between the upper and lower positions depending on the direction of movement of the drive belt 348.

Figure 12:
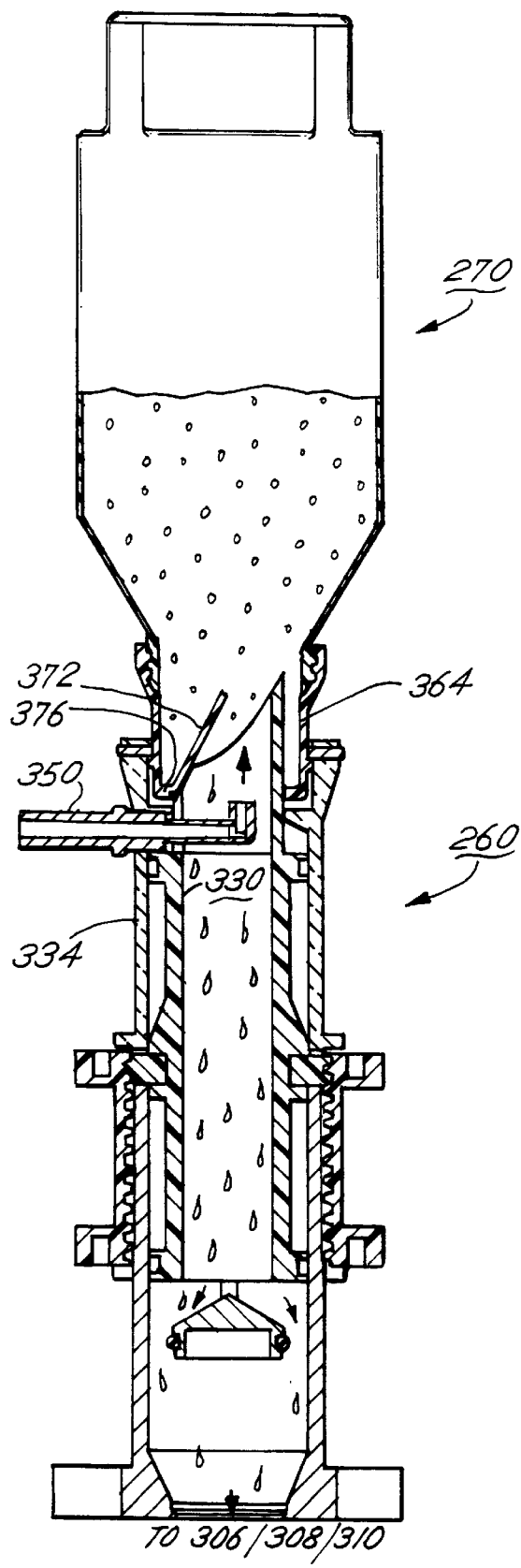
FIG. 12 is a sectional view of the chemical applicator and bottle of FIG. 6 during rinsing of the bottle.

Referring in particular to FIGS. 8B and 8C and FIG. 12, a nozzle 350 is disposed within the cylindrical housing 334 in communication via line 281 with the water inlet line 200. The cylindrical body 342 of the spike has a vertical slit to accommodate the nozzle 350. The tip 352 of the nozzle 350 is oriented upward in the direction of the bottle 270 when the bottle 270 is mounted to the housing 332. The flow of water through the nozzle 250 on demand sects water towards the interior of the bottle 270 after the bottle has been opened by the spike 330, thereby rinsing the interior of the bottle 270 and promoting the release by gravity of the entire contents of bottle 270 through the are 306 (or 308, 310) and into the tank 202. To control the dispensing of dry dialysate chemicals from the bottle, and prevent clogging of chemicals at the base of the bottle, we prefer to pulse water through the nozzle 350 over a period of time. For example, we pulse water through the nozzle for one second (with a pressure greater than 10 psi), then pause briefly while some of the chemicals fall through the interior of the spike 330, then pulse again, pause, and then continue the process until all the chemicals have fallen out of the bottle. This pulsing may occur for perhaps 50 times over a ten minute period. This pulsing action prevents all of the chemicals from being dumped at once onto the shelf of the loading platform. When the bottle is substantially empty, the nozzle rinses out the bottle with a continuous stream of water of 5 to 10 seconds duration.

The nozzle 350 also ejects heated water (or water treated with disinfecting chemicals) onto the outside surface of the seal 372 of the bottle 270 during the disinfection cycle of the machine, thereby disinfecting the interface between the chemicals in the bottle 270 with the dialysate preparation tank 202.

An O-ring 329 is provided around the base 335 of the spike 330. When the spike is in the lower position, outlet tube 337 leading to line 281 (FIG. 6) is open and the tank 202 is closed off through ports 306, 308 and 310.

C. The Chemical Vessel (Bottle) 270 and Automatic Identification System

Referring now in particular to FIGS. 8C and 9A–9C. together with FIG. 10A, a bottle mounting member 354 is placed above the housing 334 of the applicator 260 to insure that the bottle 270 is mounted in alignment with the spike 330 to the applicator 260. The mounting member 354 is shown in a top plan view in FIG. 9A (i.e., as it would be seen when looking down from above in the direction of the top of the spike), in a bottom plan view in FIG. 9B, and in side elevational view in FIG. 9C. The mounting member 354 has a central opening 360 through which the head of the bottle 270 is inserted. A button through hole notch 356 accommodates a touch button 362 (FIG. 10A) containing coded information as to the contents of the bottle 270 that is affixed to the neck of the bottle 270. The touch button 272 is about a half inch in diameter. The member 354 has a pawl 357 (that is retractable by operation of an electric solenoid 358) for automatically removing the touch button 362 when the bottle 270 is removed from the mounting member 354.

During installation of the bottle 270, the head of the bottle 270 (turned "upside down") is placed within the opening 360 and rotated in the direction of the arrow of FIGS. 9A and 9C. The touch button 362 slides past the pawl 357 into contact with a touch button reader. When the bottle 270 is removed from the applicator, the bottle must be rotated in the opposite direction. Pawl 357 is activated by solenoid 358 to an extended position. When the bottle is rotated such that the touch button is rotated past the pawl 357, the pawl 357 pushes the touch button 362 off of the bottle 270, causing the touch button to fall. A suitable catchment structure is provided about the applicators 260 and aluminum shelf 322 (FIG. 8) to catch and collect the fallen touch buttons. The user of the machine 22 collects the buttons and sends them back to a collection center for reprogramming and reuse. Alternatively, the buttons 362 could be collected by a service technician during a service visit.

Figure 10B:
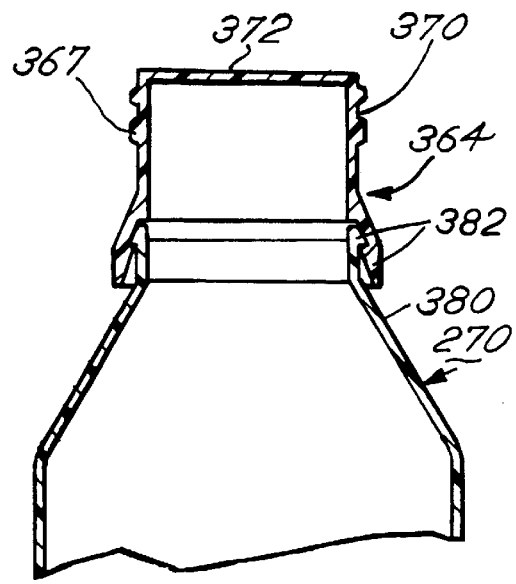

The structure of the bottle 270 is shown in detail in FIGS. 10A–10F. FIG. 10A is an elevational view of the bottle 270 with the touch button 362 removably affixed to the neck region 364 of the bottle 270. FIG. 10B is a sectional view of the neck region 364 of the bottle 270 showing the polyethylene or polypropylene shell 380 and a polypropylene cap 370 snapped onto the shell 380 via circumferential complementary snap elements 382. A polypropylene seal 372 integral with the cap 370 closes off the bottle 270. Polypropylene is chosen for the material for the cap 370 since the cap 370 is subject to hot water disinfection during the disinfection cycle of the machine 22. Specifically, when the bottle 270 is installed within the mounting member 354 above the applicator 260, hot water is applied via nozzle 350 (FIG. 8C) to the exterior surface of the polypropylene seal 372. While polyethylene is a preferred material for the bottle shell 380, it tends to soften when subjected to hot water for an extended period of time.

Figure 10C:
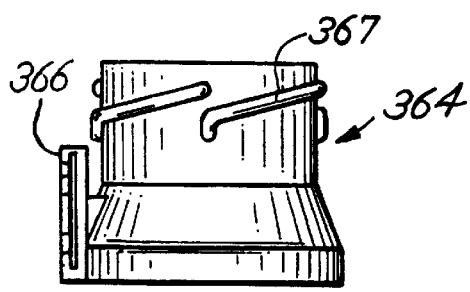
Figure 10D:
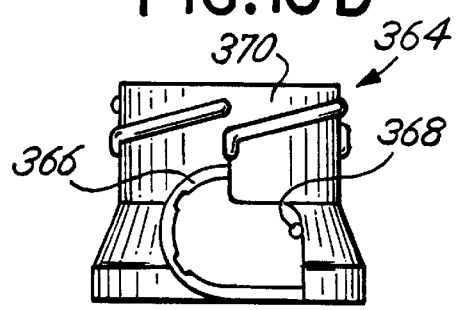
Figure 10E:
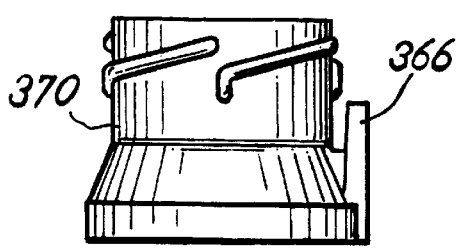

FIG. 10C is a detailed elevational view of the upper portion of the bottle showing the pinch semicircular rim 366 that retains the touch button 362. FIG. 10D is similar to FIG. 10C with the cap 370 rotated 90 degrees. A retaining bead 368 helps keep the touch button 362 in place. FIG. 10E shows the opposite side of the cap 370 from FIG. 10C. The threads 367 engage the upper portion of the housing 334 of the applicator 260 (FIG. 8).

Figure 10F:
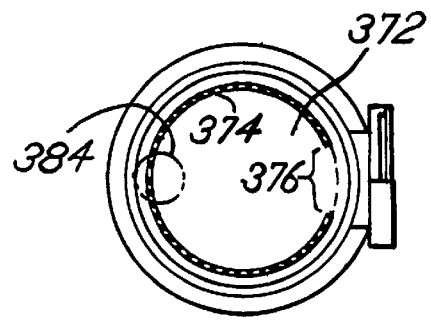

FIG. 10F is a plan view of the seal area 372 of the bottle 270. The seal 372 comprises a frangible section 374 and a hinge section 376. The mounting member 354 (FIG. 9), and in particular the notch 356, acts as a means for insuring that the bottle 270 can be inserted only one way onto the applicator 260 and aligning the upper tip of the spike with the frangible section 374 of the seal opposite the hinge section 376,50 that the tip 331 of the spike 330 (FIG. 8B) contacts the region 384 of the seal 372. The uppermost rim of the spike 330 tears through the frangible section 374, with only the hinge portion 376 uncut, when the spike 330 is moved to its upper position (FIG. 8B). By virtue of the stiff properties of the polypropylene material, and by virtue of the support from the spike 330 from below when the spike 330 is in the upward position, the broken seal 372 maintains an generally upward orientation, allowing the chemicals in the bottle 270 to exit from the bottle 270 and permitting the nozzle 350 to spray into the interior of the bottle 270 to rinse out any remaining chemicals in the bottle 270. The rinsing action of a bottle 270 containing dry dialysate chemicals is shown in FIG. 12.

When the bottle 270 is mounted to the applicator 260, the touch button 362 is placed in touching contact with a touch button reader mounted in any suitable fashion above the applicator 260. The reader retrieves information coded in the button 362 (such as the contents of the bottle, a date code, a lot code, and other information) and passes the information to the central processing unit of the control module 25 (FIG. 1). The control module 25 has a memory storing information such as the correct dialysate chemicals for the patient, the patient's dialysis prescription, and software for processing the information from the touch button. If the bottle is not the proper chemical for the patient, the control module 25 alerts the user, such as by activating a suitable alarm. The user, thus alerted, removes the incorrect bottle 270 prior to commencement of the next dialysis procedure and replaces the bottle 270 with the proper bottle, and the process goes forward. Touch buttons, readers and supporting materials suitable for use with the present invention can be obtained from the Dallas Semiconductor Corp., 4401 S. Beltwood Parkway, Dallas Tex. The above-described identification technique promotes safety and the prevention of unintentional introduction of the wrong dialysate chemicals into the tank.

It will be appreciated that other types of indicators besides touch buttons may be applied to the bottles such that the indicator is read by a machine when the bottle is about to be used. For example, bar codes, two and three dimensional bar or dot matrices, radio frequency transmitters or magnetic strips may be affixed in any suitable fashion to the sides of the bottles and read by the appropriate machine in a well known manner. Ideally, the reading occurs during or immediately after installation of the bottle and prior to the opening of the bottles and introduction of the chemicals to the tank 202, so that in the case that the wrong bottle was installed, the patient is alerted and corrective action can be taken.

D. The Dialysate Circuit 402

The dialysate preparation module 26 her includes a dialysate circuit 402 that circulates dialysate from the tank 202 to the dialyzer 404 and back. The dialyzer 404 (such as the Fresenius F-80 filter) filters blood to remove toxins and excessive water buildup in the patient's blood. The patient's blood is introduced into the machine via the extracorporeal circuit 400 (FIG. 13).

The inlet line 406 carries dialysate solution to a thermistor 408, which monitors the temperature of the fluids in the line 406. A pressure transducer 410 (Microswitch 26PC X-98752PC) monitors the pressure in the line 406. Bypass valve 412, and input and output valves 414 and 416 control the flow of dialysate into and out of the dialyzer 404 via input line 418 and output line 420.

During dialysis, the thermistor 408 data is fed to the safety CPU 616 (FIG. 16) to insure that the temperature of the dialysate is less than a maximum critical temperature, in the present example 39 degrees C. If the temperature is greater than the critical temperature in the safety CPU 616 closes off valves 414 and 416 and opens up bypass valve 412. Conductivity sensor 218 data (FIG. 6) is also fed the safety CPU 616 and if abnormal conductivity readings are sensed, the valves 414 and 416 are closed and bypass valve 412 is opened.

The return flow of old dialysate is via line 422. A noninvasive conductivity monitor 426 (same as item 218, FIG. 11) and a blood leak detector 428 are provided in the line 422. Blood leak detector 428 detects a leakage of blood from the dialyzer 404 into the dialysate. The presence of blood in the line 422 also causes valves 414 and 416 to close and valve 412 to open, to prevent any additional loss of the patient's blood.

E. The Blood Leak Detector 428

Background information on blood leak detectors known in the prior art can be found in U.S. Pat. Nos. 4,925,299; 4,166,961; 4,087,185 and 4,017,190, the contents of which are incorporated by reference herein. Our presently preferred design, based on absorbency of light by the blood, is shown in schematic form in FIG. 25A. A light emitting diode (LED) 530 is pulsed between an OFF condition and an ON condition, during which it emits light at which the absorbency of the light by blood is at a maximum, such as 880 nm. The light from the diode 530 passes through a mirror-coated beam splitter 532. The resulting light of intensity P is split into two portions. One portion is directed toward a reference photodiode 534, and the other portion is directed through a chamber or cuvette 536 containing dialysate solution and onto a second blood detector photodiode 538 identical to the reference photodiode detector 534. The reference photodiode 534 also receives light from external interfering light sources $P_{EXT2}$ directed onto the diode 534. The reference diode 534 is used for generating a light intensity correction factor, as discussed below. Photodiode 534 is connected to an operational amplifier 540 having a resistor 542. The output voltage of the op. amp. 540 is represented by $V_{PD2}$.

External interfering light sources $P_{EXT1}$ also impinge on the photodiode detector 538. The photodiode detector 538 is connected to operational amplifier 546 having resistor 533 connected across the output and negative terminals as shown. The resulting output voltage signal is represented by $V_{PD1}$. Suitable beam splitter and optical diffusing glass components for the detector of FIG. 25A can be obtained from Edmund Scientific Co., of Barrington, N.J.

The housing for the blood leak detector (not shown) is con so as to deflect any air within the cuvette 536 away from the light path 535. Curved entry paths or baffle plates may be used for this purpose. The goal is to prevent air bubbles for adhering to the transmitting and receiving windows 537 and 529, respectively on the sides of the cuvette 536. Maintenance of turbulence of the fluid within the cuvette 536 should accomplish this, but the above-cited blood leak detector patents disclose additional techniques for the avoidance of air-bubbles along the light path of a sensor.

Figure 25A:
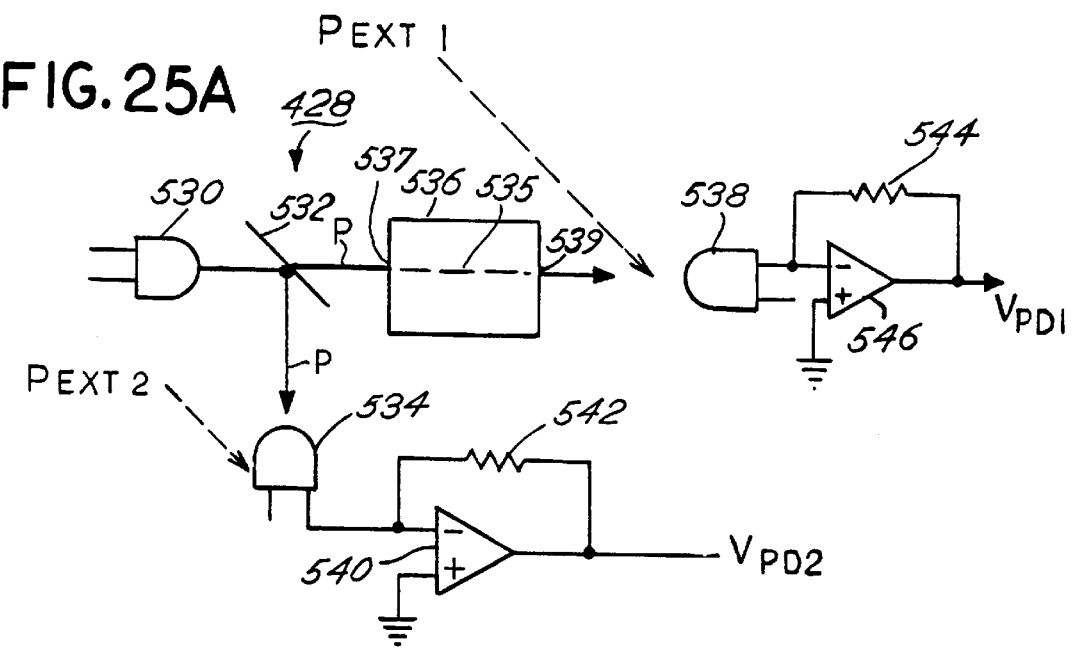
FIG. 25A is a schematic diagram of the blood leak detector 428 of FIG. 13.
Figure 25B:
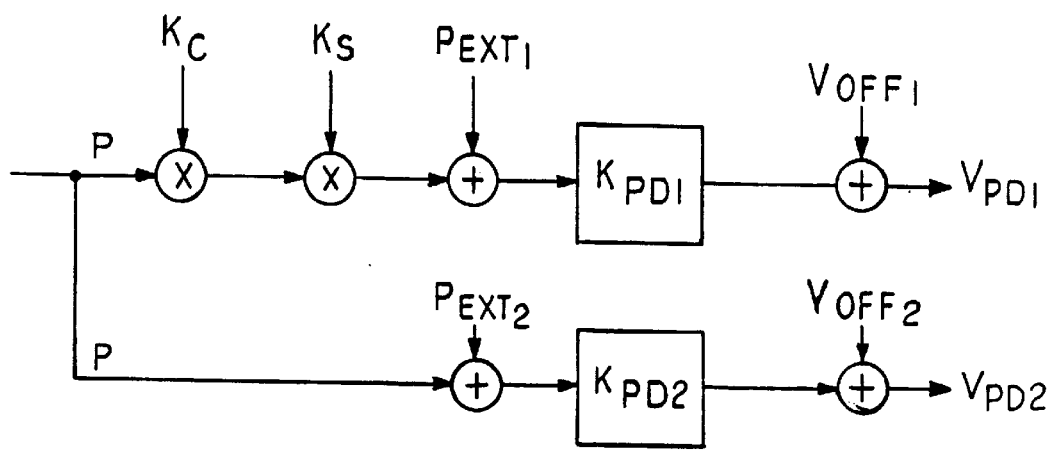
FIG. 25B is a diagram of the flow of signals in the blood leak detector of FIG. 25A.

The signal flow of the blood leak detector 428 of FIG. 25A is shown in FIG. 25B. The following is a table of the legends used in FIG. 25B.

P=LED 530 Light Intensity $K_C$=Light Attenuation of Cuvette 536 and Dialysate $K_S$=Attenuation Coefficient Due to Blood in Dialysate $P_{EXT1}$, $P_{EXT2}$=External Interfering Light Sources $K_{PD1}$, $K_{PD2}$=Photodiode 538, 534 Sensitivity Coefficients, respectively $V_{OFF1}$, $V_{OFF2}$=Electronics Offset Coefficients for 546, 540, respectively $$V_{PD1}=(P \cdot K_C \cdot K_S+P_{EXT1})K_{KD1}+V_{OFF1}$$

Prior to dialysis, a control solution consisting of dialysate solution free from blood is introduced into the cuvette 536, the light source 530 is pulsed on and off and measurements of the light intensity in the reference and blood leakage photodetectors 534, 538 respectively are made. The measurements during the light off condition are stored and subtracted from the next light-on measurement. The process is repeated during the conduction of dialysate solution from the dialyzer 404 during dialysis. A calculation of an attenuation coefficient indicative of the presence of blood in the dialysate is made repeatedly during dialysis, and an alarm is sounded if blood is detected. The provision of the reference detector 534 permits the removal of any offset or drift conditions in the electronics or variation in the light intensity from the light source 530.

The photodiodes 534, 538 must be shielded from extraneous light sources. such as incandescent bulbs or fluorescent lights. Any residual light appearing on the detectors $P_{EXT1}$ and $P_{EXT2}$ is low-pass filtered. The filtering passes only the DC component of the extraneous signal. The DC component of the extraneous signal is removed in the on-off pulsing that removes electronic offset and drift.

Any additional light paths from source to detector must also be minimized. Light paths other than that through the dialysate will cause the measurements to deviate from the expected levels for a given concentration. This cannot be corrected since the offset measurement is taken with the light source off. The extraneous light path can be measured by a given cuvette by replacing the dialysate with a fluid of virtually no light transmittance. Then the light source is varied from 0 to maximum output and the detector output monitored.

The blood concentration measurement is as follows. Prior to treatment, the light intensity at the photodiode detectors 538 and 534 is measured before the dialysis treatment.

No Blood $K_S$=1.0, Light Off $P=O$ $V_{PD1_{OFF}}'=P_{EXT1}K_{PD1}+V_{OFF1}$ (1)

No Blood $K_S$=1.0, Light on P $V_{PD1_{ON}}'=(PK_C+P_{EXT1}) K_{PD1}+V_{OFF1}$

If $P_{EXT1}, K_{PD1}, V_{off1}$ Constant Between 1+2 $V_{PD1_{ON}}'-V_{PD1_{OFF}}'=PK_CK_{PD1}$ (2)

During treatment, the light intensity at the detector 538 is measured. The ratio of the intensity before treatment over the intensity during treatment is computed. In addition, the reference photodiode detector 534 is measured to correct the intensity readings during treatment from offset, drift, and extraneous light sources. Measurements and calculations are as follows:

Blood $K_S$, Light Off $P=0$ $V_{PD1_{OFF}}=P_{EXT}K_{PD1}+V_{OFF1}$ (3)

Blood $K_S$, Light On P $V_{PD1ON}=(PK_CK_S+P_{EXT1})K_{PD1}+V_{OFF1}$

If $P_{EXT1}, K_{PD1}, V_{OFF1}$ Constant Between 3+4 $V_{PD1ON}-V_{PD1OFF}=PK_CK_SK_{PD1}$ (4)

The attenuation coefficient due to the presence of blood in the dialysate, $K_S$, is as follows (assuming $K_C$, $K_{PD1}$ are constant during the treatment):

$$\frac{V_{PD1_{ON}} - V_{PD1_{OFF}}}{V_{PD1_{ON}}' - V_{PD1_{OFF}}'} = \frac{PK_CK_SK_{PD1}}{PK_CK_{PD1}} = K_S$$

Suppose that the light intensity from the LED 530 increased 50% after the initial measurements prior to dialysis were made, for whatever reason. The attenuation coefficient $K_S$ is the same. The manufactures' variations for light intensity P, photodiode sensitivity $K_{PD1}$ and $K_{PD2}$ will not effect the calculation of the attenuation coefficient, since they cancel out. Thus:

No Blood, Before Treatment $$V_{PD1_{ON}}' = V_{PD1_{OFF}}' = PK_C K_{PD1}$$

Blood, During Treatment $$V_{PD1_{ON}} - V_{PD1_{OFF}} = P(1.5) K_C K_S K_{PD1}$$

The reference detector 534 is used for correction:

No Blood, Before Treatment $$V_{PD2_{ON}}' - V_{PD2_{OFF}}' = P K_{PD2}$$

Blood, During Treatment $$V_{PD2_{ON}} - V_{PD2_{OFF}} = P(1.5) K_{PD2}$$

Attenuation Calculation (If $K_C$, $K_{PD1}$, $K_{PD2}$, Constant During Treatment)

$$\frac{V_{PD1_{ON}} - V_{PD1_{OFF}}}{V_{PD1_{ON}}' - V_{PD1_{OFF}}'} \times \frac{V_{PD2_{ON}}' - V_{PD2_{OFF}}'}{V_{PD2_{ON}} - V_{PD2_{OFF}}} =$$

$$\frac{P(1.5)K_C K_S K_{PD1}}{PK_C K_{PD1}} \times \frac{PK_{PD2}}{P(1.5)K_{PD2}} = K_S$$

It will additionally be noted that the above calculations of $K_S$ assume the beam splitter 532 is a 50% splitter directing light in two paths of equal intensity P. A different ratio of the light intensity could be used with a conversion factor used in the $K_S$ calculation.

If the sensitivity of the diodes 534 and 538 varies differently from each other during the treatment, then the attenuation coefficient $K_S$ will vary. This situation will be avoided by choosing the same type of photodiode detectors 534, 538. Additionally, the photodiode sensitivity coefficient variance is typically small.

The blood leakage detector can be tested by varying the intensity of the light source 530 and making sure that the reference and blood sensor photodiode detectors, 534 and 538, respectively, track within limits. The supporting electronics for the blood leakage detector 428 should be low-noise with high stability. Calibration tests must be performed to determine the expected light levels detected for various dialysate flow rates and blood concentrations. The path length of the light within the cuvette determines the sensitivity of the optical density measurements.

As an alternative approach, instead of pulsing the light from LED 530 on and off, the light intensity can be sequenced OFF, LOW and HIGH. If a blood concentration in the cuvette 536 causes a low reading near the noise floor of the electronics, the next higher detector reading corresponding to the high light source intensity can be used.

IV. The Extracorporeal Circuit Module 28

Figure 27:
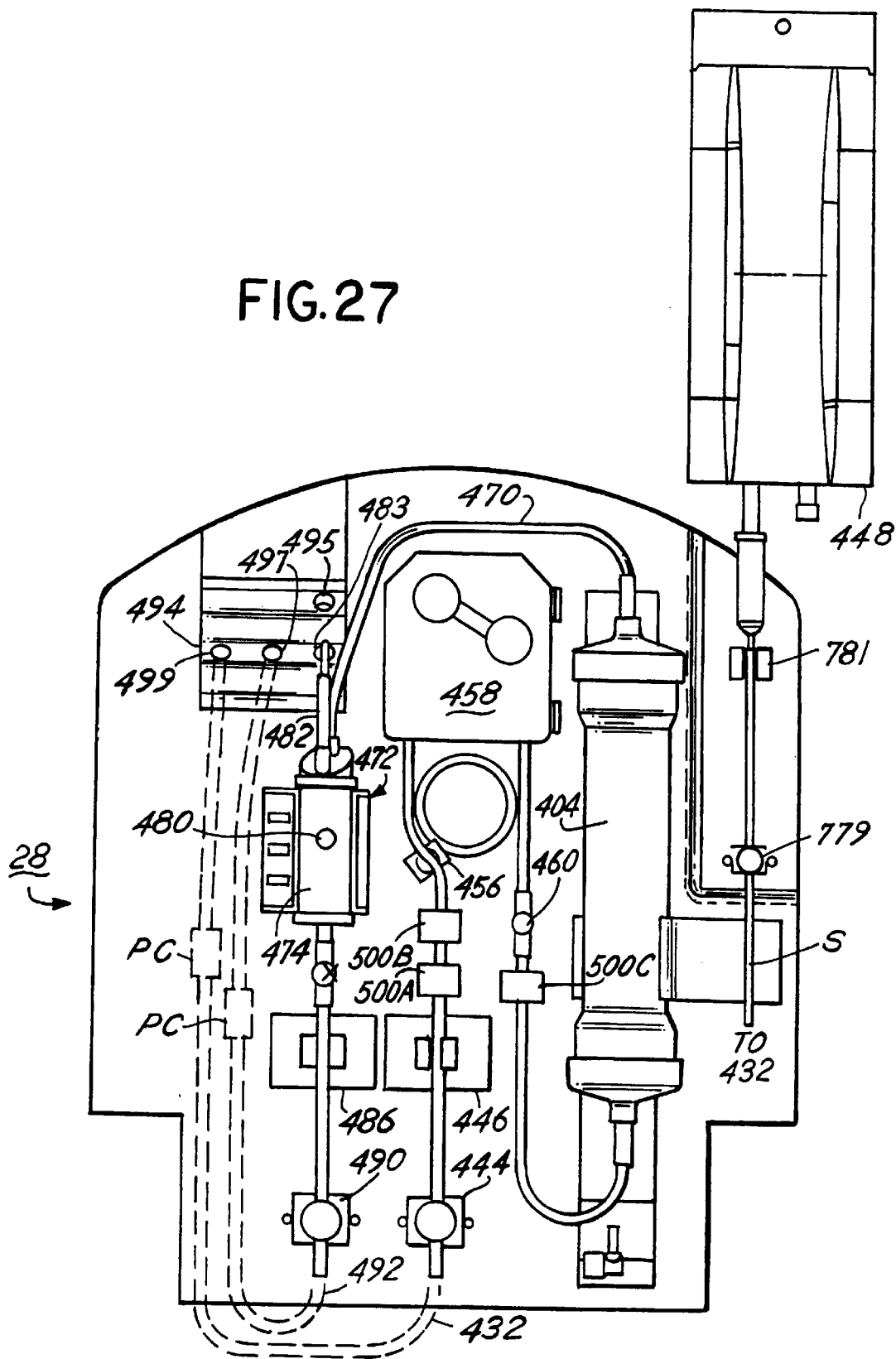
FIG. 27 is an elevational view of the extracorporeal circuit module 28 of FIG. 13; with the arterial 432 and venous 492 blood tubes shown in dashed lines connected to the disinfection manifold 494, as they would be when the dialysis session has been completed.
Figure 32:
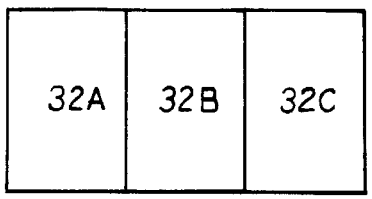

Referring now to FIGS. 13 and 27, the extracorporeal circuit module 28 will be described in detail. The patient's blood is introduced into the extracorporeal blood circuit 400 in arterial line 432. If a saline bag 448 is used as discussed below, the saline is introduced into the arterial line 432 at three-way connector TC with rotating male luer lock and two female luer lock such as Haemotronics Part No. B-82 or, alternatively, a four-way injection site with rotating male luer lock/double female luer lock, such as Haemotronics Part No. CR-47. The saline bag 448 is optionally provided, and is connected to the arterial line 432 by a saline infusion line S having an optical fluid sensor 781 and a clamp 779. The saline bag 448 has several potential uses: for priming air out of the extracoporeal circuit 400, for replacing lost fluid during therapy and rehydrating the patient, and for rinsing back blood to the patient. Our reverse osmosis water and ultrapure dialysate, introduced to the extracorporeal circuit 400 by causing a pressure differential to exist at the membrane of the dialyzer, serves these functions, thus the saline bag 448 is for an alternate method of priming and rinseback. The optical fluid sensor 781 detects when the saline bag is empty, and permits automatic identification of the condition to the patient, obviating the need for periodic checks of the saline bag 448. When air is sensed by the sensor 781, the clamp 779 is closed. An alternative to the use of a fluid sensor 781 is an in-line infusion filter in the infusion set which obviates the need of a fluid sensor.

A clamp 444, an ultrasonic air bubble detector 446, a redundant pressure monitor 500A, a pressure monitor 500B and an optional injection site (needle or needleless type) 456 are placed in the line 432. Blood pump 458 pumps blood into line 462, via special pump section tubing (from Pharmed™ material or silicone) past injection site 460 and pressure monitor 500C and (optional) expansion chamber 466 to the dialyzer 404. The blood is returned to the patient via line 470 to an air-separating and pressure monitoring chamber 472 having an inlet tube 471 at the top or bottom, with the top preferred.

Referring in particular to FIGS. 13 and 27, the air-separating and pressure monitoring chamber 472 has a chamber 474, an upper and a lower blood level sensors 476 and 478 respectively, and an optional injection site 480 (one or more). A third blood level sensor could be provided with the chamber 472 for monitoring or controlling the blood level. The chamber 474 is in air communication via line 482 to a connection port 483 in a disinfection manifold unit 494, which is further connected to a line 491 having a pressure sensor 775, valve 777 and then open to atmosphere. A restrictor may be needed in the line 491 to control the rate of air flow in and out of the line 491. Because the fluid in the chamber 474 is normally under positive pressure during dialysis, the level may be raised (when identified as being too low by the level sensor 478) by opening valve 777 until the level is raised to the level of sensor 476. The level may be lowered by stopping the occlusive blood pump 458, opening valve 777, and operating UF pump 242 (FIG. 6) until the level is lowered and sensed by sensor 478. An alternative method would be to close venous clamp 490, open valve 777, and operate the blood pump 458 in reverse until air is sensed by sensor 476. The bottom of the chamber 474 is connected to a line 484 having an ultrasonic air bubble detector 486, a blood sensor 488 and a clamp 490 and is connected to the venous line 492 which leads to the patient.

A pressure transducer isolator (a disc shaped unit) 493 (FIG. 36) is installed at the interface between the line 482 and the port 483. The isolator 493 has a microporous membrane which allows no fluid to escape out of the line 482 but which allows air to escape and enter the line 491.

It is common in extracorporeal blood circuits to have a blood filter which filters the blood as well as eliminates air or gas bubbles. The typical application for these filters is in major surgical procedures. The blood flow rates for these surgical procedures range from 3 to 6 liters per minute. The typical blood flow rate for hemodialysis is only 200 to 600 milliliters per minute.

Figure 15A:
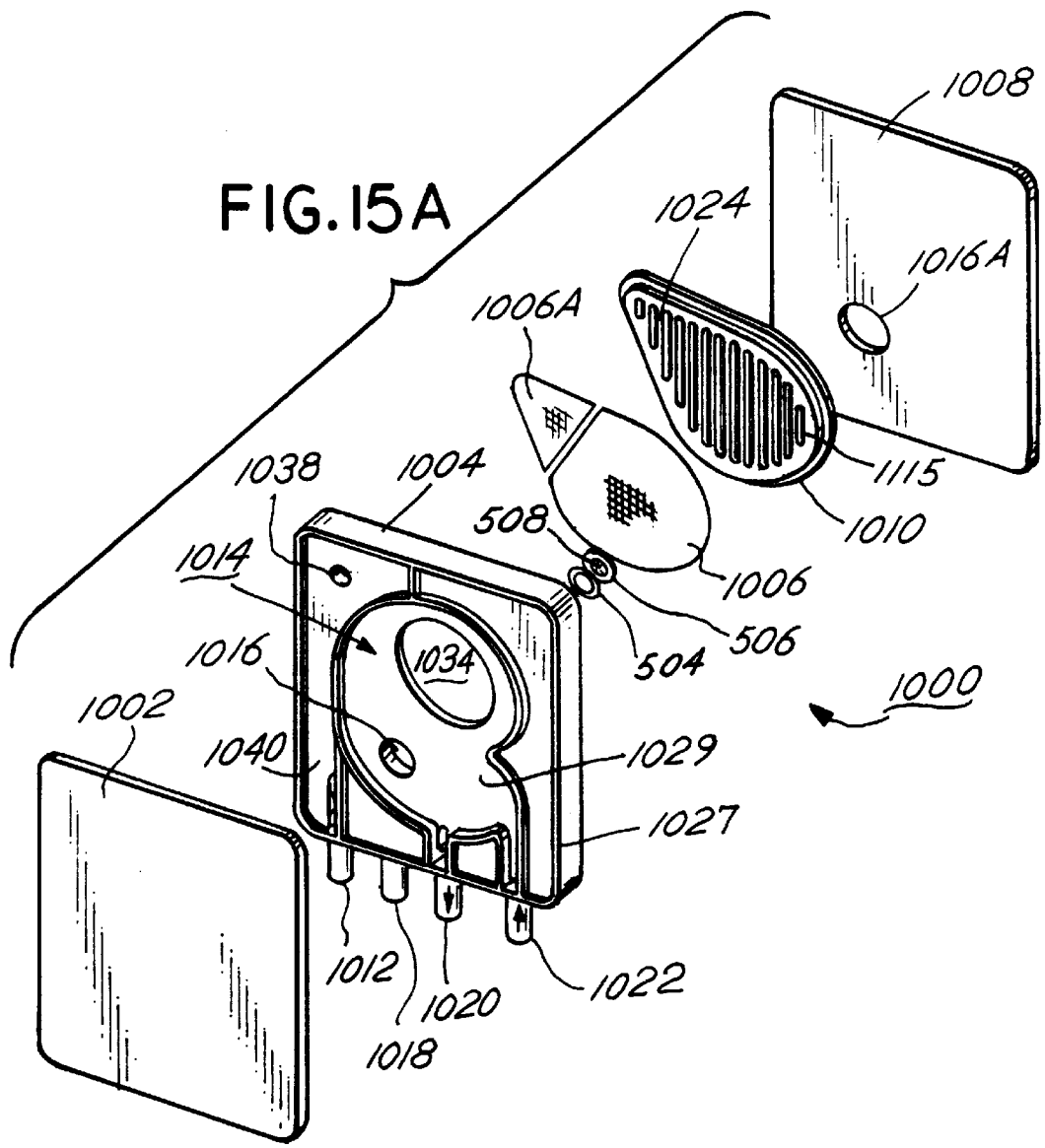

It is well known that air contact with blood often causes clotting. This is one of the draw backs of traditional bubble traps. Bubble traps also require level sensors and a valving scheme and control system to allow the collected air escape. By using a hydrophobic microporous membrane to allow the air to escape passively, less clotting occurs, less sensing and valving hardware is needed, and fewer set manipulations by the patent or machine operator are needed. In addition, the unit is simpler to clean and sanitize. Thus, an alternative to the air separating and pressure monitoring chamber 472 is a cassette type debubbler 1000, shown in FIGS. 15A–15D. FIG. 15A is an exploded view showing the front or blood side of the debubbler 1000. FIG. 15B is an exploded view showing the rear or air side of the debubbler 1000. FIG. 15C is a cross-sectional view of the debubbler 1000 through the blood outlet 1020 in an assembled condition, with the unit in a vertical orientation as it would preferably be installed in the extracorporeal circuit 400 (FIG. 13). FIG. 15D is a perspective view of the debubbler 1000 partially broken away in section in the same plane as FIG. 15C. Also for this application the debubbler 1000 is designed to be cleanable, sanitizable and reusable.

Referring to FIG. 15A, the debubbler 1000 has a front cover 1002, a fluid circuit board 1004, two microporous membranes having a blood contact portion 1006 and a secondary air vent 1006A, a back cover 1008 with pressure transducer opening 1016A and an over molded support portion 1010 having a series of parallel support ridges 1024 separated by adjacent parallel apertures 1115. The fluid circuit board 1004 has a blood chamber 1014 and an optional pressure transducer opening 1016 disposed therein. A retaining ring 504 and pressure transducer comprising diaphragm 506 with metal disk 508 are mounted within the opening 1016 for measuring the blood pressure in the blood chamber 1014. The magnet, rod and strain guage elements of the pressure transducer are described in construction with FIG. 14A–C below.

A condensate outlet 1018, a blood inlet 1022 and a blood outlet 1020 are provided at the bottom of the fluid circuit board 1004. An air port 1012 is also provided at the bottom for conducting air passed through the filter 1006A and 1006 out of circuit board 1004. Referring to FIG. 15B, which is a exploded view of the debubbler 1000 seen from the rear or air side, the fluid circuit board 1004 also has a condensate chamber 1032 and hole 1038 covered by membrane 1006A, a membrane peripheral seal area 1028 where the microporous membrane 1006 is sealed to the fluid circuit board 1004, a raised rib 1026 and a channel 1030 for collecting condensate. Condensate is passed out of the unit 1000 from condensate outlet 1018.

It is well known that hydrophobic microporous membrane filters will allow air to escape a chamber while preventing aqueous liquids to escape through the membrane. This also works with blood. PTFE, also known as TEFLON™, microporous membrane filters have been used successfully for many years. However, if blood flow is deadheaded against a rare microporous membrane filter, in a short period of time the membrane will become coated with a biofilm that impedes air escapement. It is well known that PTFE attracts lipids and proteins. It is also well known that if the blood flow is allowed to flow past the microporous membrane in a tangential manner, the flow minimizes the build up of a biofilm and better maintaining air escape efficiency.

Prior art air venting blood filters for surgical use typically employ an essentially horizontal inlet port that passes blood tangentially across a horizontal hydrophobic membrane. The blood flow across and around and then down through a blood clot filter and out. There are several variations to this theme. There are reports that claim the clot filters cause more clots than they eliminate from the flow stream. All these surgical units are designed for single use and are relatively expensive. For our hemodialysis application, no clot filters will be used.

Recently, two microporous membrane manufacturers, Pall and Millipore, have introduced PVDF (polyvinylidene fluoride) also known as KYNAR™ membranes that have superior hydrophobic properties over PTFE and which reportedly do not have the protein and lipid attraction that PTFE has. PVDF is the preferred material for the membranes 1006, 1006A of the cassette-debubbler 1000 of FIG. 15. PVDF has the following properties: sealability to the PVDF microporous membrane, blood compatibility, natural hydrophobia, moldability, heat sealability, translucency and can be compliant under pressure. Polysulfone could also be used as an alternate material with difficulty and with a trade off in properties.

To achieve tangential flow, our microporous membrane filter 1006 is installed in an essentially vertical orientation. The blood inlet port 1022 is also vertical, as is the outlet 1020. The inlet port 1022 can be from either the top, bottom or side. Our preferred embodiment is having the inlet 1022 enter from the bottom.

The covers 1002, 1008 are heat sealed to the ribs 1027, 1026 using a heat seal process. The fluid circuit board 1004 is fabricated preferably by injection molding with ribs 1027, 1026 forming channels on both sides of a central plane 1029 of material. Three holes are provided in the fluid circuit board. The hole 1016 is for the silicone diaphragm pressure transducer. The silicone diaphragm or membrane 506 is to be captured and secured by welding a retaining ring 504 over the edge of the silicone to a mounting structure 1036 on the fluid circuit board 1004.

The hole 1034 is covered with the microporous membrane 1006 and sealed around the edges to the fluid circuit board 1004. This can be accomplished several ways. The membrane 1006 can be placed in the part and heat sealed in place at membrane peripheral seal area 1028 or held mechanically in place. The preferred embodiment insert molds the membrane in place. To insure even better seal integrity, the insert molded membrane 1006 can be over molded with support member 1010. Coincident with the over molding would be the addition of suitable support ribbing 1024.

The membrane 1006 is placed over the hole 1034 from the back side of the fluid circuit board 1004 (FIG. 15B), the back side being the non-blood contact side. Placing the membrane 1006 from the back is necessary because the objective is to be able to eliminate all the air from the chamber 1014 on the blood side (FIG. 15A). If the periphery seal was accomplished from the blood side, then the seal area at the top of the chamber would be higher than the active membrane area, making total air elimination impossible. Total air removal is important for sanitization purposes.

Usually, insert molded filters are designed such that the direction of flow applies force perpendicular to the peripheral seal area and against the seal area. Because of the total air removal issue, the fluid flow in this instance applies a peel force to the peripheral seal when the membrane is placed from the back. Integrity of the filter membrane 1006 and seal is dependent on the membrane strength and the peel seal strength. A second insert molding of an overseal around the periphery of the membrane 1006 is used to better secure the membrane 1006 and eliminate the possibility of the pressure exceeding the peel force strength. The membrane 1006 ends up sandwiched between two layers of plastic. With the over molding 1010 of the seal, support members 1024 are also added to further support the membrane 1006 against the flow pressure preventing distortion and possible rupture of the membrane 1006. Alternately, this can also be accomplished mechanically. The membrane filter 1006 material may or may not have a polymer screen mesh incorporated into its structure to improve membrane strength.

Blood enters the blood side of the chamber 1014 through the inlet port 1022. The flow is directed to the center of the chamber 1014 to gently disrupt the flow pattern and allow the previously entrained bubbles to contact the microporous membrane 1006 and escape. To enhance contact time with the microporous membrane 1006, the distance-between the front cover 1002 of the chamber 1014 and the microporous membrane 1006 is preferrably ⅛ inch or less. For typical bubble traps the volume and geometry of the chamber required is considerably larger. This is necessary in order to slow the blood flow down and give the entrained bubbles time to escape the viscous blood.

The back side of the fluid circuit board 1004 (FIG. 15B) manages the air that passes through the microporous membrane 1006 and condensate formed during sanitation. Air and condensate is allowed to flow into condensate region 1030 and down and out the exit port 1018 to drain via silicone tubing, a connector, a pinch valve and suitable internal machine plumbing (not shown).

Air is let in or out through the air port 1012 at the bottom of the cassette via silicone tubing, a connector, a pinch valve and suitable internal machine plumbing. Some condensate is also allowed to exit the cassette through port 1012. In the preferred embodiment of the cassette, the air will be directed through the hole 1038 back to the front of the fluid circuit board, down a channel 1040 (FIG. 15A) and out the bottom of the cassette at air port 1012. The hole 1038 is covered by a microporous membrane 1006A. This membrane could be an extension to the original membrane or a separate piece as shown. The second membrane 1006A serves as a safety mechanism. Should the primary membrane 1006 fail, the patient could suffer a potentially catastrophic loss of blood. With the secondary membrane 1006A, if the primary membrane 1006 ruptured, the blood would be stopped by the second membrane. A blood detection sensor (not shown) is provided to sense the presence of blood on the back side of the cassette and the activate an alarm and stop the machine. The blood detection sensor is similar to the blood leak detector 428 described above. Because the volume of space between the two membranes is sterile (ETO or radiation sterilization post assembly), the patient will not be at risk of infection should the primary membrane rupture.

During sanitation, if condensate occurs on the air side of the membranes 1006, it can be removed by allowing the condensate and air to exit the cassette from the bottom via port 1018 utilizing gravity. If condensate occurs on the down stream side of filter 1006A it can be removed by allowing the condensate and air to exit via port 1012. Otherwise a condensate build-up could act as a shutoff valve and block all air passage in or out.

Figure 36:
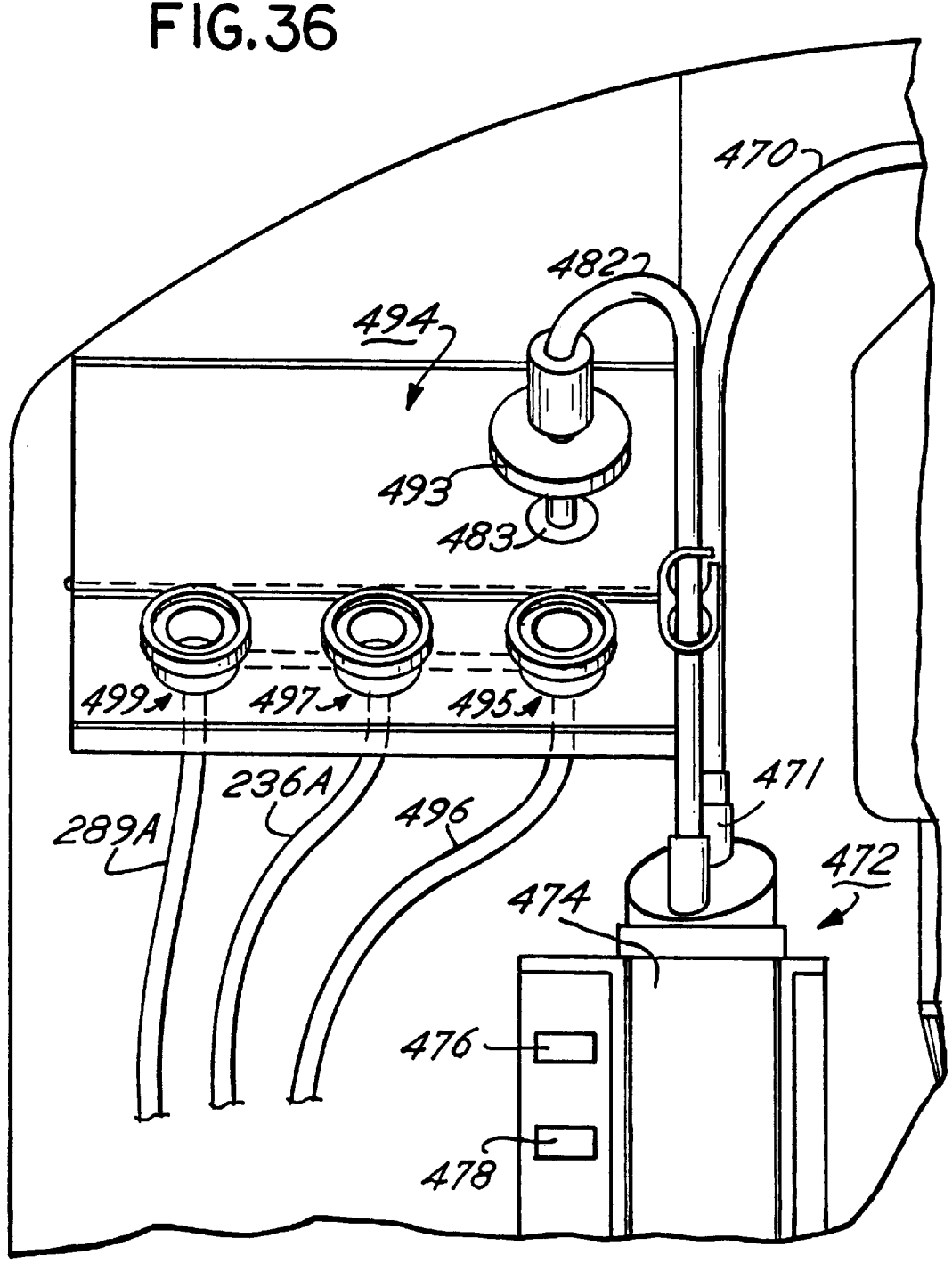
FIG. 36 is a detailed perspective view of the disinfection manifold 494 of FIG. 13.

Referring to FIG. 13 and FIG. 36, the disinfection manifold 494 includes disinfection ports 495, 497 and 499. Port 495 is connected at the back side of the manifold 494 to disinfection line 496, which carries disinfection fluids (e.g., hot water) to the extracoporeal circuit 400. Ports 497 and 499 receive the connectors at the end of the venous and arterial lines 432 and 492, respectively after the dialysis session is completed. Ports 497 and 499 are connected to each other via valve V20 (FIG. 6). Port 497 and port 495 are connected via a T fitting on the back side of the disinfection manifold 494. These connections provide a path for the flow of disinfection fluid (i.e., hot water or water treated with disinfection chemicals) through the entire extra corporeal circuit 400, including the blood side of the membrane in the dialyzer 404. The port 483 is not in fluid communication with the other ports 495, 497, 499. When the dialysis session is completed, the patient reconnects the bubble trap line 482 from the port 483 to the disinfection port 495. While the disinfection manifold 494 could be formed as a unitary housing, it may also simply be composed as an array of connectors having the fluid communication pathways described herein (or equivalents). Referring now also to FIG. 6 and 36, it will be seen that lines 289A and 236A connect at the back side of the disinfection manifold 494 to ports 499, 497.

The back side of the disinfection manifold 494 is connected via return lines 236A and 289A to valves V14, V20, check valve CV 11 and thermistor 293 (FIG. 6). Lines 236A and 289A connect through the disinfection manifold to the arterial 432 and venous 492 lines, respectively, of the extracorporeal circuit, when the lines 432 and 492 are connected to the ports 499, 497 of the disinfection manifold 494, as shown in FIG. 27.

The preferred design of the connection terminals for the lines 432 and 492 is shown in FIG. 37A–C and 38A–D. A preferred design of the ports of the disinfection manifold 494 are shown in FIG. 39A–C. Referring to FIG. 37A–C, an integral inner piece or male luer with luer lock 550 is shown in an end view in FIG. 37A, a cross-sectional view in FIG. 37B, and in a elevational view with a tube 552 in phantom in FIG. 37C. The male luer 550 receives the end of a silicone tube 552 by insertion of the tube over the cylindrical tubing port 554. A secondary silicone oversleeve could also be placed over the tube 552. The male luer 550 has a locking hub 556 with threads 560 disposed on its inner surface. The connector further includes a second elongate spout or tube portion 558 integral with the wall 562 and tubing port 554. A pair of apertures 551 are provided in the side walls of the locking hub 556 to allow air to vent out of the interior of the locking hub 556. At least one aperture is needed on connectors with integral nonrotating locking hubs. The aperture can be anywhere on the locking hub shoulder.

Figure 37D:
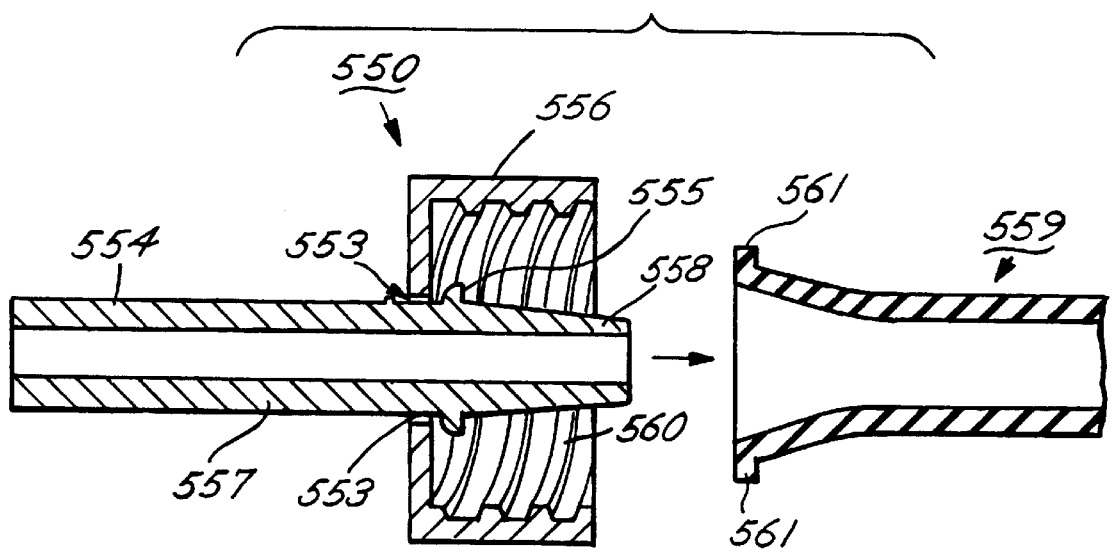
FIG. 37D is an illustration of the connection of an alternative construction of a male luer from the embodiment of FIG. 37A onto a female luer.

Referring to FIG. 37D, in operation, male luer 550 locks onto female luer 559 by virtue of threaded engagement of flange 561 of female luer 559 with threads 560 of male luer 550 and rotational movement of locking hub 556 relative to female luer 559. In FIG. 37D, an alternative construction is shown in which the locking hub 556 is a separate spinning hub piece that snaps over a circumferential ridge 555. Air vents out of the hub 556 by virtue of the clearance 553 between the locking hub and the integral tube 557.

Figure 38D:
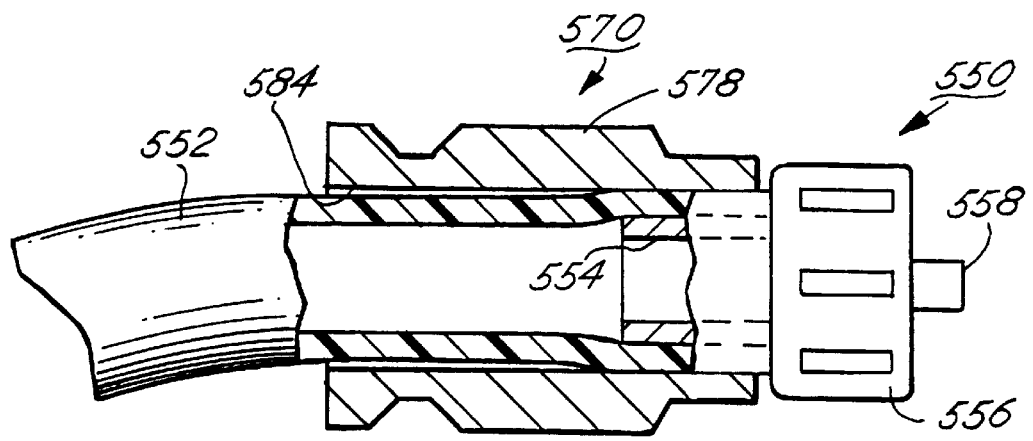
FIG. 38D is an elevational view and partially broken away of the tubing connector of FIG. 38A in an assembled contion.

The connection terminal further includes a separate outer piece 570, shown in FIGS. 38A–D. FIG. 38A is a perspective view of the outer piece 570 prior to pushing the outer piece over the male luer 550 to secure the two pieces together. FIG. 38B is an end view of the outer piece 570. FIG. 38C is a sectional view of the outer piece. The generally elongate cylindrical outer piece 570 has a housing 572 with a recessed notch portion 574 on its outer surface, a series of axially disposed raised ridges 576 circumferentially disposed on the housing, with or without spaces 577 between the ridges 576. A slanted shoulder region 578 is disposed adjacent to the end region 579 of the piece 570. The interior region of the piece 570 is dimensioned to provide compression on the tube 552 preferrably 360 degrees around the tube and male luer 550 when the outer piece 570 is pressed in a friction fit over the tube and luer 550. The recesses 577 can be omitted with housing 572 smooth at the thickness of ridges 576.

Figure 38E:
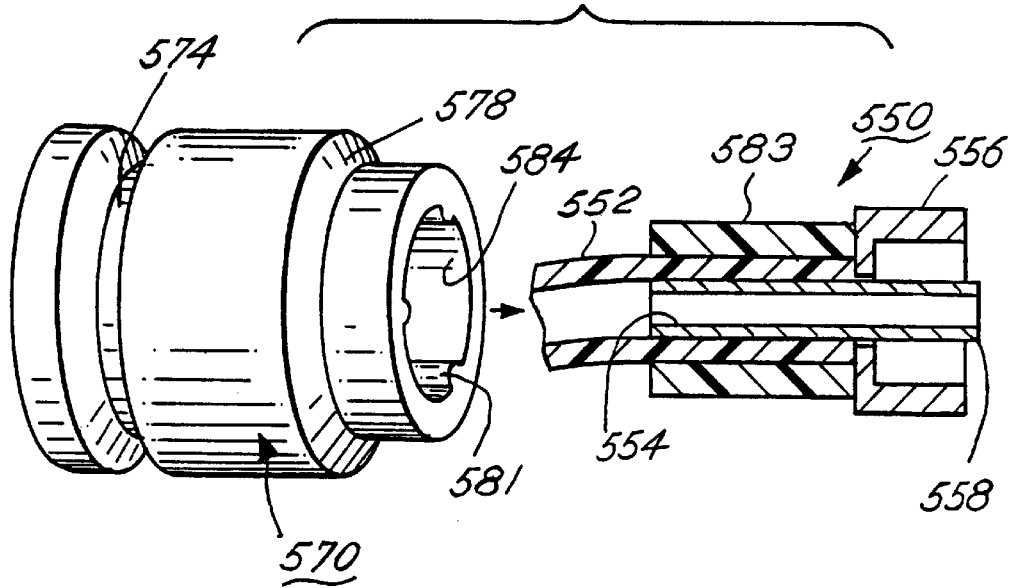
FIGS. 38E–G are illustrations of alternative constructions of the connector of FIG. 38A.
Figure 38F:
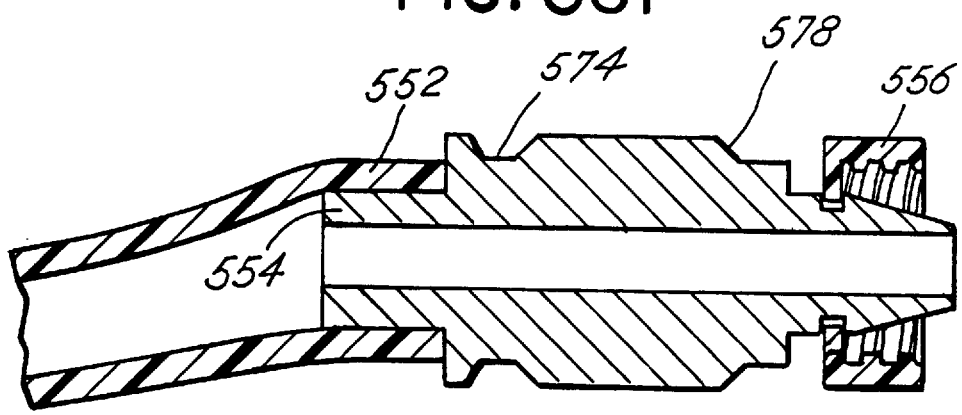
Figure 38G:
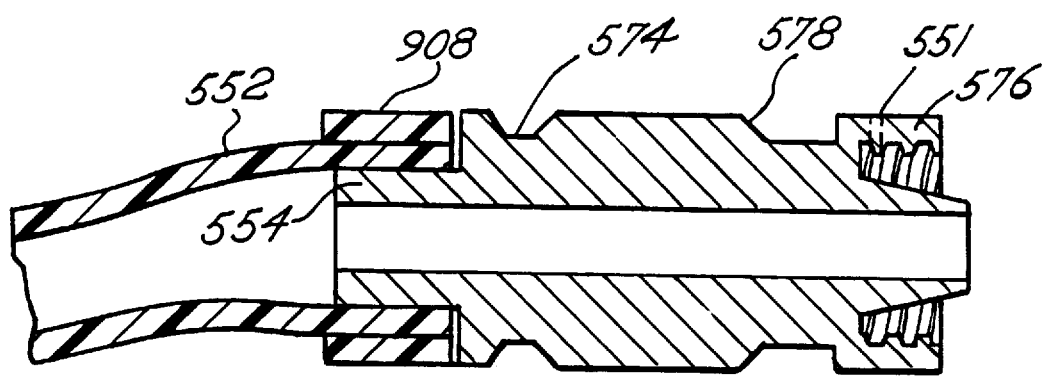

Referring to FIG. 38A, the outer and inner pieces 570 and 550 are secured together by inserting the outer piece 570 over the end of the tube 552 and firmly pressing the outer piece 570 onto the inner piece 550 (see arrow, FIG. 38A) such that the interior region snugly compresses the silicone tube 552, resulting in the construction shown in FIG. 38D. Alternatively, and referring to FIG. 38E, oversleeve 583 comprising a short tubing segment can be installed over the end of the tube 552, and the interior surface 584 can have 3 or 4 longitudinal ribs 581 projecting inwardly from the interior surface 584 that securely grip the tube segment 583 and tube 552 when the second piece 570 is snugly inserted over the male luer 550. Alternatively, the outer and inner pieces 570 and 550 could be formed as a single integral unit, with tubing port 554 extending rearwardly past the end of the cylindrical housing 572 to allow insertion of the end of the tube 552 onto the tubing port 554. See FIGS. 38F–38G.

The connection terminal of FIG. 38D is applied to the ends of the arterial and venous lines 432 and 492. The terminals are inserted into the preferred manifold port design, shown in FIGS. 39A–C. In FIG. 39A, the connection port 499 there illustrated is the same as the other ports 497 and 493. The port 499 is shown in a elevational view in FIG. 39A, and end view in FIG. 39B, and in a sectional view in FIG. 39C. The connection terminal of FIG. 38D is installed in the connection port 499 as shown in FIGS. 39D and 39E.

Referring to FIG. 39A, the port 499 consists of a housing 632 defining axis 661 with a flange 634 for mounting the port 499 to the disinfection manifold 494 housing (or perhaps to the side of the machine if the disinfection manifold is arranged as an array of ports). Screw threads 636 are provided for accommodating a threaded nut for securing the housing 632. Six apertures 638 are circumferentially spaced about the housing 632 with steel bearings 637 placed therein. Upper and lower projection elements 640 lock the knob 641 in place when the knob 641 is pushed against the force of the biasing spring 643 in the direction of the flange 634 and rotated. The notch 642 retains a retaining ring 695 for knob 641 in place. An elastomeric 0ring 650 is placed in the interior 654 of the port 494. The tube end 644 of the port 644 includes an optical detector comprising a light generation unit 646 and a sensor 648 with a lead going to CPU 610. Sensor 648 detects the presence of a connection terminal within the port 499. The tube end 644 accommodates a silicone tube (such as line 289A) in the manner described below in conjunction with FIG. 24.

Figure 40A:
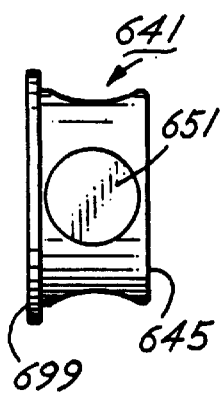
FIGS. 40A–40E are several views of the knob 641 of the port 499 of FIG. 39E.
Figure 40B:
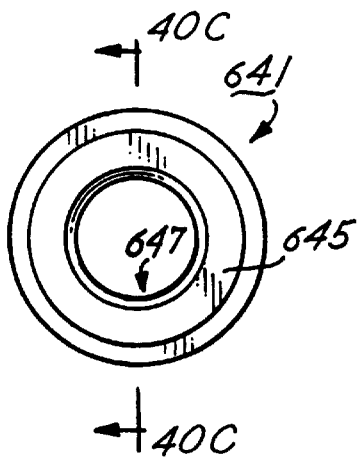
Figure 40C:
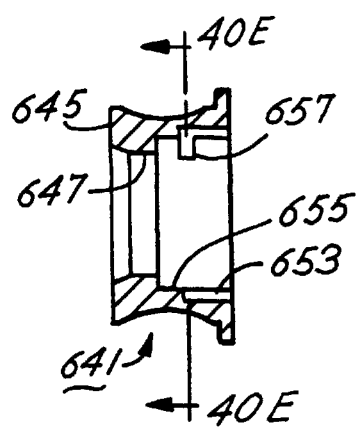
Figure 40D:
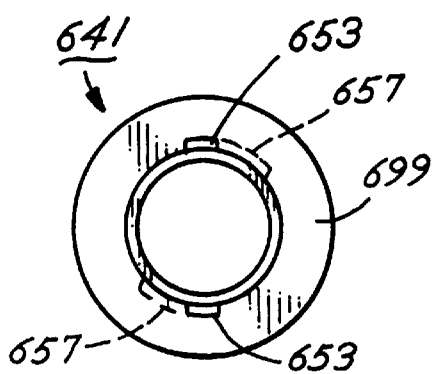
Figure 40E:
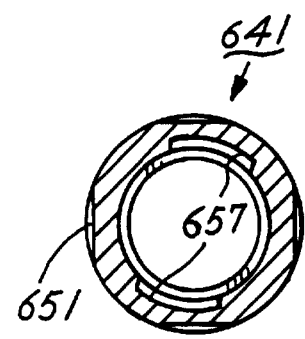

Referring to FIGS. 40A–40E, the knob 641 is shown isolated from the rest of the port 499. Knob 641 is shown in a side elevational view in FIG. 40A, with surface 699 oriented towards flange 634 and surface 645 oriented towards the outside as shown in FIG. 39E. FIG. 40B is an end view of the knob. FIG. 40C is a sectional view of the knob along the line 40C–40C of FIG. 40B. FIG. 40D is an opposite end view of the knob, with recessed portions 653 fitting over projections 640 of FIG. 39A. FIG. 40E is a sectional view of the knob 641 along the line 40E–40E of FIG. 40C. Races 657 accommodate the projections 640. The outer turn of the biasing spring 643 seats against the inner wall 655 of the knob. The spring biases the knob 641 to an outer position. The knob 641 locks on to projections 640 when the knob 641 is pushed to an inner position such that the projections 640 pass into recessed portion 653, and the knob is turned such that projections are rotated into Mace regions 657.

Referring to FIGS. 39D and 39E, the connector assembly of FIG. 38D is shown installed in the port 499. To establish the connection, the user inserts the connector 550, 570 into the port 654. To lock the connector 550, 570 in place, the user pushes the knob 641 against spring 643 such that portion 647 is positioned over the bearings 637, pushing the bearings 637 radially inward into notch region 574 of the outer piece 570. The shoulder 578 seats against the O-ring 650, with male luer 550 projecting into the region 652 of the port 499 where it can be sensed by the sensor 648. The knob 641 is rotated clockwise over the projection 640 (FIG. 39B) into a locked position. The bearings 637 are securely positioned within the notch 574 of the outer piece, preventing removal of the connection assembly 550/570.

When the connector assembly 550/570 of FIG. 38D is installed as Van in FIGS. 39D and 39E, it will be appreciated that complete disinfection of the interior and exterior surfaces locking hub 556 is accomplished when disinfection fluids are circulated within the port 499. In particular, if the patient contaminates (as by touching) locking hub 556 or spout 558 of the male luer 550 when disconnecting from the arterial or venous lines from the fistula needle, these surfaces of the male luer 550 are subject to hot water disinfection when the connector 550, 570 is installed on the port 499 during the disinfection cycle. Moreover, by reason of the clamping engagement of the outer piece 570 onto the tube 552 and seating of the shoulder region 578 of the outer piece 570 against the 0-ring 650, and the locking engagement of the outer piece 570 to the port 499, fluids will not escape past the O-ring 650 into the chamber 654.

Figure 14A:
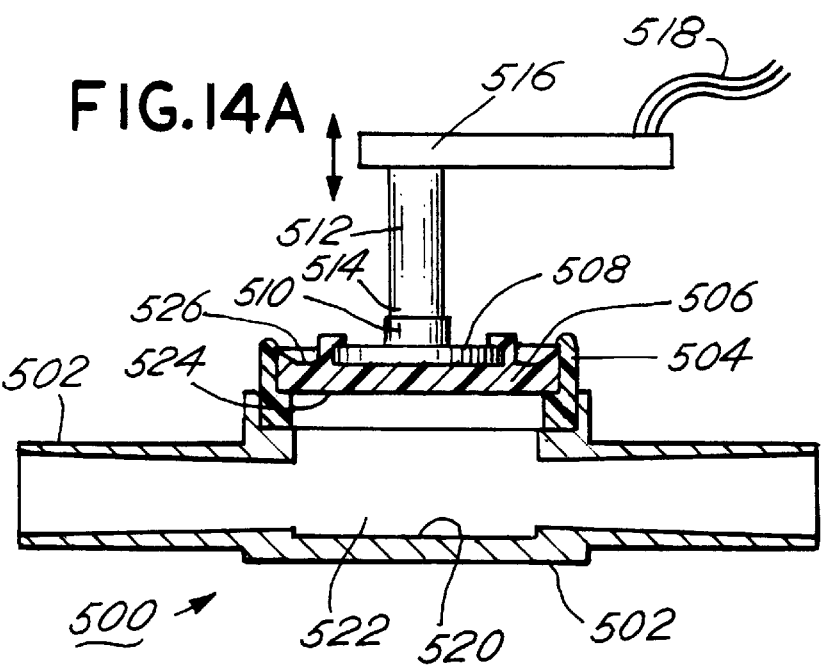
FIGS. 14A–14B are several views of the noninvasive pressure sensor 500 of the extracorporeal circuit module 28 of FIG. 13.
Figure 14B:
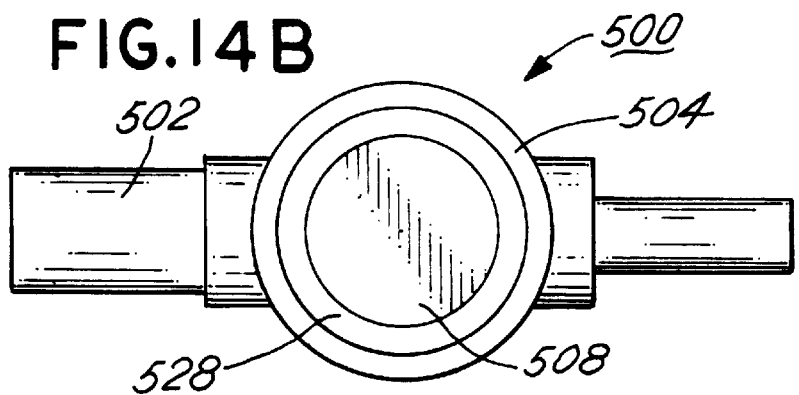
Figure 14C:
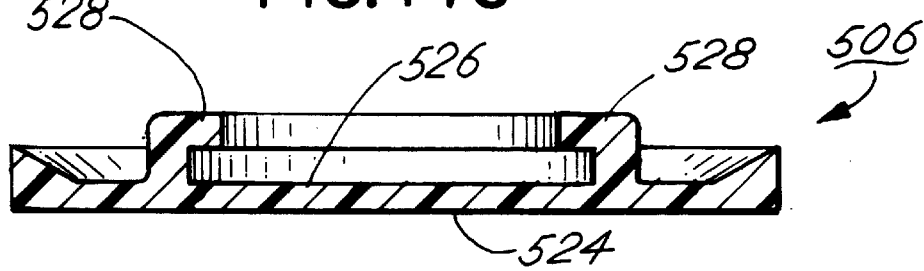
FIG. 14C is a sectional view of the diaphragm of FIG. 14A.

The pressure sensors 500A–C of FIG. 13 are of the same design, which is illustrated in detail in FIGS. 14A–14C. FIG. 14A is a cross-section view of the sensor 500, FIG. 14B is a top plan view of the sensor 500 in an assembled condition, and FIG. 14C is a sectional view of the diaphragm element 506. The sensor 500 includes a housing 502 and a retaining ring 504 which retains the diaphragm 506. The diaphragm 506 is placed opposite a wall 520. The diaphragm 506 is a preferably a circular resilient silicone membrane (or the equivalent) having an upper surface 526 and a lower surface 524 in contact with fluid within the chamber 522 of the sensor 500. A circumferential retaining rim 528 integral with the upper surface 526 of the diaphragm 506 reins a metal disk member 508 on the upper surface 526 of the diaphragm. The magnetic metal member 508 is placed into contact with a fret 510 mounted to the distal portion 514 of a rod 512. The metal member 508 may be coated to prevent corrosion or leaching of chemicals. It could also be made from plastic impregnated with metal. The metal must be magnetic. The rod 512 includes a lever member 516 connected to a strain gauge 518 that measures the back and forth movement of the rod due to the movement of the diaphragm 506 caused by pressure variations in the chamber 522. If a ferromagnet is chosen for the magnet 510, the magnet 510 is in continuous contact with the metal member 508. When the magnet 510 is an electromagnet, the magnet 510 would come into contact with the metal member 508 when the magnet is energized by an electric current.

The required magnetic force per unit area for the present application is about 11.6 pounds per square inch. For a disc 508 with a diameter of 0.441 inches, the preferred design, the required magnetic force is 1.77 lbs. The ideal force is a little greater, about 2 pounds.

The pressure sensors 500A, 500B monitor the pressure in the arterial line 432. If for some reason the arterial fistula needle gets accidentally positioned against the wall of the patient's blood vessel, the pressure will generally drop. The CPU 616 (FIG. 16) monitors the readings of sensors 500A, 500B and, if the pressure drops, it prompts the patient to move about to free up the needle or adjusts the blood pump 458 to bring the pressure to acceptable limits.

The efficiency of a dialyzer in removing toxins is maximized if the dialysis time is made as short as possible. The faster clearance of urea requires a faster flow rate of the patent's blood. We achieve a faster flow rate by taking advantage of a lower limit of pressure to be monitored by pressure sensor 500B that is safe for conducting dialysis. This pressure limit would be set by the patient's physician. As long as the pressure is above this limit, the pump rate of the blood pump 458 is gradually increased. If the pressure drops below the limit, the blood pump is slowed or stopped if the pressure fails to rebound. When the pressure rebounds, the pump is speeded up. This feedback control of a blood pump 458 by pressure monitors in the arterial Line will permit the system to generally shorten the dialysis time, to inform the patient of the expected time for dialysis, and to update the time based on any significant slowing or speeding of the blood pump 458. During this process, the backup pressure sensor 500A provides data in case of a malfunction in sensor 500B. Ordinarily, the pressure sensors 500A and 500B have the same readings. The pressure sensors 500A–C are calibrated against the reference sensor 410 in the dialysate circuit 402 as described below in conjunction with the pressure test of the extracorporeal circuit.

The blood sensors 446 and 486 are of the same basic design as the blood leak detector, but without the beam splitter and reference photodetector. The sensors 446 and 486 serve two purposes: (1) to detect blood when blood is first introduced into the extracorporeal circuit 400, thereby permitting calculation of the time elapsed during dialysis, and (2) permitting automatic rinse back control by automatically ending the rinsing back of the blood when the light transmission levels detected by the sensors 486 and 446 rises to a threshold value. As dialysate (or saline) is pumped through the dialyzer 404 during rinseback, the blood concentration in the lines 432 and 492 diminishes. When the blood concentration has been diluted to a threshold level, as determined by the blood sensors 446, 486, rinseback is deemed to have been completed. Clamps 444, 490 close, the blood pump is stopped, the input and output valves 414 and 416 for the dialyzer 404 close, and bypass valve 412 opens. During rinseback, the time and flow rate of the ultrafiltration pump 242 and blood pump 458 must be coordinated to insure equal pressure in the lines 432, 492. Generally, the ultrafiltration pump 242 pumps at twice the pump rate of the blood pump 458. This creates the pressure differential in the dialyzer 404 and a split flow of blood/dialysate in the arterial and venous lines of the extracorporeal circuit 400. Further, by knowing the flow rate and the volume of blood in the extracorporeal circuit 400, it is possible to determine the time for rinseback and blood can be automatically rinsed back without monitoring the concentration of blood in the arterial and venous lines. As another alternative, the blood may be rinsed back with saline from a saline bag with blood concentration measured in the venous line. This technique is discussed in detail below.

Leakage from the various lines and hardware components of extracorporeal circuit module 28 out of the tubing or hardware components is indicated by a leak path 430 (dotted lines). In use, the module 28 is placed above the other modules of the machine 22. A suitable drain and drain tube are provided from the extracorporeal circuit module 28 to the bottom of the housing of the entire machine 22, where such leakages may sensed by the fluid sensor in the catchment basin of FIG. 6. Alternatively, a blood sensor and fluid leak detector may be installed in the base of the extracorporeal circuit module 28 for leakage detection in situ.

The tubing (lines) used in the various modules 20, 24, 26, 28 is preferably a silicone tubing, as silicone tubing is biocompatible, translucent, susceptible to disinfection by hot water, oxidation chemicals and other disinfecting chemicals, and has a long operational life. Note, however, for the section of tubing used in the blood pump 458 we prefer to use a tubing that has superior anti-spalling characteristics, such as the PharMed™ polyolefin-based thermoplastic elastomer tubing from Norton Chemical, or the equivalent.

Silicone tubes are inert to most bonding solvents, so a way of fastening the tubes to the hardware was invented. A preferred technique for connecting the silicone tubes to the various hardware or rigid components of the machine (such as the pumps, valves, thermistors, tanks, filters, etc.) is shown in FIGS. 24A and 24B. A generic silicone tube 900 is shown connected to an arbitrary piece of hardware 902 by insertion of the free end of the tube 906 over an entry port 904 for the hardware 902. To keep the free end 906 securely installed on the port 904, we use a short section of tubing 908 typically having the same diameter as the tube 900 and insert the segment 908 over the other end 901 of the tube 900, spread the segment 908 apart with any suitable implement such as a tubing expander, and thread the segment over the tube to the end 906 until the segment 908 covers the port 904 and end 906, as shown. An alternative method of making the clamping connection is to first thread the segment 908 over the free end 906 of the tube 900, expand the segment 908 and end 906 of the tube with a tubing expander, and place the free end 906 and segment 908 over the port 904.

Different wall thicknesses and diameters of the segment 908 and tube 900 may still be used. The segment 908 can be the same tubing as the silicone tube 900. This construction gives good clamping results. We have found it particularly advantageous to have the segment 908 installed relative to the port 904 such that the outside end 903 of the segment 908 extends past the end 905 of the port, as shown in FIG. 24A. This construction creates a slight circumferential bulge 907 on the inside of the tube 900, preventing fluids from leaking around the edge 905 of the port.

V. The User Interface and Control Module 25

Referring now to FIG. 16, the user interface and control module will now be described. The module 25 includes a display 600 which displays messages and information concerning the status of the system to the patient. A touch screen 602 (or alternatively a keyboard) interfaces with the patient and is provided for inputting commands or information from the patient into a human interface (HI) board 608.

Indicators 604, including lights and audio indicators, and a speaker 606, alert the patient to abnormal conditions in the machine 22, and provide information as to the status of the modes of operation of the machine.

The module 25 includes a host central processing unit 610 connected via high speed digital data busses 611 and 613 to a driver board 612 and an analog board 614. The central processing unit 610 has an associated memory (not shown) that stores the operating software for the machine 22 and for other operational requirements, such as storing data from the sensors, and storing data input from the patients. Analog board 614 contains analog to digital converters for converting incoming analog signals from the passive sensors in the machine 22 into digital signals. The driver board 612 receives commands from the CPU 610 and sends the commands to the valves, pumps, heaters, motors, and other active components of the machines (represented by 620) to cause the components to change their status, e.g., commence or cease operation or change rate, as in the case of a pump, or open and close, as in the case of a valve. The signals from the passive components 622 of the system, for example, the conductivity sensors, touch button readers, pressure transducers, thermistors, provide their inputs to the analog boards 614 and 618. The CPU 610 and driver board 612 together act as a controller for the active components.

Analog board 618 provides digital information on bus 617 to a safety CPU 616. Safety CPU acts as watchdog of critical system sensors, and provides enable signals to the driver 612 that allow certain driver commands to issue to the active components 620 (such as enable signals to the motor to move the spike in the chemical applicator 260 to open the bottle when the correct indicator has been read on the side of the bottle). Communications between the CPU 616 and host CPU 610 are passed on data bus 609. The safety CPU 616 activates a buzzer if certain alarm conditions are present in the machine.

VI. System Operation

The operation of the constituent components of the machine 22 is controlled by a software program resident in the memory of the host CPU 610. FIGS. 17–23 illustrate in flow diagrams the individual routines and subroutines of the software (or, equivalently, operational sequences and modes of the machine 22). These routines and subroutines, the inputs and outputs to the CPU, and the operation of the other modules 24, 26 and 28 of the machine 22 are described in detail in this section.

The condition or state of the various sensors, valves, pumps and other components during the routines and subroutines of FIGS. 17–23 is illustrated in the tables of FIGS. 28–33. FIGS. 28 and 29 show the states of the components of the water pretreatment module 24. FIGS. 30 and 31 show the states of most of the components of the dialysate preparation module 26, with the states of several of the components of the dialysate circuit 402 and the components of the extracorporeal circuit module 28 shown in FIGS. 32 and 33. In these tables, the reference numerals of the components are listed on the left-hand side of the table, and the modes of the machine from FIGS. 18–23 are placed across the top of the tables. In FIGS. 34 and 35, the alarms for the machine 22 are listed on the left hand side of the tables and the modes of operation of the machine are placed across the top of the tables. Before describing the sequences and modes in detail, we describe below the system-in-progress and self-check routines that are performed when entire machine 22 is turned on or when power is restored after a temporary power interruption.

Upon power on, the machine performs self-checks necessary to ensure correct operation. If there is an error in any portion of the machine, the user is notified, as by displaying messages on the display 600, illumination of indicator or warning lights 604, or other suitable means consistent with FDA/AAMI/IEC standards. An indicator light 604 for power is preferably provided, allowing distinction between the absence of power and a system failure. It is preferred that the machine 22 be set up with auxiliary equipment, such as a fax/modem for reporting the results of the dialysis treatments to a central monitoring station, a blood pressure cuff, a scale for weighing the patient, and heparin infusion apparatus. The self check routines should determine the status of these features as well.

After the self-checks have been performed, the unit 22 performs a cycle-in-progress check to determine whether it was in mid-process (e.g., clean, disinfect, dialyze) when power was withdrawn. If the system was in mid-process and the power-off time was minimal, the system will continue the process.

If the disinfecting process was being performed, the CPU 610 can be preprogrammed to either continue or display message for operator to press "Resume". Default is that it continues, showing status. When continuing, the temperature of the system must be checked. Preferably there is a method of determining, based upon time elapsed without power and the current temperature of the device, whether the heat cycle is to be merely continued, lengthened, or completely rerun with a possible flush. The result must be that the disinfection cycle achieves the required limits of bacterial presence.

If the tank 202 was being filled, the CPU determines, based upon time elapsed without power, whether the existing water should be drained or whether the fill should be continued from the existing level. If bacteriologically safe to continue from existing level, the system continues filling, showing status. If not safe, the system drains and begins filling again. Depending upon time elapsed, it may be necessary to rerun the disinfect cycle.

If the dialysate was being mixed, the system determines, based upon the time elapsed without power, whether the existing batch is "safe" from bacterial growth and precipitation. If not, the operator is to be notified that the batch must be discarded. Preferably, the system is user programmable as to whether this is an audible as well as visual alarm. Default is audible as well as visual. If "safe", the mixing process continues, showing status.

If the extracorporeal circuit was being primed, the system determines, based upon the time elapsed without power, whether the existing prime is "safe" from bacterial growth and precipitation. If not, the operator is to be notified that the prime must be disregarded, and that an entirely new batch of dialysate must be prepared. If "safe", the priming process continues.

If the clearance test process was being performed, the system notifies user that valid clearance test data could not be obtained (only the sophisticated user may be interested, but the treatment report given to the center should indicate the lack of clearance test data). If a short enough time period has elapsed the system will continue dialyzing against the blood side until a proper electrolytic concentration and temperature are assured on the blood side. If too much time had elapsed, the system notifies the user that the prime must be disregarded, and that an entirely new batch of dialysate must be prepared.

If the initiate dialysis process was being performed, the system determines, based upon the time elapsed without power, whether the existing prime is "safe" from bacterial growth and precipitation. If not, the operator is notified that the prime must be disregarded, and that an entirely new batch of dialysate must be prepared. If "safe", the system continues recirculating the dialysate and maintaining its temperature.

If the dialyzing process was being performed, the system checks to see if bloodlines are connected to the machine. If bloodlines are connected to the machine, it determines time elapsed since removal of power. If safe time for bacterial growth, it asks if it should begin a cleaning cycle or if the user wants to reconnect. The system should only allow patient re-connection (and/or allows dialysate to be taken out of bypass) when the dialysate is at the correct temperature and conductivity. If the temperature gradient no longer allows for separation (if that method is used), it must account for this in reporting of therapy adequacy. If too much time elapsed for the dialysate to be "safe", the system asks to begin cleaning cycle. It may be programmed to begin automatically, as long as bloodlines 432, 492 are connected to the machine at 495, 497 (FIG. 13). If the bloodlines are not connected to the machine, (i.e., probably connected to the patient), the system asks the patient if they wish to resume dialysis, rinse back blood, or merely disconnect. If resuming or rinsing back blood, it notifies the user that they are to verify that safety clamps are put back in operating position (i.e. not opened manually). The system also verifies the temperature and conductivity of the dialysate. If the patient is continuing treatment, the treatment continues from where it was interrupted.

If the rinsing back blood process was being performed, the resume procedure is the same as the dialyzing process.

If the waiting for patient disconnection process was being performed, the system checks to see if the bloodlines are connected to the machine. If not, it ask the patient to disconnect. If so, the system asks to start the cleaning cycle; but it could be programmed to start cleaning automatically if the bloodlines are connected to the machine.

If the taking of blood pressure was being performed, the system begins blood pressure measurement again. The system looks to see the time elapsed since power was removed. The system may need to delay the number of minutes before retaking the blood pressure, due to rebound in the patient's body.

Figure 17:
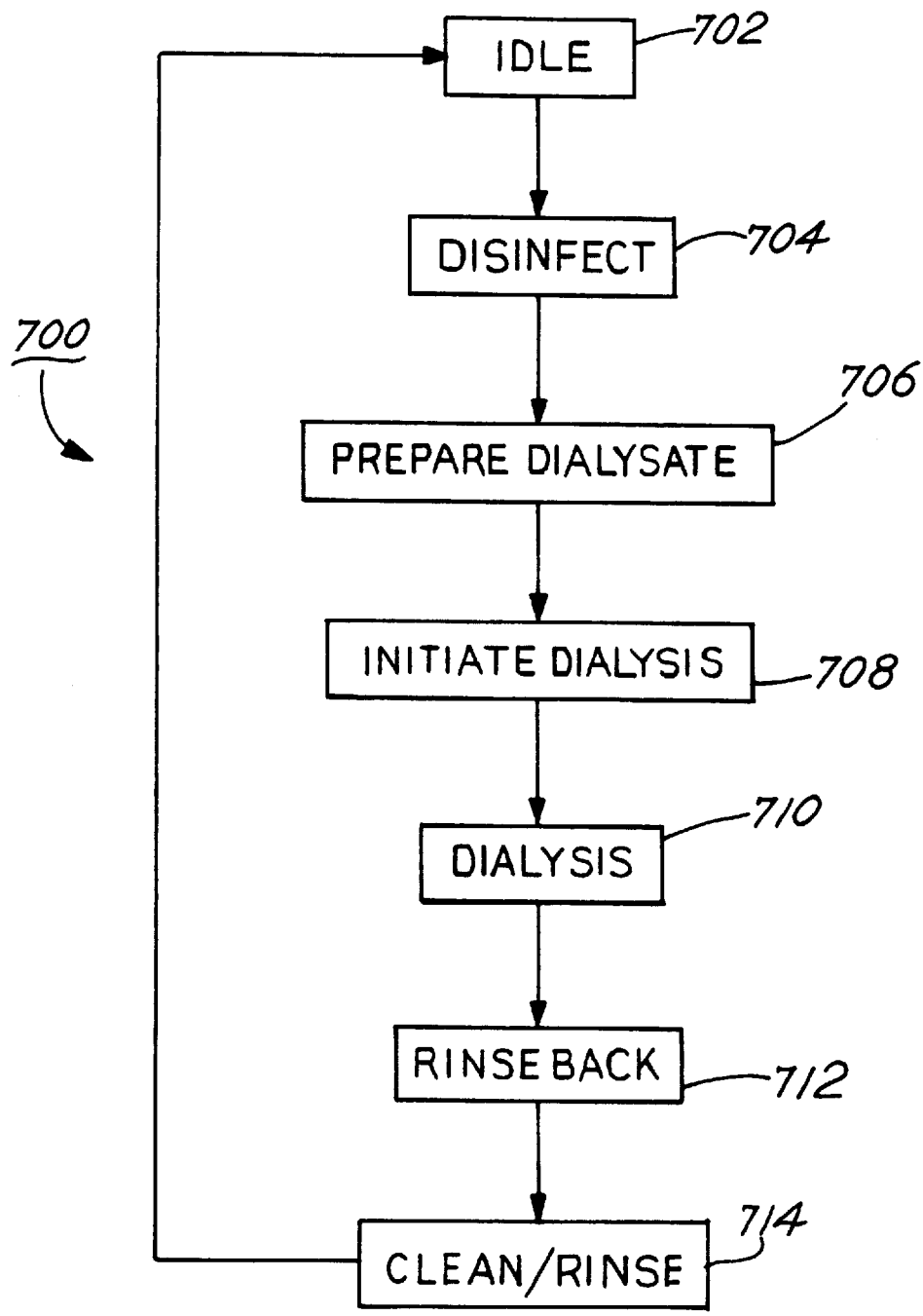
FIG. 17 is a flow diagram of the sequence of steps of the operation of the machine.

Referring now to FIGS. 16 and 17, after the system and in-progress checks have been performed, the system enters an idle state 702. An overview of the sequences of operation of the machine represented by FIG. 17 is described here. In the idle state 702, the machine 22 waits for a user input to commence dialysis. The machine 22 monitors the time clap since the last dialysis treatment. If the time since the last disinfection is greater than 48 hours, the machine enters a disinfect sequence 704. In the disinfect sequence 704, the entire machine is disinfected with hot water of a temperature of greater than 80 degrees C. for a period of at least an hour. If the thermistors in the modules 24, 26 and 28 report temperatures of greater than 80 degrees C. to the CPUs 610 and 616 for one hour, the machine initiates the prepare dialysate sequence 706. After the dialysate has been prepare, the machine commences the initiate dialysis sequence 708. When the priming of the extracorporeal circuit has been completed, the machine enters a dialyze sequence 710, where blood and dialysate are circulated to through the extracorporeal circuit and dialysate circuits 400, 402, respectively. When the ultrafiltration volume, KT/V parameter and dialysis time objectives have been met for the dialysis session, the machine commences the rinseback sequence 712, in which remaining blood in the extracorporeal circuit 400 is returned back to the patient. When this sequence has been completed, a clean and rinse sequence 714 is performed. After the rinse has completed satisfactorily and waste fluids have been flushed from the machine out the drain line, the machine returns to the idle mode 702 and waits for a command or the scheduled treatment time to occur and repeats the process.

It should be further noted that after a dialysis session has been completed, the arterial and venous lines, 432 and 492 (FIG. 13) are connected to their respective ports 497, 499 of the disinfection manifold 494. This connection provides a pathway for reverse osmosis water from the dialysate preparation module 26 to be introduced into the extracorporeal circuit 400, since the ports 497, 495 are connected to lines 289a and 236a (FIG. 6), linking the two modules together. This connection is important for performance of a number of specific functions relating to the extracorporeal circuit as described later.

It should also be noted that the disinfection temperature of the hot water (80 degrees C.) and the time for the hot water circulation throughout the machine 22 (1 hour) is not the only possible choice. The achievement of high level disinfection of fluid circuitry with water is a function of the water temperature and the length of time of hot water circulation. Hotter water will require less time for circulation and cooler water more time. In practice, a high level disinfection temperature will generally be determined or selected in advance and controlled by the operation of the water heater 228 in the machine and strategically placed thermistors, and the circulation time controlled by a clock in the CPU of the control module 25 and the operation of the pumps and valves of the machine.

A. Disinfect Sequence 704

Figure 18:
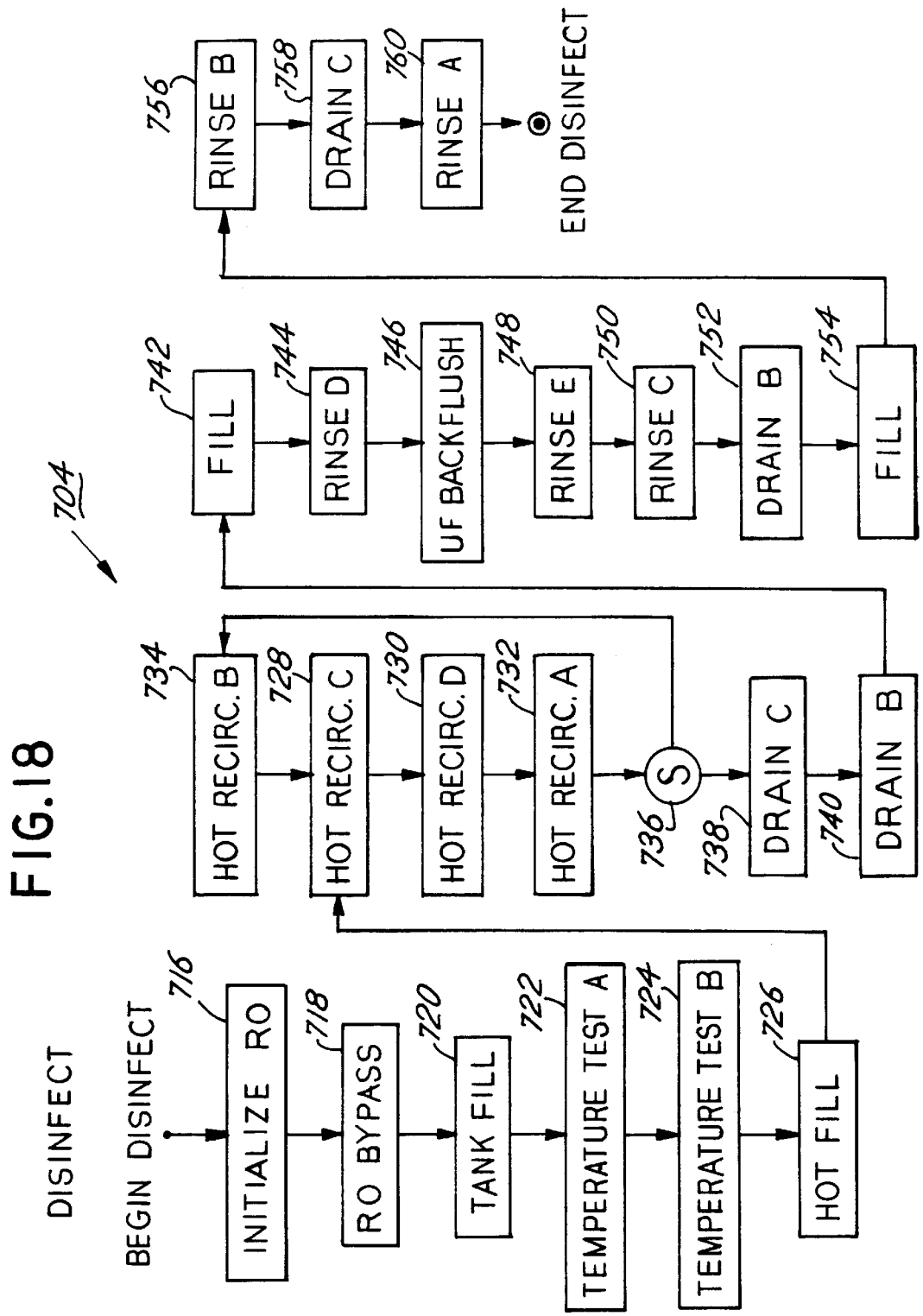
FIG. 18 is a flow diagram of the sequence of events during the disinfect step of FIG. 17.

FIG. 18 is detailed flow diagram for the disinfect sequence 704. During this sequence, the system decontaminates the dialysate preparation, water treatment, and extracorporeal dialysis modules, 26, 24, 28 respectively, within a bacteriologically acceptable window prior to the next treatment. Reference should be made to FIGS. 5, 6, 13 and 18 in the following discussion.

At step 716, the system checks to see that the chemical loading mechanism 260 is closed (i.e., the spike is in the lower position) and that the drain outlet of the machine 22 is connected to a drain source. The valve 72 in the water treatment module 24 is switched to allow water to enter the water filtration unit 84 (FIG. 5). Pressure sensor 98 is monitored to see if water pressure is present at the inlet of the reverse osmosis filter 100. If the water pressure is below a specified level, an indicator or alarm is activated. The pressure drops across the primary and secondary pre-filters are calculated. The reverse osmosis filter output valves 112, 108 and 80 are directed to drain water to the drain line 71. The feed side of the reverse osmosis filter 100 is flushed with water.

At step 718, the reverse osmosis filter 100 is put in a mode to create filtered water. The RO filter 100 valves are directed to bypass to drain. The filter unit 84 is then bypassed with bypass valve 83. Valve 81 is toggled a number of times to prime the recirculation loop (lines 110 and 116). The RO filter 100 valves are directed to bypass to drain. The system waits until the rejection conductivity exceeds a threshold level.

At step 720, the RO filter 100 is placed in a generate product mode. The RO filter 100 inlet and outlet conductivity and inlet pressure are monitored and an alarm is sounded if necessary. The tank 202 is then filled with water, line 206 and 209 (FIG. 6) are primed via valve 232. The UF pump 242 primes the dialyzer 404 via the valve 236 and lines 240, 422. The valves in module 26 are then directed to prime the pyrogen/ultrafilter 234 (not through the dialyzer 404) back to the tank 202. The UF pump 242 is then stopped, and the dialyzer 404 is primed in the forward direction.

At step 724, the blood pump 458 is operated and the valves in the module 26 are directed to transfer water from the tank 202 through the pyrogen/ultrafilter 234 to the dialyzer 404. The similarity of the thermistor readings of thermistors 408, 424, 216, 230 are compared and an alarm is activated if necessary.

At step 724, the RO filter 100 is directed to produce water. The valves in modules 24 and 26 are directed to send filtered water to the tank 202. The valves of module 26 are directed so that water from the tank 202 goes through the pyrogen/ultrafilter 234 and back to the tank 202. The valves are directed so that water bypasses the dialyzer 404. The similarity of the thermistor 408, 424, 216, 230 readings are compared and an alarm is sounded if necessary.

At step 726, the CPU 610 begins accumulating time data for the thermistors. Valve V9 and check valve CV12 are primed using UF pump 242. The RO filter 100 is directed to produce water and fill the tank 202. The heater 228 is directed to heat water to 85 degrees C. The valves are directed so that water bypasses the filter 234 and backfilters through the dialyzer 404 through valve 416. The blood pump 458 is turned on in the reverse direction to recirculate water through the extracorporeal circuit 400. Heated water is sent through the chemical applicators 260 and through valve CV9. When fluid sensor 288 senses a full tank 202, the RO filter 100 is directed to an idle mode. Water is directed through the filter 234 and dialyzer 404. The UF pump 242 is run in reverse at 500 ml/min with water sent through the chemical applicator nozzles 350 until 3 liters of water remain in the UF tank 244. The RO filter is directed to produce water and fill the UF tank 244. The UF tank level sensor LUF is monitored and the UF tank is filled, with sensor 288 triggering, indicating the tank 244 is full. The RO filter is stopped. At the end of this mode, the tank 202 is filled with RO filtered water at a temperatures of at least 80 degrees C.

At steps 728, 730, 732, and 734, the heated water is circulated throughout the water treatment module, dialysate preparation module, and extracorporeal circuit module for at least an hour. The paths A, B, C, and D indicate that due to the particular valving and fluid line network in the machine, the water cannot be passed through every fluid circuit at once, and that certain flow paths must be disinfected first before others can be disinfected.

Step 736 indicates that in the event that any of the thermistors report a temperature of less than 80 degrees C., the water is heated fir and the cycle of steps 734, 728, 730 and 732 is repeated. As an alternative, the water could be heated additionally above 80 degrees C. and the flow path affected, e.g. flow path "B", repeated a second time. As another alterative, an alarm could be activated or a chemical disinfection mode could be entered if the high level disinfection is not attained.

After the disinfection cycles have been performed, the machine enters a drain mode 738, where fluid is directed from the UF tank 244 through the dialysate module 26 to the drain line 107 in water treatment module 24. When the LUF sensor reads 0, mode 740 is entered, in which tank 202 is drained.

The machine then enters a fill mode 742, in which the RO filter 100 sends water to the tank 202. In rinse mode 744, water is directed from the tank 202 through the dialysate circuit 404 and back to the UF tank 244. When the fluid sensor 288 at the top of tank 244 detects fluid, the RO filter 100 is set to an idle mode.

At step 746, the UF pump 244 is turned on and water is directed from UF tank 244 though the dialysate circuit 400 back through the pyrogen/ultrafilter 234.

At step 748, water is directed through the sprayer 205 in the tank 202. Water is then directed from the UF tank 244 to the extracorporeal circuit 400 and back to the tank 202 until the UF tank 244 is empty.

At step 750, water is rinsed in the tank 202 via sprayer 205. At step 752, water is directed from the tank 202 to drain. At step 754, RO water is sent to the tank 202. At step 756, the blood pump 458 is run in reverse at 75 ml/min. Water is directed through the dialyzer 404 and back to the tank 202 through the chemical ports in the loading platform 250. At step 758, water is drained from the tank 202. At step 760, the pump 212 speed is reduced to 300 ml/min. Water is directed from the tank 202 through the dialyzer 404 and the extracorporeal circuit 400 and then to drain. The system waits until the tank 202 level sensor reads 1 and the flow meter 241 reads less than 300 ml/min.

B. Prepare Dialysate Sequence 706

Figure 19:
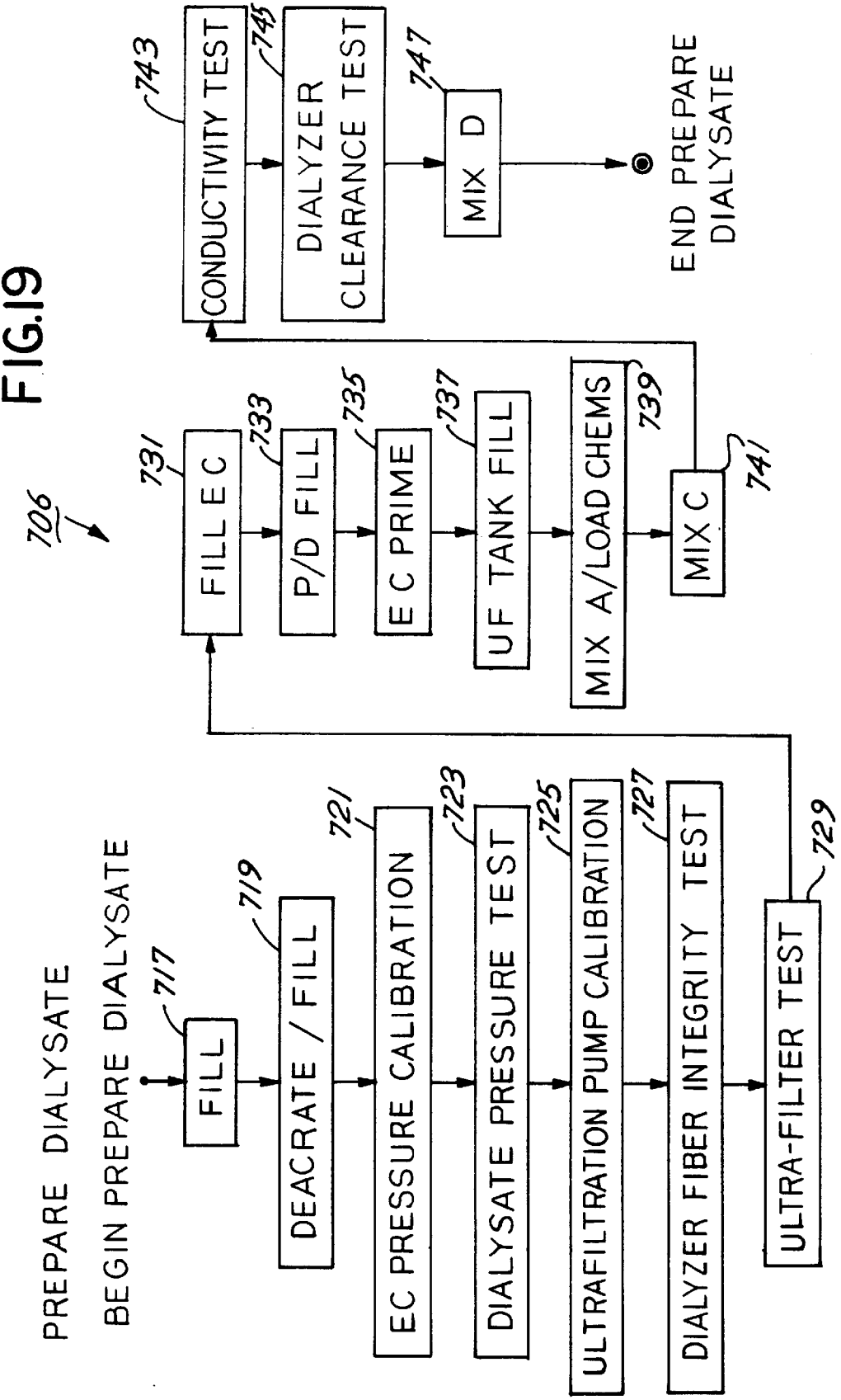
FIG. 19 is a flow diagram of the sequence of events during the prepare dialysate step of FIG. 17.

After the disinfection mode, the system enters a dialysate preparation sequence 706, described in detail in FIG. 19. At step 717, the process described with step 742 above is performed. At step 719, the RO filter 100 is placed in a produce water mode. The RO alarm monitoring RO conductivity in cell 106 is activated. RO filtered water is then directed to the tank 202. Pump 212 is run at top speed in the forward direction. The tank 202 is placed in a recirculation and deaeration mode, in which water circulates out the tank 202 through degassing line 209, through valves V9 and 220 and back to the tank via valve 232 and line 231 and valve V25. The temperature at thermistor 230 should read a temperature of 30 degree C. The UF tank 244 is filled with 500 ml of water using the UF pump 242. The tank 202 is filled with reverse osmosis water up to the level at which chemicals are added to the tank 202, and then the RO filter 100 is turned off.

At step 721, the pressure sensors 500A–C in the extracorporeal circuit are calibrated against pressure sensor 410 in the dialysate circuit. Pressure variations in the dialysate circuit 402 are achieved by moving volumes of fluid between the tank 202 and the ultrafiltration tank 244, with the introduction of fluid into the tank 202 causing an increase in pressure. Similarly, pressure variations in the extracorporeal circuit 400 are achieve by introducing additional volumes of fluid into the extracorporeal circuit via disinfection manifold 494. This calibration test is advantageous in that it permits the use of disposable, off the shelf pressure transducers to be used in the extracoporeal circuit 400. It also permits high accuracy of the monitoring of the blood pressure in the extracorporeal circuit 400 during dialysis. To accomplish this, the valves are switched to direct dialysate-side fluid through the dialyzer 404 and pressure sensor 410. The valves are switched to isolate the tank 202 from the dialysate pathway. UF pump 242 is run in reverse to direct fluid from the UF tank to the dialyzer 404 and the extracorporeal circuit and to pressurize the dialysate circuit 402 to 300 mm Hg. If the pressure sensors 500A–C in extracorporeal circuit 400 fail to pressurize or the rate of decay exceeds a predetermined limit, an alarm is activated, indicating a leakage in the extracorporeal circuit 400. Assuming no leakage, the pressure reading of sensor 410 is used to calibrate the pressure sensors 500A–500C in the extracorporeal circuit 400.

The UF pump 242 is then run in the forward direction, removing fluid from the dialysate circuit 402, and the pressures is stabilized at about 10 mm Hg. A second calibration of the pressure sensors 500A–C is then done, and gain and offset values for the sensors are determined. An alarm indicating a failure of the pressure sensors is activated. The UF pump is run in the forward direction until negative pressure is developed, and the additional calibration of the pressure sensors is performed. Additional negative pressure is generated and another calibration is performed. Then, UF pump 242 is run in reverse, the pressures are stabilized at 0 mm Hg. and the tank 202 is vented to atmosphere.

At step 723, a test the integrity of dialysate circuit and ultrafiltration control system is performed. When the test is initiated, the level of water in the tank 202 is up the to level of the chemical loading platform, the RO filter is in an idle mode and the arterial 444 and venous 490 clamps of the extracorporeal circuit 400 are open. The valves of module 26 are switched to direct water away from the dialyzer 404 and to isolate the tank 202. The fluid lines of the dialysate circuit 402 are completely full. This fluid circuit is a closed system, with valves 414 and 416 closed with bypass valve 412 open.

The ultrafiltration tank 244 contains some reverse osmosis water. The UF pump 242 is operated in the reverse direction to pump water into line 240 in the dialysate pathway. This increases the volume of water in the closed system, causing an increase in pressure. Pressure sensor 410 in the dialysate circuit 402 monitors the increase in pressure. Any failure or leakage in the system will be detected by the rate of decay in the pressure monitored by sensor 410, activating an alarm. The pressure in the extracorporeal circuit 400 is also monitored and slowly reduced with the blood pump 458.

At step 725, the ultrafiltration pump 242 is calibrated against the flow mete 241. Fluid is directed from the tank 202 through the UF pump 242 to the filter 234 and back to the tank 202. Valves V9 and 412 are pule to clear air from the lines of the dialysate circuit 402. The flow meter readings are monitored as the speed of the UF pump 242 is varied. A best fit calibration line from the readings of flow rate and UF pump speed is calculated in the CPU 610.

At step 727, a test of the integrity of the fibers in the dialyzer 404 is performed to insure that the dialyzer 404 does not have any leaks. We perform this test with air pressure, similar to the fashion in which the ultrafilter/pyrogen filter 234 is tested. To perform this test, the clamp 490 is closed and valve V14 is closed. Air is pumped by the blood pump 458 from the ultrafiltration tank 244 into arterial line 432 (via disinfection manifold 494) up through the dialyzer 404 to displace any fluid through valve 414 until the fluid is substantially removed from the lumen side of the dialyzer 404. The pressure sensor 500C in the extracorporeal circuit 400 monitors the pressurizaton of the dialyzer 404 and the pressure decay in the line 462. If the sensor 500C fails to record an adequate pressure, or the decay rate is too great, the dialyzer 404 is deemed to have failed the test and the user is alerted to the need to replace the dialyzer.

At step 729, the integrity of the pyrogen/ultrafilter 234 is tested. This test was described in detail above in the discussion of the dialysate preparation module 26.

At step 731, the extracorporeal circuit 400 is filled with water. The RO conductivity and pressure are monitored. The UF tank 244 is filled with approximately 1 liter of water using UF pump 242. The RO filter 100 is placed in an idle mode. RO water is direct through the dialyzer 404 from the UF tank 244 back to the tank 202 using the blood pump 458. Then, water is back-filtered through valve 416 while venous clamp 490 is pulsed to fill the air separating chamber 474 (FIG. 13). Valve Vie is pulsed to clear air from the arterial extracorporeal circuit line 432. When the UF tank 244 is empty, the clamps 444,490 are closed and the blood pump 458 is closed.

At step 733, RO water is pumped from the tank 202 to the dialyzer 404. The dialyzer 404 is bypassed for a short period of time and then water is backfiltered across the membrane of the dialyzer 404 into the extracorporeal circuit 400 and back to the tank 202 to prime the extracorporeal circuit 400. During these steps, the blood pump 458 is run in reverse during bypass and then forward during backfiltration.

At step 735, the extracorporeal circuit 400 is flushed with fresh reverse osmosis water to eliminate air and bubbles from the circuit. The automatic priming process may be implemented as a sequence of steps pre-, during, and post-dialysate preparation, depending on the most effective and efficient way to achieve priming and dialyzer clearance test requirements. A new extracorporeal circuit will be required when the dialyzer 404 is determined to have a leak or unacceptable performance during the clearance test, in which case replacement occurs after the batch of dialysate has been prepared and the clearance test has been run, or, if the dialyzer clogs during treatment, in which case replacement occurs mid-treatment, or when the dialyzer was determined during the previous treatment's clearance test to be adequate for that treatment only and replacement should have occurred prior to the preparation of the new batch of dialysate and prior to the new clearance test.

During the prime mode 735, water is pumped through the dialyzer 404 (with valves 412, 414 closed and valves 416, 232 and V15 open). The extracorporeal circuit lines are put in a recirculation mode with V20 closed. To shear any remaining bubbles from the fibers of the dialyzer 404, pressure surges (or spikes) are induced in the arterial line 432. This is accomplished by opening and closing in rapid succession the clamps 490 and 444 and varying the flow direction of the blood pump 458. Pressure is increaseed in the lines when the clamps are closed and the blood pump 458 continues to pump, and when the clamps are opened the release of pressure within dialyzer 404 shears the bubbles from the fibers. Valve 416 is also pulsed to cause backfiltration to shear bubbles from the fibers.

Priming is also assisted by periodic backfiltration of water across the dialyzer 404. The backfiltration of fluid across the dialyzer is also accompanied by the introduction of pressure pulses in the dialysate circuit 402. The pressure pulses in the introduction of fluid across the membrane causes air bubbles to be sheared off the blood side of the dialyzer membrane. The air bubbles are then conducted from the blood side of the dialyzer and out of the extracorporeal circuit 400. The dialysate is pumped at a high flow rate through the dialysate circuit 402, and a valve in the dialysate circuit is opened and closed to thereby introduce pressure pulses in the fluid. The backfiltration may occur in synchrony with the pressure pulses introduced in the dialysate circuit 402.

At step 737, the RO conductivity and pressure is monitored and the dialysate tank 202 is filled with RO water unless the level is above the level of the chemical loading platform 250. The UF tank 244 is drained. Water is pumped to the filter 234 and away from the dialyzer 404, with the water heated by heater 228 to 37 degrees C. The tank return valve V18 is closed and water is directed from the tank 202 though valve 236 into the UF tank 244 using the UF pump 242. The UF tank 244 is filled. The tank return valve V18 is opened.

At step 739, the RO conductivity and pressure are monitored and RO water is sent to tank 202 until the proper level for addition of dialysate chemicals is reached. The bottle 270 containing powdered chemicals is pierced by the chemical applicator 260, and chemicals are purged from the bottles 270 by periodic short bursts of water from the nozzles 350 in the applicators 260 (FIG. 12). The sprayer 285 in the loading platform 250 rinses the chemicals off of the shelf of the platform 250 into the tank 202. As water is circulated through the tank and outlet line 206, the conductivity sensor 218 monitors the conductivity of the solution. Additional water is added to the tank 202 if necessary. The additional dialysate chemicals in the second and third chemical bottles are then released onto the platform 250 by operation of the chemical applicators 260. The liquid chemicals are added just before the fluid level reaches the level of the nozzle 352 in the applicator 260. The tank 202 is then filled completely with water.

At step 741, the system enters a mix mode in which the dialysate chemicals are mixed in the tank 202. The chemicals are mixed in the tank using the process previously described. During the mixing mode, conductivity sensor 218 monitors the conductivity of the dialysate in the line 206 and reports the measurements to the CPU 610. A safe concentration of chemicals is verified by conductivity measurements in conductivity sensor 218 and/or by sampling the dialysate in sampler 210. Preferably the dialysate is circulated from the tank outlet, through the conductivity sensor 218 and back into the top of the tank 202 via sprayer 205 during the mixing process. When the conductivity of the dialysate remains constant for a sufficient period of time, the solution is deemed mixed. During the mixing process, the dialysate is not sent through the ultrafilter or dialyzer but rather is circulated from the bottom of the tank out line 208 through valve V9 to valve 232 and back via line 231 and valve V15 and sprayer 205.

At step 743, a conductivity test is performed with the purpose to verify that conductivity cells 426 and 218 have the same readings. Dialysate is pumped from the tank 202 through the ultrafilter 234 and dialysate circuit 402, through bypass valve 412 and back to the tank 202. An alarm is activated if the conductivity reading are not substantially the same, indicating a failure in one of the conductivity cells. Also, the readings of the thermistors 424 and 408 are compared, and an alarm is activated if the readings of dialysate temperature are not substantially the same, indicating a failure of one of the thermistors.

At step 745, a dialyzer clearance test mode is entered. Prior to conducting dialysis, the integrity of the dialyzer 404 and the urea transmission rate through the membrane of the dialyzer should be checked. On average, extracorporeal circuits are reused from 12–15 times before they must be discarded. In order to determine whether the extracorporeal circuit should be replaced, its clearance must be tested. We perform the clearance test after dialysate chemicals have been mixed in the tank 202, and with the ultrafiltration tank 244 filled with approximately 4 liters of reverse osmosis water heated to a temperature of 37 degrees C. The dialysate temperature is about 30 degrees C. The extracorporeal circuit 400 is filled with reverse osmosis water.

The machine 22 tests the clearance of the dialyzer 404 by taking advantage of several properties of the Na+ ion: the Na+ ion is about the same size as the urea molecule, that Na+ is the dominant cation in a dialysate solution, and that Na+ is very conductive and able to be monitored with precision with a conductivity monitor, such as the two noninvasive conductivity cells 218 and 426 in the dialysate preparation module 26. The Na+ ion is used as a substitute for urea. The conductivity sensor 218 measures the conductivity of the dialysate going into the dialyzer 404, and conductivity sensor 426 measures the conductivity of the dialysate coming out of the dialyzer 404.

The blood pump 458 continuously pumps pure reverse osmosis water through the blood side of the dialyzer 404 (i.e., single pass). The water flows from UF tank 244 through valve V13, through line 289 and 289A to the port 499 in the disinfection manifold 494 (FIG. 13) of the extracorporeal circuit module 28, then into the arterial line 432 and through the circuit 400 and dialyzer 404, out the venous line 492 to port 497 of the disinfection manifold 494, and back to the tank 202 via line 236 valve V21 and inlet 203. Simultaneously, pump 212 pumps fresh dialysate through heater 228 where it is heated to 37 degrees C. and pumped through the dialysate circuit 402 and back to the tank 202. At the end of the dialyzer clearance mode 745, about 500 ml of RO water remains in UF tank 244 at a temperature of 37 degrees C.

The measurements of conductivity are sent to the CPU 610 of the interface and control module 25. The difference in conductivity between the sensors 218 and 426 is a measure of the urea clearance of the dialyzer 404. As shown in FIG. 26, the conductivity measured by conductivity cell 426 drops when the process is initiated, but soon levels off. When the conductivity measured by cell 426 has leveled off, the clearance of the dialyzer 404 in units of ml of sodium cleared per minute can be calculated by the central processing unit 610. A minimum conductivity level 759 may be determined for the sensor 426, and if the sensor does not record a conductivity below this level at steady state, a clearance test failure may be deemed to have occurred.

An alternative method of determining whether the dialyzer needs to be replaced is to compare the clearance coefficient K for the dialyzer with the value of K when the dialyzer was new. Let $C_{in}$=Conductivity on inlet side of dialyzer, measured by 218, $C_{out}$=Conductivity on outlet side of dialyzer, measured by 426. Let K=$[(C_{in}-C_{out})/C_{in}]$ X flow rate in ml/min.]. Let $K_{init}$=the initial measurement of the clearance coefficient when the dialyzer was new. Before every dialysis session, $K_i$ is determined as set forth above. When $K_i \leq 0.9\ K_{init}$, the dialyzer is deemed to be in condition for replacement prior to the next treatment.

As a redundant safety measure, the machine 22 performs the clearance test twice before conducting dialysis. If the dialyzer 404 fails both times, a replacement message is displayed at the user interface advising the user of the need to replace the extracorporeal circuit and dialyzer 404 prior to the next dialysis. The CPU 610 records a failure of the dialyzer including the clearance value and the date at which the failure occurred.

At step 747, a mix mode is entered for the purpose of bringing the extracorporeal circuit 400 and UF tank 244 fluids up to the correct conductivity. Dialysate is circulated through the UF tank 244 with the temperature controlled to 30 degrees C. After a certain amount of time, the conductivity of the UF tank dialysate becomes stabilized, and an alarm is activated if the conductivity is outside of an expected range. The valves are switched to direct dialysate out of the tank 202 though the pyrogen/ultrafilter 234 through the dialyzer 404 and into the extracorporeal circuit by backfiltration. The extracorporeal circuit dialysate flow is directed through the disinfection manifold 494 back to the tank 202 with the assistance of the blood pump 458. When the extracorporeal circuit dialysate outlet conductivity has matched the inlet conductivity, backfiltration is ceased and diffusion across the dialyzer is allowed to occur, with valve 416 open. The fluid level in the tank 202 is lowered below valve V6 if necessary.

C. Initiate Dialysis Sequence 708

The initial conditions for the initiate dialysis sequence are the circulation of dialysate through the extracorporeal circuit at a correct and stable conductivity and temperature and the arterial and venous lines of the extracorporeal circuit ar connected to the disinfection manifold 494 with the blood pump running in the forward direction.

Referring to FIG. 20, patient assessment is made at step 860. An initiation screen is displayed on the display 600, and the patient is prompted to initiate dialysis. The display 600 displays a patient questionnaire, seeking input from the patient, such as their current pretreatment weight, standing blood pressure and sitting blood pressure, The weight and blood pressure of the patient is taken and the data is entered into the CPU 610. After the patient assessment steps have been performed, the system verifies that the saline bag 448 in the extracorporeal circuit is connected.

The system can be preprogrammed to dialyze to the following combination of parameters:

target KT/V per treatment, where K is the urea clearance of the dialyzer in ml of blood totally cleared in urea per minute, T is the treatment time, and V is the volume of distribution which is approximately equal to the total body fluid volume of the patient. The details of the correlation calculation between sodium and urea are set forth in the Howard et al. U.S. Pat. No. 5,110,477, which is incorporated by reference herein.

Minimum treatment time, regardless of whether the KT/V target was reached in a shorter amount of time.

Prescribed blood flow rate, with limits on maximum arterial and venous pressures;

Dry weights with limits also preprogrammed as a maximum rate at which fluid can be removed (weight is removed is then calculated by subtracting dry weight from preassessment weight and adjusting the additional fluid infused during prime, rinseback and at other times) or Fluid to remove, for example, in an acute setting, a removal amount may be required based upon infusion volumes rather than patient weight and the system will not be able to automatically calculate fluid removal from [weight minus dry weight], thus necessitating the operator to directly specify the amount of fluid to remove.

Additional prescription parameters will be set by the physician such as, particular dialyzer to be used, the arterial pressure limits, venous pressure limits, fluid removal rates, dialysis flow rate, temperature, heparin dosage, and so on.

At step 802, heparin access site preparation instructions are displayed on the screen 600. Heparin connection instructions from the patient's prescription are displayed. After the patient connects the heparin injection apparatus to an injection site in the arterial line 432, the user is prompted to input an OK.

At step 804, protective system tests am performed to insure safety of the dialysis process. The tests include: arterial and venous air bubble detectors, arterial and venous pressure tests (high and low), dialysate temperature and conductivity tests, and blood leak detector tests.

After these tests have been performed, the system at step 806 checks to see if the extracorporeal circuit is to be primed with saline or blood. If saline is used to prime the extracorporeal circuit 400, the user is prompted to begin saline prime. The user spikes the saline bag and the saline line is primed. The blood pump 458 circulates 500 ml of sine though the arterial and venous lines of the extracorporeal circuit, with the fluids emptied out of the venous line 492 into a suitable container. The blood pump 458 is then stopped and the clamps in the arterial and venous lines are closed.

A priming fluid can also be pumped through the extracorporeal circuit, connecting the patient to said arterial and venous lines of the extracoporeal circuit, and pumping priming fluid from the extracoporeal circuit through the dialyzer to said dialysate circuit. Then, blood is pumped from the patient into the extracorporeal circuit to the dialyzer and returned to the patient, thereby avoiding pumping of priming fluid into the patient. The priming fluid is pumped through the dialyzer by the UF pump in the forward direction and the priming fluid is returned to the ultrafiltration tank.

If blood is used to prime the extracorporeal circuit 400, the machine at step 808 prompts the user to insert the arterial fistula, unclamp the arterial fistula line, prime the arterial fistula line with blood, reclamp the fistula line and attach the fistula to the connector at the end of the arterial line 432. The venous connection is then made in similar fashion. If necessary, the user is prompted to connect line 482 to the pressure port 493 in the disinfection manifold 494. Dialysate is pumped through the dialyzer 404 to the UF tank. The blood pump 458 is run in the forward direction until a small negative pressure in the arterial and venous line is sensed. The extracorporeal circuit pressure alarms are enabled, the blood sensors are enabled and the arterial and venous clamps are opened. If the blood sensors in the arterial and venous lines do not detect the presence of blood within a predetermined time period, an alarm is activated. The level in chamber 471 is lowered with the venous clamp. After a small volume of blood has been drawn, the arterial clamp 444 is closed. The UF pump 242 is stopped and the valve V13 into tank 244 is closed. The user is prompted to confirm blood circulation. The air bubble detectors are enabled and the arterial and venous clamps are opened. The blood pump 458 ramps up to the prescribed blood flow rate.

D. Dialyze Sequence 710

Referring to FIG. 21, at step 820, the thermal boundary layer between old and new dialysate in the tank 202 is established in the tank 202. In the preferred embodiment, 1 to 2 liters of dialysate is heated to a temperature of 37 degrees C. and introduced into the top of the tank 202 in a nonturbulent manner as described in detail above. The heater 228 controls the dialysate temperature to the prescribed temperature.

The trans-membrane pressure at dialyzer 404 is adjusted to prevent any net water or dialysate transport across the dialyzer 404. Measurements of the blood pressure on the inlet and outlet on the blood side of the dialyzer 404 are made with the pressure sensors 500C and 775. (FIG. 13). The average pressure between these pressures is then computed The pressure in the dialysate circuit is measured at pressure sensor 410, and the pressure in the dialysate circuit is adjusted to match the average pressure in the blood side of the dialyzer 404. The adjustment of pressure is accomplished by operating the UF pump 242 in either the forward or reverse direction to pump fluid into or out of the ultrafiltration tank 244 into the dialysate circuit. By using a closed loop ultrafiltration system with a substantially non-compliant tank 202, the addition or substraction of fluid from the dialyzate circuit 402 (including the tank 202) adjusts the pressure in the dialysate circuit. The tank 202 need not be full during this process. This pressure adjustment technique prevents any unintended fluid transport across the dialyzer when dialysis commences.

After the pressure has been adjusted across the dialyzer, the patient's blood is dialyzed at mode 822. The dialysis sequence continues until the treatment time is up or the patient requests end of treatment. As the UF tank 244 is filled with the predetermined ultrafiltration volume for the dialysis session, the measurement of the volume of water removed from the patient is made by the level sensor LUF. As the patient's blood fills the extracorporeal circuit 28, the level of the air separating and pressure adjusting unit 472 may be adjusted. The blood detectors 446, 486 detect presence of blood in the extracorporeal circuit. Once blood flow has been achieved and venous and arterial pressures have been stabilized, the system remains in dialysis sequence until the treatment is complete or stopped by the user. The time of dialysis is measured and time remaining for the session may be displayed to the patient.

During the dialysis process, the membrane of the dialyzer 404 in the extracorporeal circuit 400 may be periodically backflushed (step 874) with fresh dialysate to remove any build-up of blood materials on the blood side of the membrane. This procedure increases the efficiency of the dialyzer 404, avoids the buildup of blood products in the dialyzer and prolongs the life expectancy of the dialyzer 404. The blood products building up on the membrane are momentarily forced off the blood side of the membrane by the dialysate flowing into the extracorporeal circuit 400, and then, when the back flushing ceases, incorporated into the blood flow, where they are carried out of the extracorporeal circuit 400 and back to the patient.

To accomplish backflushing of the dialyzer, fresh dialysate is taken from the tank 202 and passed through valve V9 up through the ultrafiltration pump 242, which is operational in the reverse direction. Dialysate is pumped out valve 236, through CV12, up line 223 and 226 to the pyrogen/ultrafilter 234 and up to the dialysate circuit 402 and into the dialyzer 404 with valve 414 open and valves 412 and 416 closed. During this time, the blood pump 458 is slowed. The bursts of dialysate through the dialyzer 404 preferably are between 15 and 30 seconds in length. The backflushing can be periodic during dialysis, or may occur one time or not at all, depending on whether the membrane of the dialyzer is performing efficiently. After the backflushing is completed, the UF pump 242 is stopped, valves 414 and 416 are closed and bypass valve 412 is opened, the blood pump 458 is ramped up to normal speed, the dialysate pump 212 is started again at the prescribed speed, valve 412 is closed and valves 414 and 416 are opened, the UF pump speed is recalculated and the UF pump is started up again in the forward direction at the proper rate. The above-described technique differs from that described in the Eigendorf patent, U.S. Pat. No. 5,259,961. In the '961 patent, flushing of dialysate through the dialyzer is described as for the purpose of flushing and filling the extracorporeal circuit.

In alternative steps 826 and 828, it will be seen that other physiologic solutions may be used to backflush the dialyzer by connecting the source of fluid to the dialyzer inlet line 418 and providing a suitable pumping and valving arrangement. One such type of solution is a saline solution. A reinfusion of the saline bag(s) may be performed if necessary.

During the dialysis process, the CPUs 610,616 in the control module 25 for the machine continuously monitor the various sensors (temperature, pressure, conductivity, air, blood, flow rate, UF tank level, etc.) in the various modules 24, 26 and 28. Any errors in the monitoring and controlling of the various systems is controlled by an exception handling routine which would take appropriate action to recover the operation or notify the user of abnormalities. Additionally, prior to treatment, the patient's blood pressure is taken and the updated blood pressures are logged in a treatment log. When the treatment is complete, the message is displayed to the user and if the user desires more treatment the system continues to perform the dialysis. After the treatment is complete, or error conditions exist which cannot be recovered, the dialysis is stopped and the system enters a rinseback sequence (FIG. 22).

E. Rinseback Sequence 712

The rinseback sequence 712 is illustrated generally in FIG. 22. When the dialysis session has been completed, the touch screen 602 in the central control module 25 displays a prompt to the patient asking whether the patient wishes to have the remaining blood in the extracorporeal circuit rinsed back to the patient. The blood pump 458 is also stopped. Other initial conditions are that the UF pump 242 is off, the blood pump 458 is on at the prescribed speed and the dialyze alarms are still active.

At mode 832, when the command to continue is received, dialysate is pumped through the dialyzer 404 and the tank 202 is pressurized to equal the starting pressure measured at pressure sensor 410. Bypass valve 412 is opened and valves 414 and 416 are closed. The blood pump 458 is stopped. The arterial and venous line clamps are closed.

At step 838, the system determines whether a dialysate or a saline rinse is to be performed. If dialysate rinse is performed, the system enters a mode 834. In this mode, the heater 228 is turned off, pump 212 is stopped, and the valves in the module 26 are switched to direct dialysate from the tank 202 to the dialyzer 404 inlet line 414 via the UF pump 242. The arterial and venous clamps 242 are opened. The blood pump 458 is pumped in reverse at one half the UF pump rate. The UF pump 242 pumps dialysate from the dialysate circuit through the dialyzer 404 into the extracorporeal circuit 400, pumping blood in the extracorporeal circuit 400 in equal volumes out the arterial and venous lines 432, 492 back to the patient.

The optical sensors 446 and 486 in the arterial and venous lines 432, 492 sense the concentration of blood in the lines 432, 492 as the blood is being pumped from the extracorporeal circuit back to the patient. The sensors 446 and 486 issue signals to the CPU in the control module 25. The CPU 610 monitors the signals and when the signals indicate the concentration of blood in the lines has reached a predetermined threshold level, the blood pump 458 is stopped, thereby preventing excess fluids from being returned to the patient.

When the pressure in the extracorporeal circuit 400 is stabilized, the arterial and venous clamps 444 and 490 of the arterial and venous lines 432 and 492, respectively, are closed. The A user disconnect message is displayed and the patient reconnects the ends of the arterial and venous lines 432, 492 to the ports 499, 497 respectively, of the disinfection manifold 494. The patient also removes line 482 from port 483 to port 495. The sensors 648 (FIG. 39C) in the disinfection manifold confirm whether the lines are reconnected to the disinfection manifold 494.

The user is prompted to install new chemical bottles 270 onto the chemical applicators 260. The readers for the machine-readable identifiers (such as touch buttons) on the bottle send bottle information to the CPU 610, which then alerts the user if the wrong bottle is installed. A message is then displayed to the user to connect the water inlet and drain outlet of the machine to water inlet and drain lines (if not already so connected).

The user is then prompted to take chloramine samples from the sample removal ports in the water pretreatment module 20, and, if necessary, change the filter unit 40. After the user has inputted an "O.K." response that the chloramine test was passed, the rinseback mode is ended and the machine enters a clean and rinse mode.

If saline rinse is performed (mode 836), the heater 228 is turned off, the dialysate pump 212 is turned off, and a message is displayed to unclamp the arterial fistula and unclamp the saline line. The arterial air bubble detector is disabled. The blood pump 458 is run in the forward direction, pumping saline though the arterial line 432 and blood and saline out venous line 492. The dialysate valves are directed away from the filter 234 back to the tank 202. When the blood concentration sensed limit, us blood sensor 486 has reached a predetermined limit, the blood pump 458 is stopped, the pressures in the extracorporeal circuit are stabilized and the arterial and venous clamps are closed. The user is prompted to disconnect from the machine and the process continues the same as for the dialysate rinse mode 834 above.

F. Clean and Rinse Sequence 714

The clean and rinse mode 714 is illustrated in FIG. 23. The machine next makes two passes through the steps 850–866 in FIG. 23. At drain A mode and step 850, the dialysate preparation tank 202 and UF tank 244 are drained from the machine 22. Step 852 and 854 are the same as steps 742 and 760 of FIG. 18, respectively, which were described earlier. At step 856, the chemical ports in the loading platform 250 are flushed with water. Steps 858 and 860 are the same as steps 756 and 744 of FIG. 18, respectively. The dialyzer 404 is then cleaned on-line in step 862. Steps 864 and 866 are the same as steps 748 and 750, described earlier. At step 868, the tank 202 is drained. The waste water is pumped out drain line 71 to drain output 51. After the clean and rinse mode of FIG. 23 has been completed, the machine enters an idle mode and waits for the next disinfection session to begin.

Our preferred technique for on-line, in situ dialyzer cleaning is to use automatic hot water agitation of the blood and dialysate sides of the dialyzer membrane, followed by flushing of the dialyzer. No chemicals are used. The blood circuit is further not subjected to airborne bacteria. The hot water agitation involves heating RO water (or physiologic dialysate) with heater 228 to a temperature of between 37° C. to 85° C., introducing the heated water into the extracorporeal circuit via the disinfection manifold 494 and introducing pressure pulses in the extracorporeal circuit and dialyzer in the manner described above in connection with the dialyzer prime mode 735. We further back flush RO water across the dialyzer from the dialysate side to the blood side of the membrane with pressure pulses introduced in the dialysate circuit 402. The particulate matter, blood products and other material which maybe adhered to the fibers in the dialyzer 404 are thereby removed from the surface of the fibers. By periodically flushing the extracorporeal circuit with RO water and returning the fluid to the drain during this process, the life expectancy of the dialyzer 404 is substantially prolonged.

In particular, backflushing of the dialyzer 404 is accomplished by clamping valve 416 and opening valve V14 to drain. The blood pump 458 is started in a reverse direction at approximately ½ the rate of the UF pump 242 using the dialysate which provides a physiologic solution to keep the blood products from clotting and forming more difficult substances to remove. The flow rate of the UF 242 and blood 458 pumps is limited by the maximum pressure at pressure transducer 410. The system will adjust the flow rates until either flow meter 241 reaches the preset maximum flow rate, approximately 600 ml/min, or pressure transducer 410 reaches the preset maximum flow rate. The flow rate measurement by flow meter 241 can be stored by the central processing unit 610 and can be correlated to the amount of fiber blockage in the system, i.e. the lower the initial flow rate, the greater the amount of blockage. If the flow rate does not reach a shed level of approximately 500 ml/min after the time allotted for backflushing, then the dialyzer can be identified as too blocked for usage by the central processing unit 610. The user will then be alerted at the beginning of the next treatment that the extracorporeal circuit needs to be replaced before dialysis can continue.

Systematic forward and reverse flowing of the fluid in the extracorporeal circuit is accomplished by driving the blood pump 458 in a forward or reverse direction with the valves V14, 414, 416 closed and V20 open. This isolates the extracorporeal circuit 400 from the rest of the dialysis system and allows the fluid to be recirculated to scrub the residual blood products out of the extracorporeal circuit. This forward and reverse flow is continued for a preset time. At the end of the cycle, the fluid in the extracorporeal circuit 400 with the removed blood products is set to drain by opening V14, and backflushing the dialyzer as outlined above. This procedure can be repeated as many times as desired.

VII. Auxiliary Functions of Machine 22

Preferably, the machine 22 has the capacity for automatic communication of a treatment report to a central station or other entity monitoring the patient's hemodialysis. This would normally be accomplished by including in the machine 22 a fax modem connected to a phone line that is programmed to automatically fax a report of the hemodialysis treatment to the center. The treatment reports would include such information as the patient's name, address and phone number, the date and time of the report, the pretreatment weight, blood pressure, pulse and temperature, a dialysate code, conductivity measurements and clearance, heparin information, and the results of periodic measurements during dialysis such as blood flow rate dialysate flow rate, arterial pressure, venous pressure, blood pressure, pulse, UF rate, total UF volume and additional comments. Additional information which may be included in the treatment reports would be the occurrence of incidents such as when blood flow was stopped, at what time, when it was resumed, and any alarms that occurred. Additional information would include the time the treatment was ended, the total dialysis time and the calculated KT/V for the treatment. Finally, treatment reports could include the post-treatment weight, post-treatment blood pressure, and answers to post-treatment assessment questions. Weekly treatment summaries, in numeric and graphical form, of the fluid removed, KT/V and blood pressure would also be provided. The interface and control module 25 would be provided with internal data retention and storage capacity (such as a hard disk drive) for storing such information (such as a random access memory) until the data is later sent to a center. Equipment for local print-out for the treatment report is a further accessory for the machine 22.

Preferably, the user interface and control module 25 for the dialysis machine 22 includes a software diagnostic routine which can be accessed from the user interface to check the various sensors in the unit 22 and to manipulate its activity. Ideally, the diagnostic routine will be able to be accessed remotely by a modem such that service entity for the machine 22 can check the sensors, failure codes and other diagnostics in the machine 22 remotely. Since the various modules 24, 26, and 28 of the unit 22 are modular, failures or servicing of the various modules in a relatively easy by replacing or swapping modules 24, 26 or 28.

Figure 41:
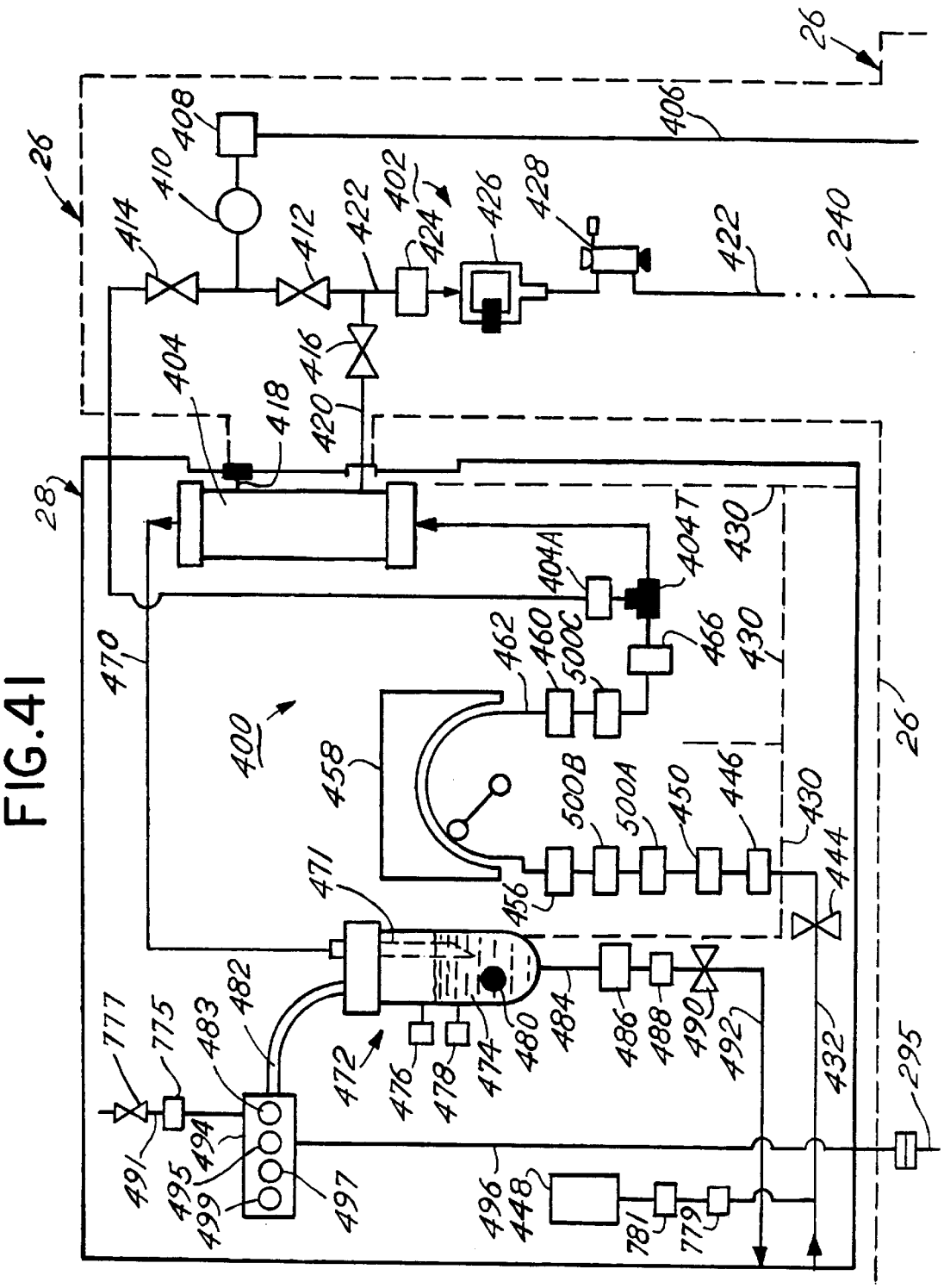
FIG. 41 is an illustration of a hemofiltration with pre-dilution embodiment of the invention.

From the foregoing description it will be appreciated that the inventive techniques, flowpath and system components and subcomponents may be used to provide hemofiltration and hemodiafiltration. Hemofiltration with pre-dilution is accomplished as follows. The output of the dialysate tank 202 will be directed as before through the dialysate filter (pyrogen/ultrafilter) 234. However, the output of the dialysate filer 234 will be directed to a second depyrogenation filter 404A, the output of which will be directed via T connector 404T into the extracorporeal blood circuit 400 upstream of the blood inlet of the dialyzer 404. Dialysate line 418 is blocked off as shown. See FIG. 41. The closed volume principle which allows the control of ultrafiltration in normal dialysis will also apply here such that any solution directed into the blood circuit 400 will be pulled back into the dialysate tank 202 through the dialyzer outlet line. The ultrafiltration pump 242 may still be used to remove excess fluid.

Figure 42:
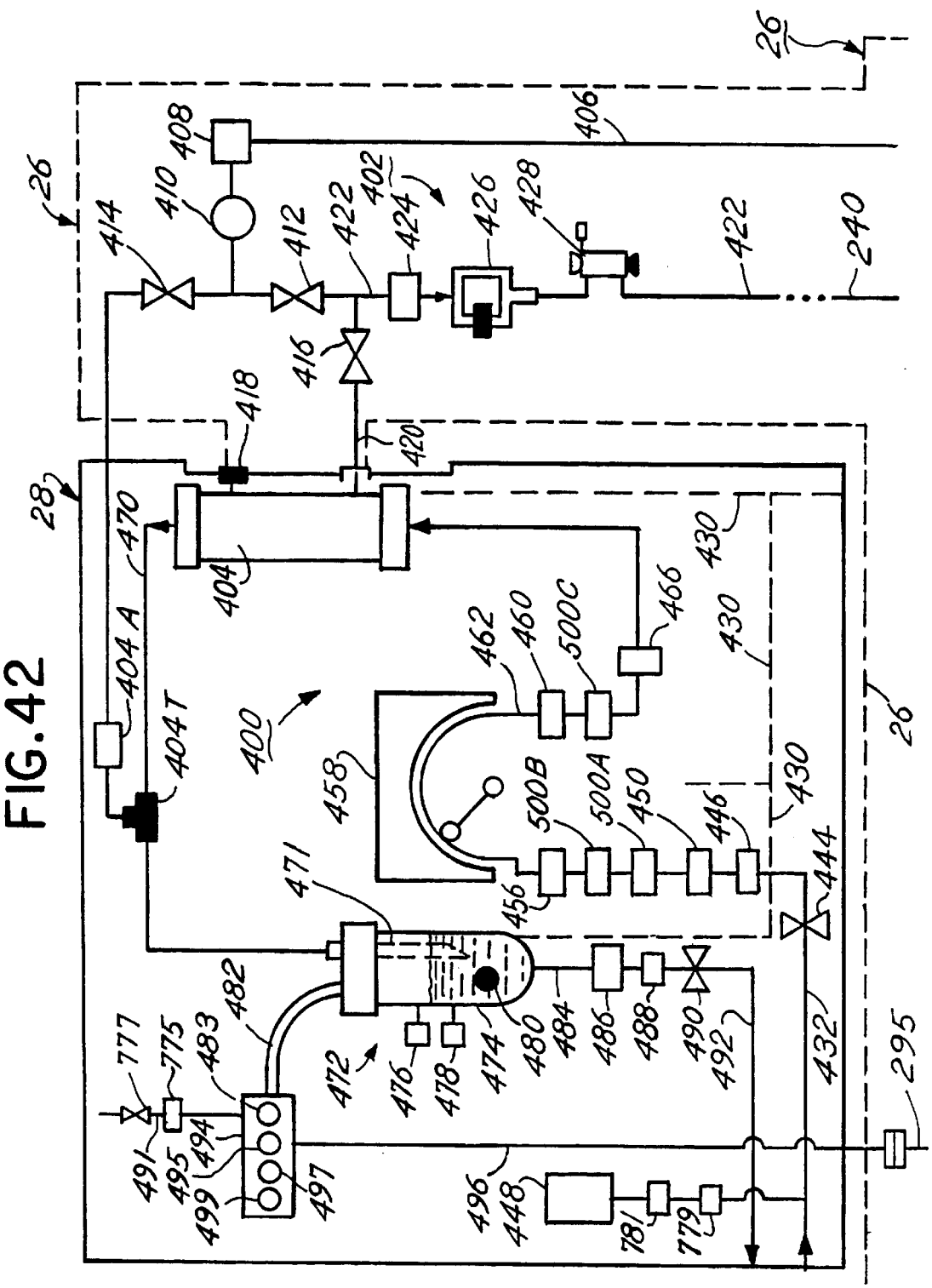
FIG. 42 is an illustration of a hemofiltration with post-dilution embodiment of the invention.

For hemofiltration with post-dilution, the technique is the same as for hemofiltration with pre-dilution, but the output of the second depyrogenation filter 404A will be directed into the blood circuit 400 following the blood outlet of the dialyzer 404 at T connector 404T. See FIG. 42.

Figure 43:
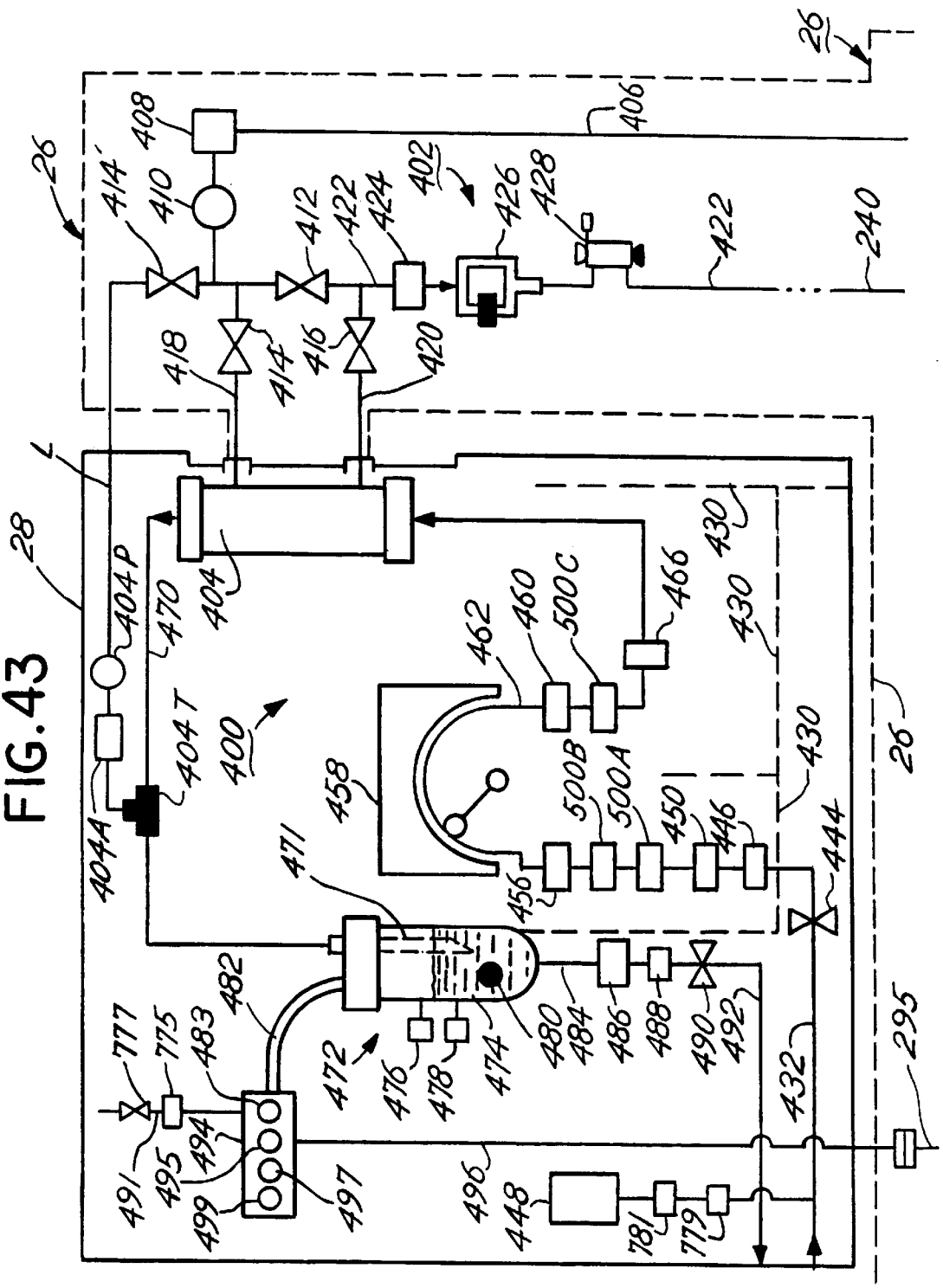
FIG. 43 is an illustration of a hemodiafiltration with post-dilution embodiment of the invention.

For hemodiafiltration with post-dilution, the technique is the same as for hemodiafiltration with pre-dilution, except that the output of the second depyrogenation filter 404A is directed via T connector 404A to the blood circuit 400 downstream of the outlet of the dialyzer 404. See FIG. 43. A valve 414' and peristaltic pump 404P are placed in dialysate line L. Line 418 is open via valve 414.

For hemodiafiltration with mid-dilution, in this implementation there is no second depyrogenation filter. Instead, the ultrafiltration pump 242 is used to backflush ultrapure dialysate into the dialyzer 404 and then to remove this excess fluid. See FIG. 43.

A further additional aspect of the invention is that the use of the tank 202 (which may be the same size or smaller) and the same chemical mixing approach described herein, but to prepare a more concentrated batch of dialysate which can be proportioned with the reverse osmosis output water during the dialysis treatment. This would be particularly useful in longer treatments. The same size tank or a smaller tank 202 maybe used. However, rather than mixing up a fully dilute batch of dialysate, a concentrated batch of dialysate is prepared (using the same chemical addition principles as described in conjunction with the discussion of the dialysate preparation module 26). This batch may then be proportioned with reverse osmosis product water during the dialysis session to achieve longer treatments without enlarging the size of the tank required. The incoming reverse osmosis water will be heated, and there is a means for insuring that the concentrated dialysate solution and the incoming reverse osmosis water are thoroughly mixed. The incoming reverse osmosis water can be heated such as by the use of temperature controlled mixing valve in the water pretreatment module 20. The means for insuring that the concentrated dialysate and the incoming reverse osmosis water are thoroughly mixed can be achieved by monitoring the conductivity of the solution as the concentrated dialysate is taken out of the tank 202 past through conductivity sensor 218 and returned to the top of the tank in conjunction with the mixing principles above.

VIII. Conclusion

From the forgoing detailed description, it will be apparent to a person of ordinary skill in the art that many variations and modifications of the preferred and alternative embodiments of the invention may be made, without departure from the true spirit and scope of the invention. The term "module", as used herein and in the claims, is intended to be broadly interpreted as encompassing a component or group of components that perform a specified function, such as treat water or prepare a dialysate solution, whether or not such component or group of components is physically encased within a housing physically apart from other components. Obviously, the selection of components that comprises a "module" is a matter of design choice. For example, the dialysate circuit 402 is shown as part of the dialysate preparation module 26, but could just as easily been made part of the extracorporeal circuit module 28, with suitable connectors in the lines leading to and from the dialysate side of the dialyzer. The true spirit and scope of the invention is defined by the appended claims, to be interpreted in light of the forgoing specification.

Further, the term "purified water" used herein means water in which impurities have been removed. The technical definition of "purified water", such as found in the United States Pharmacopoeia, is not intended.

We claim:

1. A hemodialysis machine with automatic priming of a dialyzer membrane, comprising:

a dialyzer having a blood side thereof and a dialysate side thereof, said dialyzer membrane separating said blood side of said dialyzer from said dialysate side of said dialyzer;

a dialysate circuit circulating dialysate solution to said dialysate side of said dialyzer;

an extracorporeal circuit having arterial and venous blood lines connecting a patient to said dialyzer;

a means for introducing fluid into said arterial and venous lines and for filling said arterial and venous lines and said blood side of said dialyzer with said fluid;

a blood pump in said extracorporeal circuit for pumping fluids in said arterial and venous lines;

first and second clamps clamping said arterial and venous blood lines, respectively;

a control system operative of said first and second clamps and said blood pump in a priming mode to achieve automatically priming of said dialyzer, said control system operating said blood pump and said first and second clamps in a manner to induce multiple brief pressure pulses in said extracorporeal circuit when said extracorporeal circuit is substantially filled with said fluid, said pressure pulses shearing off air bubbles from said blood side of said membrane; said control system and blood pump operative to remove said air bubbles from said blood side of said dialyzer membrane and out of said extracorporeal circuit.

2. The hemodialysis machine of claim 1, further comprising a dialysate pump, said control system further operative of said dialysate pump to force fluid in said dialysate circuit through said dialyzer membrane from said dialysate side thereof into said blood side thereof in synchrony with said induced multiple brief pressure pulses in said fluid filling said extracorporeal circuit to thereby promote the removal of air bubbles from said dialyzer membrane.

3. The hemodialysis machine of claim 1, wherein said fluid comprises a dialysate solution.

* * * * *